(12) United States Patent
Baurin et al.

(10) Patent No.: US 9,181,349 B2
(45) Date of Patent: Nov. 10, 2015

(54) DUAL VARIABLE REGION ANTIBODY-LIKE BINDING PROTEINS HAVING CROSS-OVER BINDING REGION ORIENTATION

(71) Applicants: Nicolas Baurin, Arpajon (FR); Chirstian Biel, Kelkheim (DE); Carsten Corvey, Kelkheim (DE); Christian Lange, Holler (DE); Danxi Li, Skillman, NJ (US); Vincent Mikol, Charenton-le-Pont (FR); Anke Steinmetz, Vitry sur Seine (FR); Ercole Rao, Moerfelden-Walldorf (DE)

(72) Inventors: Nicolas Baurin, Arpajon (FR); Chirstian Biel, Kelkheim (DE); Carsten Corvey, Kelkheim (DE); Christian Lange, Holler (DE); Danxi Li, Skillman, NJ (US); Vincent Mikol, Charenton-le-Pont (FR); Anke Steinmetz, Vitry sur Seine (FR); Ercole Rao, Moerfelden-Walldorf (DE)

(73) Assignee: SANOFI, Paris (FR)

( * ) Notice: Subject to any disclaimer, the term of this patent is extended or adjusted under 35 U.S.C. 154(b) by 35 days.

(21) Appl. No.: 13/826,126

(22) Filed: Mar. 14, 2013

(65) Prior Publication Data
US 2014/0011238 A1      Jan. 9, 2014

Related U.S. Application Data

(62) Division of application No. 13/433,033, filed on Mar. 28, 2012, now abandoned.

(60) Provisional application No. 61/468,276, filed on Mar. 28, 2011.

(30) Foreign Application Priority Data

Nov. 14, 2011   (FR) ...................................... 1160311

(51) Int. Cl.
| *C07K 16/46* | (2006.01) |
| *C07K 16/00* | (2006.01) |
| *C07K 16/24* | (2006.01) |
| *C07K 16/28* | (2006.01) |
| *C07K 16/32* | (2006.01) |

(52) U.S. Cl.
CPC ................. *C07K 16/46* (2013.01); *C07K 16/00* (2013.01); *C07K 16/241* (2013.01); *C07K 16/244* (2013.01); *C07K 16/247* (2013.01); *C07K 16/2863* (2013.01); *C07K 16/2866* (2013.01); *C07K 16/32* (2013.01); *C07K 16/461* (2013.01); *C07K 16/468* (2013.01); *C07K 2317/21* (2013.01); *C07K 2317/24* (2013.01); *C07K 2317/624* (2013.01); *C07K 2317/64* (2013.01); *C07K 2317/76* (2013.01); *C07K 2317/92* (2013.01); *C07K 2317/94* (2013.01)

(58) Field of Classification Search
CPC ............................ C07K 16/00–16/468; C07K 2317/00–2317/94
See application file for complete search history.

(56) References Cited

U.S. PATENT DOCUMENTS

| 5,736,137 | A | 4/1998 | Anderson et al. | |
|---|---|---|---|---|
| 5,989,830 | A | 11/1999 | Davis et al. | |
| 6,057,098 | A | 5/2000 | Buechler et al. | |
| 6,090,382 | A | 7/2000 | Salfeld et al. | |
| 6,239,259 | B1 | 5/2001 | Davis et al. | |
| 7,612,181 | B2 | 11/2009 | Wu et al. | |
| 8,388,965 | B2 * | 3/2013 | Rao et al. | 424/136.1 |
| 2005/0003403 | A1 | 1/2005 | Rossi et al. | |
| 2007/0071675 | A1 | 3/2007 | Wu et al. | |
| 2009/0060910 | A1 * | 3/2009 | Johnson et al. | 424/133.1 |
| 2010/0226923 | A1 | 9/2010 | Rao et al. | |
| 2010/0331527 | A1 | 12/2010 | Davis et al. | |
| 2013/0209469 | A1 * | 8/2013 | Rao et al. | 424/136.1 |
| 2013/0236460 | A1 * | 9/2013 | Rao et al. | 424/136.1 |
| 2013/0236461 | A1 * | 9/2013 | Rao et al. | 424/136.1 |
| 2013/0236462 | A1 * | 9/2013 | Rao et al. | 424/136.1 |
| 2013/0236463 | A1 * | 9/2013 | Rao et al. | 424/136.1 |
| 2013/0243776 | A1 * | 9/2013 | Rao et al. | 424/136.1 |
| 2013/0243777 | A1 * | 9/2013 | Rao et al. | 424/136.1 |
| 2013/0243778 | A1 * | 9/2013 | Rao et al. | 424/136.1 |
| 2013/0251716 | A1 * | 9/2013 | Rao et al. | 424/136.1 |
| 2013/0251717 | A1 * | 9/2013 | Rao et al. | 424/136.1 |
| 2013/0251718 | A1 * | 9/2013 | Rao et al. | 424/136.1 |
| 2013/0259866 | A1 * | 10/2013 | Rao et al. | 424/136.1 |
| 2013/0344074 | A1 * | 12/2013 | Bender et al. | 424/136.1 |
| 2013/0345404 | A1 * | 12/2013 | Baurin et al. | 530/387.3 |
| 2014/0023649 | A1 * | 1/2014 | Rao et al. | 424/136.1 |
| 2014/0056895 | A1 * | 2/2014 | Baurin et al. | 424/136.1 |
| 2014/0213772 | A1 * | 7/2014 | Ghayur et al. | 530/387.3 |

FOREIGN PATENT DOCUMENTS

| EP | 2 050 764 A1 | 4/2009 |
|---|---|---|
| WO | 93/11161 A1 | 6/1993 |
| WO | 9411026 A2 | 5/1994 |
| WO | 97/14719 A1 | 4/1997 |
| WO | 97/29131 A1 | 8/1997 |

(Continued)

OTHER PUBLICATIONS

Bird et al., "Single-chain antigen-binding proteins," Science 242(4877):423-26 (1988).

(Continued)

*Primary Examiner* — Sheela J Huff
*Assistant Examiner* — Jessica H Roark
(74) *Attorney, Agent, or Firm* — McDonnell Boehnen Hulbert and Berghoff LLP

(57) ABSTRACT

The invention provides antibody-like binding proteins comprising four polypeptide chains that form four antigen binding sites, wherein each pair of polypeptides forming an antibody-like binding protein possesses dual variable domains having a cross-over orientation. The invention also provides methods for making such antigen-like binding proteins.

26 Claims, 8 Drawing Sheets

(56) References Cited

FOREIGN PATENT DOCUMENTS

| WO | 2008/024188 | A2 | | 2/2008 |
|---|---|---|---|---|
| WO | WO2009/021754 | A2 | * | 2/2009 |
| WO | 2009052081 | | | 4/2009 |
| WO | 2011/014659 | A2 | | 2/2011 |
| WO | 2012/135345 | A1 | | 10/2012 |

OTHER PUBLICATIONS

Brinkmann et al., "A recombinant immunotoxin containing a disulfide-stabilized Fv fragment," Proc. Natl. Acad. Sci. U.S.A. 90(16):7538-42 (1993).

Carter et al., "Toward the production of bispecific antibody fragments for clinical applications," J. Hematother. 4 (5):463-70 (1995).

Carter, "Bispecific human IgG by design," J. Immunol. Methods 248(1-2):7-15 (2001).

Davis et al., "SEEDbodies: fusion proteins based on strand-exchange engineered domain (SEED) CH3 heterodimers in an Fc analogue platform for asymmetric binders or immunofusions and bispecific antibodies," Protein Eng. Des. Sel. 23(4):195-202 (2010).

De Kruif & Logtenberg, "Leucine zipper dimerized bivalent and bispecific scFv antibodies from a semi-synthetic antibody phage display library," J. Biol. Chem. 271(13):7630-34 (1996).

Durocher et al., "High-level and high-throughput recombinant protein production by transient transfection of suspension-growing human 293-EBNA1 cells," Nucl. Acids Res. 30(2):E9 (2002).

George & Huston, The Antibodies, Chapter 6:99-141, "Bispecific Antibody Engineering," (Zanetti & Capra, eds., Harwood Academic Publishers, Luxembourg, vol. 4 (1997).

Gunasekaran et al., "Enhancing antibody Fc heterodimer formation through electrostatic steering effects: applications to bispecific molecules and monovalent IgG," J. Biol. Chem. 285(25):19637-46 (2010).

Holliger et al., ""Diabodies": small bivalent and bispecific antibody fragments," Proc. Nat'l. Acad. Sci. U.S.A. 90 (14):6444-48 (1993).

Hudson & Kortt, "High avidity scFv multimers; diabodies and triabodies," J. Immunol. Methods 231(1-2):177-89 (1999).

Kostelny et al., "Formation of a bispecific antibody by the use of leucine zippers," J. Immunol. 148(5):1547-53 (1992).

Lindhofer et al., "Preferential species-restricted heavy/light chain pairing in rat/mouse quadromas. Implications for a single-step purification of bispecific antibodies," J. Immunol. 155(1):219-25 (1995).

Mack et al., "A small bispecific antibody construct expressed as a functional single-chain molecule with high tumor cell cytotoxicity," Proc. Natl. Acad. Sci. U.S.A. 92(15):7021-25 (1995).

Mallender & Voss, "Construction, expression, and activity of a bivalent bispecific single-chain antibody," J. Biol. Chem. 269(1):199-206 (1994).

Merchant et al., "An efficient route to human bispecific IgG," Nat. Biotechnol. 16(7):677-81 (1998).

Milstein & Cuello, "Hybrid hybridomas and their use in immunohistochemistry," Nature 305(5934):537-40 (1983).

Plückthun & Pack, "New protein engineering approaches to multivalent and bispecific antibody fragments," Immunotechnology 3(2):83-105 (1997).

Ridgway et al., ""Knobs-into-holes" engineering of antibody CH3 domains for heavy chain heterodimerization," Protein Eng. 9(7):617-21 (1996).

Staerz et al., "Hybrid antibodies can target sites for attack by T cells," Nature 314(6012):628-31 (1985).

Todorovska et al., "Design and application of diabodies, triabodies and tetrabodies for cancer targeting," J. Immunol, Methods 248(1-2):47-66 (2001).

Ward et al., "Binding activities of a repertoire of single immunoglobulin variable domains secreted from *Escherichia coli*," Nature 341(6242):544-46 (1989).

"Development of biologically active peptides based on antibody structure," Proc. Natl. Acad. Sci. U.S.A. 86(14):5537-41 (1989).

Wörn & Plückthun, "Stability engineering of antibody single-chain Fv fragments," J. Mol. Biol. 305(5):989-1010 (2001).

Wozniak-Knopp et al., "Stabilisation of the Fc Fragment of Human IgG1 by Engineered Intradomain Disulfide Bonds," PLoS One 7(1):e30083 (2012).

International Search Report and Written Opinion of the International Searching Authority, mailed Aug. 29, 2012 in International Application No. PCT/US2012/030948.

Response to Written Opinion of the International Searching Authority, filed Nov. 29, 2012 in International Application No. PCT/US2012/030948.

Written Opinion of the International Preliminary Examining Authority, mailed Mar. 8, 2013 in International Application No. PCT/US2012/030948.

Cuesta et al., "Multivalent antibodies: when design surpasses evolution," Trends Biotechnol. 28(7):355-62 (2010).

Replacement Request for Inter Partes Reexamination, filed Jun. 24, 2010 in Reexamination Control No. 95/001,380.

Miller et al., "Design, construction, and in vitro analyses of multivalent antibodies," J. Immunol. 170: 4854-61 (2003).

Muller et al., "The first constant domain (C(H)1 and C(L)) of an antibody used as heterodimerization domain for bispecific miniantibodies," FEBS Lett. 422: 259-64 (1998).

Lu et al., "A fully human recombinant IgG-like bispecific antibody to both the epidermal growth factor receptor and the insulin-like growth factor receptor for enhanced antitumor activity," J. Biol. Chem. 280(20): 19665-72 (2005).

Lu et al., "Di-diabody: a novel tetravalent bispecific antibody molecule by design," J. Immunol. Methods 279(1-2): 219-32 (2003).

Lu et al., "Simultaneous blockade of both the epidermal growth factor receptor and the insulin-like growth factor receptor signaling pathways in cancer cells with a fully human recombinant bispecific antibody," J. Biol. Chem. 279(4): 2856-65 (2004).

Zuo et al., "An efficient route to the production of an IgG-like bispecific antibody," Prot. Eng. 13(5): 361-67 (2000).

Order Granting/Denying Request for Inter Partes Reexamination, mailed Sep. 1, 2010 in Reexamination Control No. 95/001,380.

Office Action in Inter Partes Reexamination, mailed Sep. 1, 2010 in Reexamination Control No. 95/001,380.

Response Pursuant to 37 CFR § 1.945, filed Nov. 1, 2010 in Reexamination Control No. 95/001,380.

Sanofi's Comments Pursuant to 37 C.F.R. § 1.947, filed Dec. 1, 2010 in Reexamination Control No. 95/001,380.

Declaration of Paul J. Davis, Ph.D. in Support of Third Party Requester's Comments, executed and filed Dec. 1, 2010 in Reexamination Control No. 95/001,380.

Wooldridge et al., "Tricks with tetramers: how to get the most from multimeric peptide—MHC," Immunology 126(2): 147-64 (2009).

Action Closing Prosecution (37 CFR 1.949), mailed Sep. 1, 2011 in Reexamination Control No. 95/001,380.

Response Pursuant to 37 CFR § 1.951(a), filed Oct. 31, 2011 in Reexamination Control No. 95/001,380.

Declaration, of Dr. Roland Kontermann, executed Oct. 26, 2011, filed Oct. 31, 2010 in Reexamination Control No. 95/001,380.

Sanofi's Comments Pursuant to 37 C.F.R. § 1.947, filed Nov. 30, 2011 in Reexamination Control No. 95/001,380.

Declaration of Ercole Rao, Ph.D. in Support of Third Party Requester's Comments, executed Nov. 24, 2011, filed Nov. 30, 2011 in Reexamination Control No. 95/001,380.

Declaration of Paul J. Davis Ph.D. and Martine Verhoeyen Ph.D. in Support of Third Party Requester's Comments, executed and filed Nov. 30, 2011 in Reexamination Control No. 95/001,380.

Langman, "The Immune System: Evolutionary Principles Guide Our Understanding of This Complex Biological Defense System," 1989, pp. 96, 65, 66 (Academic Press, Inc., San Diego, CA).

Right of Appeal Notice (37 CFR 1.953), mailed Mar. 7, 2012 in Reexamination Control No. 95/001,380.

Appellants' Brief in Support of the Appeal to the Board of Patent Appeals and Interferences, filed Jun. 6, 2012 in Reexamination Control No. 95/001,380.

Morrison, "A new design for bispecific antibodies enables efficient production of stable molecules with good pharmacodynamic properties," Nat. Biotechnol. 25(11): 1233-34 (2007).

Presta, "Molecular Engineering and design of therapeutic antibodies," Curr. Opin. Immunol. 20(4): 460-70 (2008).

(56) References Cited

OTHER PUBLICATIONS

Fischer, "New magic bullets can hit more than one target," Expert Opin. Drug Discov. 3(8): 833-39 (2008).

Gavrilyuk et al., "An Efficient Chemical Approach to Bispecific Antibodies and Antibodies of High Valency," Bioorg Med. Chem. Lett. 19(14): 3716-20 (2009).

Chan et al., "Therapeutic Antibodies for Autoimmunity and Inflammation," Nat. Rev. Immunol., 10(5): 301-16 (2010).

Kontermann, Roland E., ed., "Bispecific Antibodies," 2011 (Springer-Verlag Berlin Heidelberg).

Wu et al., "Simultaneous targeting of multiple disease mediators by a dual-variabledomain immunoglobulin," Nat. Biotechnol. 25: 1290-97 (2007).

Merchant et al. "An efficient route to human bispecific IgG," Nat. Biotechnol., 16(7): 677-81 (1998).

Respondent/Patent Owner's Brief, filed Jul. 6, 2012 in Reexamination Control No. 95/001,380.

Inter Partes Reexamination Examiner's Answer, mailed Jun. 5, 2013 in Reexamination Control No. 95/001,380.

* cited by examiner

DUAL VARIABLE REGION ANTIBODY-LIKE BINDING PROTEINS HAVING CROSS-OVER BINDING REGION ORIENTATION

CROSS REFERENCE TO RELATED APPLICATIONS

This application is a divisional of U.S. application Ser. No. 13/433,033, filed Mar. 28, 2012, which claims the benefit of priority from U.S. Provisional Application No. 61/468,276, filed Mar. 28, 2011, and French Patent Application No. 1160311, filed Nov. 14, 2011, the disclosures of which are incorporated by reference herein in their entirety.

FIELD OF THE INVENTION

The invention relates to antibody-like binding proteins comprising four polypeptide chains that form four antigen binding sites, wherein each pair of polypeptides forming the antibody-like binding protein possesses dual variable domains having a cross-over orientation. The invention also relates to methods for making such antigen-like binding proteins.

BACKGROUND OF THE INVENTION

Naturally occurring IgG antibodies are bivalent and monospecific. Bispecific antibodies having binding specificities for two different antigens can be produced using recombinant technologies and are projected to have broad clinical applications. It is well known that complete IgG antibody molecules are Y-shaped molecules comprising four polypeptide chains: two heavy chains and two light chains. Each light chain consists of two domains, the N-terminal domain being known as the variable or $V_L$ domain (or region) and the C-terminal domain being known as the constant (or $C_L$) domain (constant kappa (Cκ) or constant lambda (Cλ) domain). Each heavy chain consists of four or five domains, depending on the class of the antibody. The N-terminal domain is known as the variable (or $V_H$) domain (or region), which is followed by the first constant (or $C_{H1}$) domain, the hinge region, and then the second and third constant (or $C_{H2}$ and $C_{H3}$) domains. In an assembled antibody, the $V_L$ and $V_H$ domains associate together to form an antigen binding site. Also, the $C_L$ and $C_{H1}$ domains associate together to keep one heavy chain associated with one light chain. The two heavy-light chain heterodimers associate together by interaction of the $C_{H2}$ and $C_{H3}$ domains and interaction between the hinge regions on the two heavy chains.

It is known that proteolytic digestion of an antibody can lead to the production of antibody fragments (Fab and Fab2). Such fragments of the whole antibody can exhibit antigen binding activity. Antibody fragments can also be produced recombinantly. Fv fragments, consisting only of the variable domains of the heavy and light chains associated with each other may be obtained. These Fv fragments are monovalent for antigen binding. Smaller fragments such as individual variable domains (domain antibodies or dABs; Ward et al., 1989, Nature 341(6242): 544-46), and individual complementarity determining regions or CDRs (Williams et al., 1989, Proc. Natl. Acad. Sci. U.S.A. 86(14): 5537-41) have also been shown to retain the binding characteristics of the parent antibody, although most naturally occurring antibodies generally need both a $V_H$ and $V_L$ to retain full binding potency.

Single chain variable fragment (scFv) constructs comprise a $V_H$ and a $V_L$ domain of an antibody contained in a single polypeptide chain wherein the domains are separated by a flexible linker of sufficient length (more than 12 amino acid residues), that forces intramolecular interaction, allowing self-assembly of the two domains into a functional epitope binding site (Bird et al., 1988, Science 242(4877): 423-26). These small proteins (MW ~25,000 Da) generally retain specificity and affinity for their antigen in a single polypeptide and can provide a convenient building block for larger, antigen-specific molecules.

An advantage of using antibody fragments rather than whole antibodies in diagnosis and therapy lies in their smaller size. They are likely to be less immunogenic than whole antibodies and more able to penetrate tissues. A disadvantage associated with the use of such fragments is that they have only one antigen binding site, leading to reduced avidity. In addition, due to their small size, they are cleared very fast from the serum, and hence display a short half-life.

It has been of interest to produce bispecific antibodies (BsAbs) that combine the antigen binding sites of two antibodies within a single molecule, and therefore, would be able to bind two different antigens simultaneously. Besides applications for diagnostic purposes, such molecules pave the way for new therapeutic applications, e.g., by redirecting potent effector systems to diseased areas (where cancerous cells often develop mechanisms to suppress normal immune responses triggered by monoclonal antibodies, like antibody-dependent cellular cytotoxicity (ADCC) or complement-dependent cytotoxicity (CDC)), or by increasing neutralizing or stimulating activities of antibodies. This potential was recognized early on, leading to a number of approaches for obtaining such bispecific antibodies. Initial attempts to couple the binding specificities of two whole antibodies against different target antigens for therapeutic purposes utilized chemically fused heteroconjugate molecules (Staerz et al., 1985, Nature 314(6012): 628-31).

Bispecific antibodies were originally made by fusing two hybridomas, each capable of producing a different immunoglobulin (Milstein et al., 1983, Nature 305(5934): 537-40), but the complexity of species (up to ten different species) produced in cell culture made purification difficult and expensive (George et al., 1997, THE ANTIBODIES 4: 99-141 (Capra et al., ed., Harwood Academic Publishers)). Using this format, a mouse IgG2a and a rat IgG2b antibody were produced together in the same cell (e.g., either as a quadroma fusion of two hybridomas, or in engineered CHO cells). Because the light chains of each antibody associate preferentially with the heavy chains of their cognate species, three major species of antibody are assembled: the two parental antibodies, and a heterodimer of the two antibodies comprising one heavy/light chain pair of each, associating via their Fc portions. The desired heterodimer can be purified from this mixture because its binding properties to Protein A are different from those of the parental antibodies: rat IgG2b does not bind to Protein A, whereas the mouse IgG2a does. Consequently, the mouse-rat heterodimer binds to Protein A but elutes at a higher pH than the mouse IgG2a homodimer, and this makes selective purification of the bispecific heterodimer possible (Lindhofer et al., 1995, J. Immunol. 155(1): 219-25). The resulting bispecific heterodimer is fully non-human, hence highly immunogenic, which could have deleterious side effects (e.g., "HAMA" or "HARA" reactions), and/or neutralize the therapeutic. There remained a need for engineered bispecifics with superior properties that can be readily produced in high yield from mammalian cell culture.

Despite the promising results obtained using heteroconjugates or bispecific antibodies produced from cell fusions as cited above, several factors made them impractical for large scale therapeutic applications. Such factors include: rapid clearance of heteroconjugates in vivo, the laboratory intensive techniques required for generating either type of molecule, the need for extensive purification of heteroconjugates away from homoconjugates or mono-specific antibodies, and the generally low yields obtained.

Genetic engineering has been used with increasing frequency to design, modify, and produce antibodies or antibody derivatives with a desired set of binding properties and effector functions. A variety of recombinant methods have been developed for efficient production of BsAbs, both as antibody fragments (Carter et al., 1995, *J. Hematother.* 4(5): 463-70; Pluckthun et al., 1997, *Immunotechnology* 3(2): 83-105; Todorovska et al., 2001, *J. Immunol. Methods* 248(1-2): 47-66) and full length IgG formats (Carter, 2001, *J. Immunol. Methods* 248(1-2): 7-15).

Combining two different scFvs results in BsAb formats with minimal molecular mass, termed sc-BsAbs or Ta-scFvs (Mack et al., 1995, *Proc. Natl. Acad. Sci. U.S.A.* 92(15): 7021-25; Mallender et al., 1994, *J. Biol. Chem.* 269(1): 199-206). BsAbs have been constructed by genetically fusing two scFvs to a dimerization functionality such as a leucine zipper (Kostelny et al., 1992, *J. Immunol.* 148(5): 1547-53; de Kruif et al., 1996, *J. Biol. Chem.* 271(13): 7630-34).

Diabodies are small bivalent and bispecific antibody fragments. The fragments comprise a $V_H$ connected to a $V_L$ on the same polypeptide chain, by using a linker that is too short (less than 12 amino acid residues) to allow pairing between the two domains on the same chain. The domains are forced to pair intermolecularly with the complementary domains of another chain and create two antigen-binding sites. These dimeric antibody fragments, or "diabodies," are bivalent and bispecific (Holliger et al., 1993, *Proc. Natl. Acad. Sci. U.S.A.* 90(14): 6444-48). Diabodies are similar in size to a Fab fragment. Polypeptide chains of $V_H$ and $V_L$ domains joined with a linker of between 3 and 12 amino acid residues form predominantly dimers (diabodies), whereas with a linker of between 0 and 2 amino acid residues, trimers (triabodies) and tetramers (tetrabodies) predominate. In addition to the linker length, the exact pattern of oligomerization seems to depend on the composition as well as the orientation of the variable domains (Hudson et al., 1999, *J. Immunol. Methods* 231(1-2): 177-89). The predictability of the final structure of diabody molecules is very poor.

Although sc-BsAb and diabody-based constructs display interesting clinical potential, it was shown that such non-covalently associated molecules are not sufficiently stable under physiological conditions. The overall stability of a scFv fragment depends on the intrinsic stability of the $V_L$ and $V_H$ domains as well as on the stability of the domain interface. Insufficient stability of the $V_H$-$V_L$ interface of scFv fragments has often been suggested as a main cause of irreversible scFv inactivation, since transient opening of the interface, which would be allowed by the peptide linker, exposes hydrophobic patches that favor aggregation and therefore instability and poor production yield (Wörn et al., 2001, *J. Mol. Biol.* 305(5): 989-1010).

An alternative method of manufacturing bispecific bivalent antigen-binding proteins from $V_H$ and $V_L$ domains is described in U.S. Pat. No. 5,989,830. Such double head and dual Fv configurations are obtained by expressing a bicistronic vector, which encodes two polypeptide chains. In the Dual-Fv configuration, the variable domains of two different antibodies are expressed in a tandem orientation on two separate chains (one heavy chain and one light chain), wherein one polypeptide chain has two times a $V_H$ in series separated by a peptide linker ($V_{H1}$-linker-$V_{H2}$) and the other polypeptide chain consists of complementary $V_L$ domains connected in series by a peptide linker ($V_{L1}$-linker-$V_{L2}$). In the cross-over double head configuration, the variable domains of two different antibodies are expressed in a tandem orientation on two separate polypeptide chains (one heavy chain and one light chain), wherein one polypeptide chain has two times a $V_H$ in series separated by a peptide linker ($V_{H1}$-linker-$V_{H2}$) and the other polypeptide chain consists of complementary $V_L$ domains connected in series by a peptide linker in the opposite orientation ($V_{L2}$-linker-$V_{L1}$). Molecular modeling of the constructs suggested the linker size to be long enough to span 30-40 Å (15-20 amino acid residues).

Increasing the valency of an antibody is of interest as it enhances the functional affinity of that antibody due to the avidity effect. Polyvalent protein complexes (PPC) with an increased valency are described in U.S. Patent Application Publication No. US 2005/0003403 A1. PPCs comprise two polypeptide chains generally arranged laterally to one another. Each polypeptide chain typically comprises three or four "v-regions," which comprise amino acid sequences capable of forming an antigen binding site when matched with a corresponding v-region on the opposite polypeptide chain. Up to about six "v-regions" can be used on each polypeptide chain. The v-regions of each polypeptide chain are connected linearly to one another and may be connected by interspersed linking regions. When arranged in the form of the PPC, the v-regions on each polypeptide chain form individual antigen binding sites. The complex may contain one or several binding specificities.

A strategy was proposed by Carter et al. (Ridgway et al., 1996, *Protein Eng.* 9(7): 617-21; Carter, 2011, *J. Immunol. Methods* 248(1-2): 7-15) to produce a Fc heterodimer using a set of "knob-into-hole" mutations in the $C_{H3}$ domain of Fc. These mutations lead to the alteration of residue packing complementarity between the $C_{H3}$ domain interface within the structurally conserved hydrophobic core so that formation of the heterodimer is favored as compared with homodimers, which achieves good heterodimer expression from mammalian cell culture. Although the strategy led to higher heterodimer yield, the homodimers were not completely suppressed (Merchant et al., 1998, *Nat. Biotechnol.* 16(7): 677-81.

Gunasekaran et al. explored the feasibility of retaining the hydrophobic core integrity while driving the formation of Fc heterodimer by changing the charge complementarity at the $C_{H3}$ domain interface (Gunasekaran et al., 2010, *J. Biol. Chem.* 285(25): 19637-46). Taking advantage of the electrostatic steering mechanism, these constructs showed efficient promotion of Fc heterodimer formation with minimum contamination of homodimers through mutation of two pairs of peripherally located charged residues. In contrast to the knob-into-hole design, the homodimers were evenly suppressed due to the nature of the electrostatic repulsive mechanism, but not totally avoided.

Davis et al. describe an antibody engineering approach to convert Fc homodimers into heterodimers by interdigitating β-strand segments of human IgG and IgA $C_{H3}$ domains, without the introduction of extra interchain disulfide bonds (Davis et al., 2010, *Protein Eng. Des. Sel.* 23(4): 195-202). Expression of SEEDbody (Sb) fusion proteins by mammalian cells yields Sb heterodimers in high yield that are readily purified to eliminate minor by-products.

U.S. Patent Application Publication No. US 2010/331527 A1 describes a bispecific antibody based on heterodimerization of the $C_{H3}$ domain, introducing in one heavy chain the mutations H95R and Y96F within the $C_{H3}$ domain. These amino acid substitutions originate from the $C_{H3}$ domain of the IgG3 subtype and will heterodimerize with an IgG1 backbone. A common light chain prone to pair with every heavy chain is a prerequisite for all formats based on heterodimerization though the $C_{H3}$ domain. A total of three types of antibodies are therefore produced: 50% having a pure IgG1 backbone, one-third having a pure H95R and Y96F mutated backbone, and one-third having two different heavy chains (bispecific). The desired heterodimer can be purified from this mixture because its binding properties to Protein A are different from those of the parental antibodies: IgG3-derived $C_{H3}$ domains do not bind to Protein A, whereas the IgG1 does. Consequently, the heterodimer binds to Protein A, but elutes at a higher pH than the pure IgG1 homodimer, and this makes selective purification of the bispecific heterodimer possible.

U.S. Pat. No. 7,612,181 describes a Dual-Variable-Domain IgG (DVD-IgG) bispecific antibody that is based on the Dual-Fv format described in U.S. Pat. No. 5,989,830. A similar bispecific format was also described in U.S. Patent Application Publication No. US 2010/0226923 A1. The addition of constant domains to respective chains of the Dual-Fv ($C_{H1}$-Fc to the heavy chain and kappa or lambda constant domain to the light chain) led to functional bispecific antibodies without any need for additional modifications (i.e., obvious addition of constant domains to enhance stability). Some of the antibodies expressed in the DVD-Ig/TBTI format show a position effect on the second (or innermost) antigen binding position (Fv2). Depending on the sequence and the nature of the antigen recognized by the Fv2 position, this antibody domain displays a reduced affinity to its antigen (i.e., loss of on-rate in comparison to the parental antibody). One possible explanation for this observation is that the linker between $V_{L1}$ and $V_{L2}$ protrudes into the CDR region of Fv2, making the Fv2 somewhat inaccessible for larger antigens.

The second configuration of a bispecific antibody fragment described in U.S. Pat. No. 5,989,830 is the cross-over double head (CODH), having the following orientation of variable domains expressed on two chains:

$V_{L1}$-linker-$V_{L2}$, for the light chain, and
$V_{H2}$-linker-$V_{H1}$, for the heavy chain The '830 patent discloses that a bispecific cross-over double-head antibody fragment (construct GOSA.E) retains higher binding activity than a Dual-Fv (see page 20, lines 20-50 of the '830 patent), and further discloses that this format is less impacted by the linkers that are used between the variable domains (see page 20-21 of the '830 patent).

SUMMARY OF THE INVENTION

The invention provides an antibody-like binding protein comprising four polypeptide chains that form four antigen binding sites, wherein two polypeptide chains have a structure represented by the formula:

$$V_{L1}\text{-}L_1\text{-}V_{L2}\text{-}L_2\text{-}C_L \quad [I]$$

and two polypeptide chains have a structure represented by the formula:

$$V_{H2}\text{-}L_3\text{-}V_{H1}\text{-}L_4\text{-}C_{H1}\text{-}Fc \quad [II]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$, $C_{H3}$ immunoglobulin heavy chain constant domains;
$L_1$, $L_2$, $L_3$, and $L_4$ are amino acid linkers;
and wherein the polypeptides of formula I and the polypeptides of formula II form a cross-over light chain-heavy chain pair.

The invention also provides an antibody-like binding protein comprising two polypeptide chains that form two antigen binding sites, wherein a first polypeptide chain has a structure represented by the formula:

$$V_{L1}\text{-}L_1\text{-}V_{L2}\text{-}L_2\text{-}C_L \quad [I]$$

and a second polypeptide chain has a structure represented by the formula:

$$V_{H2}\text{-}L_3\text{-}V_{H1}\text{-}L_4\text{-}C_{H1} \quad [II]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
$L_1$, $L_2$, $L_3$, and $L_4$ are amino acid linkers;
and wherein the first and second polypeptides form a cross-over light chain-heavy chain pair.

The invention further provides a method of making an antibody-like binding protein comprising four polypeptide chains that form four antigen binding sites, comprising identifying a first antibody variable domain that binds a first target antigen and a second antibody variable domain that binds a second target antigen, each containing a $V_L$, and a $V_H$; assigning either the light chain or the heavy chain as template chain; assigning the $V_L$ of the first antibody variable domain or the second antibody variable domain as $V_{L1}$; assigning a $V_{L2}$, a $V_{H1}$, and a $V_{H2}$ according to formulas [I] and [III] below:

$$V_{L1}\text{-}L_1\text{-}V_{L2}\text{-}L_2\text{-}C_L \quad [I]$$

$$V_{H2}\text{-}L_3\text{-}V_{H1}\text{-}L_4\text{-}C_{H1}\text{-}Fc \quad [II]$$

determining maximum and minimum lengths for $L_1$, $L_2$, $L_3$, and $L_4$; generating the polypeptide structures of formulas I and II; selecting polypeptide structures of formulas I and II that bind the first target antigen and the second target antigen when combined to form the antibody-like binding protein; wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$, $C_{H3}$ immunoglobulin heavy chain constant domains; and
$L_1$, $L_2$, $L_3$, and $L_4$ are amino acid linkers;
and wherein the polypeptides of formula I and the polypeptides of formula II form a cross-over light chain-heavy chain pair.

The invention further provides a method of making an antibody-like binding protein comprising four polypeptide chains that form four antigen binding sites, comprising identifying a first antibody variable domain that binds a first target antigen and a second antibody variable domain that binds a second target antigen, each containing a $V_L$, and a $V_H$; assigning either the light chain or the heavy chain as template chain; assigning the $V_L$ of the first antibody variable domain or the second antibody variable domain as $V_{L1}$; assigning a $V_{L2}$, a $V_{H1}$, and a $V_{H2}$ according to formulas [I] and [II] below:

$$V_{L1}\text{-}L_1\text{-}V_{L2}\text{-}L_2\text{-}C_L \qquad [I]$$

$$V_{H2}\text{-}L_3\text{-}V_{H1}\text{-}L_4\text{-}C_{H1}\text{-}Fc \qquad [II]$$

determining maximum and minimum lengths for $L_1$, $L_2$, $L_3$, and $L_4$; generating polypeptide structures of formulas I and II; selecting polypeptide structures of formulas I and II that bind the first target antigen and the second target antigen when combined to form the antibody-like binding protein; wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{H2}$ is a second immunoglobulin heavy chain variable domain;

$C_L$ is an immunoglobulin light chain constant domain;

$C_{H1}$ is the immunoglobulin $C_{H1}$ heavy chain constant domain; and $L_1$, $L_2$, $L_3$, and $L_4$ are amino acid linkers;

and wherein the polypeptides of formula I and the polypeptides of formula II form a cross-over light chain-heavy chain pair.

Specific embodiments of the invention will become evident from the following more detailed description of certain embodiments and the claims.

DETAILED DESCRIPTION OF THE INVENTION

Figure 1:
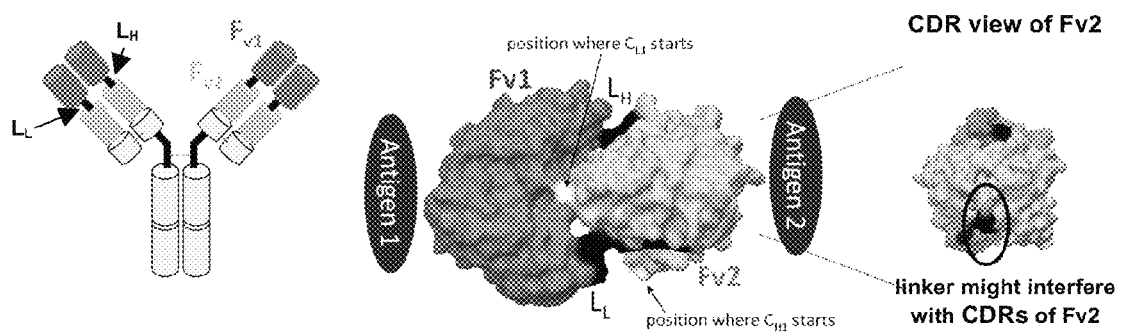
FIG. 1. Schematic representation of the antigen binding domains Fv1 and Fv2 within the dual V region configuration and arrangement of their respective peptide linkers $L_L$ and $L_H$ in the TBTI format.

The invention provides antibody-like binding proteins comprising four polypeptide chains that form four antigen binding sites, wherein each pair of polypeptides forming an antibody-like binding protein possesses dual variable domains having a cross-over orientation. The invention also provides methods for making such antigen-like binding proteins.

Computer modeling predicted that the cross-over double-head (CODH) design of U.S. Pat. No. 5,989,830 would yield a complex in which both binding sites face in the opposite direction, without the restraints suggested for the Dual-Fv configuration of U.S. Pat. No. 7,612,181. In particular, computer modeling indicated that the length of the amino acid linkers between the variable domains was not critical for the CODH design, but was important for permitting full access to both antigen binding sites in the Dual-Fv design. As with the DVD-Ig/TBTI format, antibody-like binding protein constructs were prepared in which constant domains were attached to the CODH configuration to form antibody-like binding proteins comprising four polypeptide chains that form four antigen binding sites, wherein each pair of polypeptides forming an antibody-like binding protein possesses dual variable domains having a cross-over orientation (i.e., CODH-Ig). CODH-Ig molecules are expected to possess significantly improved stability as compared with CODH molecules (as DVD-Ig/TBTI possessed improved stability over Dual-Fv molecules).

In order to test the above hypothesis, a CODH-Ig molecule was prepared using the anti-IL4 and anti-IL13 antibody sequences described in U.S. Patent Application Publication No. US 2010/0226923 A1. The CODH-Ig molecule differed from the CODH molecule of US 2010/0226923 with respect to the lengths of amino acid linkers separating the variable domains on the respective polypeptide chains. The CODH-Ig molecules were expressed in cells following transient transfection and were then purified by Protein A chromatography. Although their size-exclusion chromatography (SEC) profiles showed aggregation levels of 5-10%, none of the CODH-Ig molecules were functional, and thus none of the CODH-Ig molecules was able to bind all of its target antigens. The lack of antigen binding activity may have been due to a perturbed dimerization of the Fv-regions of the heavy and light chains due to unsuitable linker lengths compromising correct paratope formation. As a result, a protocol was developed to identify suitable amino acid linkers for insertion between the two variable domains and the second variable domain and constant domain on both the heavy and light polypeptide chains of an antibody-like binding protein. This protocol was based on protein-protein docking of homology and experimental models of the FvIL4 and FvIL13 regions, respectively, inclusion of the Fc1 domain the model, and construction of appropriate linkers between the FvIL4 and FvIL13 regions and between the Fv and constant Fc1 regions.

Standard recombinant DNA methodologies are used to construct the polynucleotides that encode the polypeptides which form the antibody-like binding proteins of the invention, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Similarly, conventional techniques may be used for chemical syntheses, chemical analyses, pharmaceutical preparation, formulation, delivery, and treatment of patients.

1. GENERAL DEFINITIONS

As utilized in accordance with the present disclosure, the following terms, unless otherwise indicated, shall be understood to have the following meanings. Unless otherwise required by context, singular terms shall include pluralities and plural terms shall include the singular.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which by virtue of its origin the isolated polynucleotide: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

The term "human antibody" as used herein includes antibodies having variable and constant regions substantially corresponding to human germline immunoglobulin sequences. In some embodiments, human antibodies are produced in non-human mammals, including, but not limited to, rodents, such as mice and rats, and lagomorphs, such as rabbits. In other embodiments, human antibodies are produced in hybridoma cells. In still other embodiments, human antibodies are produced recombinantly.

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "native Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc" as used herein is generic to the monomeric, dimeric, and multimeric forms.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

The term "antibody-like binding protein" as used herein refers to a non-naturally occurring (or recombinant) molecule that specifically binds to at least one target antigen, and which comprises four polypeptide chains that form four antigen binding sites, wherein two polypeptide chains have a structure represented by the formula:

$$V_{L1}\text{-}L_1\text{-}V_{L2}\text{-}L_2\text{-}C_L \quad [\text{I}]$$

and two polypeptide chains have a structure represented by the formula:

$$V_{H2}\text{-}L_3\text{-}V_{H1}\text{-}L_4\text{-}C_{H1}\text{-}Fc \quad [\text{II}]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$, $C_{H3}$ immunoglobulin heavy chain constant domains;
$L_1$, $L_2$, $L_3$, and $L_4$ are amino acid linkers;
and wherein the polypeptides of formula I and the polypeptides of formula II form a cross-over light chain-heavy chain pair. The term "antibody-like binding protein" as used herein also refers to a non-naturally occurring (or recombinant) molecule that specifically binds to at least one target antigen, and which comprises two polypeptide chains that form two antigen binding sites, wherein a first polypeptide chain has a structure represented by the formula:

$$V_{L1}\text{-}L_1\text{-}V_{L2}\text{-}L_2\text{-}C_L \quad [\text{I}]$$

and a second polypeptide chain has a structure represented by the formula:

$$V_{H2}\text{-}L_3\text{-}V_{H1}\text{-}L_4\text{-}C_{H1}\text{-}Fc \quad [\text{II}]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
$L_1$, $L_2$, $L_3$, and $L_4$ are amino acid linkers;
and wherein the first and second polypeptides form a cross-over light chain-heavy chain pair. A "recombinant" molecule is one that has been prepared, expressed, created, or isolated by recombinant means.

One embodiment of the invention provides antibody-like binding proteins having biological and immunological specificity to between one and four target antigens. Another embodiment of the invention provides nucleic acid molecules comprising nucleotide sequences encoding polypeptide chains that form such antibody-like binding proteins. Another embodiment of the invention provides expression vectors comprising nucleic acid molecules comprising nucleotide sequences encoding polypeptide chains that form such antibody-like binding proteins. Yet another embodiment of the invention provides host cells that express such antibody-like binding proteins (i.e., comprising nucleic acid molecules or vectors encoding polypeptide chains that form such antibody-like binding proteins).

The term "swapability" as used herein refers to the interchangeability of variable domains within the CODV format and with retention of folding and ultimate binding affinity. "Full swapability" refers to the ability to swap the order of both $V_{H1}$ and $V_{H2}$ domains, and therefore the order of $V_{L1}$ and $V_{L2}$ domains, in a CODV-Ig (i.e., to reverse the order) or CODV-Fab while maintaining full functionality of the antibody-like binding protein as evidenced by the retention of binding affinity. Furthermore, it should be noted that the designations $V_H$ and $V_L$ within a particular CODV-Ig or CODV-Fab refer only to the domain's location on a particular protein chain in the final format. For example, $V_{H1}$ and $V_{H2}$ could be derived from $V_{L1}$ and $V_{L2}$ domains in parent antibodies and placed into the $V_{H1}$ and $V_{H2}$ positions in the antibody-like binding protein. Likewise, $V_{L1}$ and $V_{L2}$ could be derived from $V_{H1}$ and $V_{H2}$ domains in parent antibodies and placed in the $V_{H1}$ and $V_{H2}$ positions in the antibody-like binding protein. Thus, the $V_H$ and $V_L$ designations refer to the present location and not the original location in a parent antibody. $V_H$ and $V_L$ domains are therefore "swappable."

An "isolated" antibody-like binding protein is one that has been identified and separated and/or recovered from a component of its natural environment. Contaminant components of its natural environment are materials that would interfere with diagnostic or therapeutic uses for the antibody-like binding protein, and may include enzymes, hormones, and other proteinaceous or non-proteinaceous solutes. In preferred embodiments, the antibody-like binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody-like binding proteins include the antibody-like binding protein in situ within recombinant cells since at least one component of the antibody-like binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The term "antigen" or "target antigen" as used herein refers to a molecule or a portion of a molecule that is capable of being bound by an antibody-like binding protein, and additionally is capable of being used in an animal to produce antibodies capable of binding to an epitope of that antigen. A target antigen may have one or more epitopes. With respect to each target antigen recognized by an antibody-like binding protein, the antibody-like binding protein is capable of competing with an intact antibody that recognizes the target antigen. A "bivalent" antibody-like binding protein, other than a "multispecific" or "multifunctional" antibody-like binding protein, is understood to comprise antigen binding sites having identical antigenic specificity.

A bispecific or bifunctional antibody typically is an artificial hybrid antibody having two different heavy chain/light chain pairs and two different binding sites or epitopes. Bispecific antibodies may be produced by a variety of methods including, but not limited to, fusion of hybridomas or linking of F(ab') fragments.

A F(ab) fragment typically includes one light chain and the $V_H$ and $C_{H1}$ domains of one heavy chain, wherein the $V_H$-$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a F(ab')$_2$ molecule.

The phrases "biological property," "biological characteristic," and the term "activity" in reference to an antibody-like binding protein of the invention are used interchangeably herein and include, but are not limited to, epitope affinity and specificity, ability to antagonize the activity of the antigen target (or targeted polypeptide), the in vivo stability of the antibody-like binding protein, and the immunogenic properties of the antibody-like binding protein. Other identifiable biological properties or characteristics of an antibody-like binding protein include, for example, cross-reactivity, (i.e., with non-human homologs of the antigen target, or with other antigen targets or tissues, generally), and ability to preserve high expression levels of protein in mammalian cells. The aforementioned properties or characteristics can be observed or measured using art-recognized techniques including, but not limited to ELISA, competitive ELISA, surface plasmon resonance analysis, in vitro and in vivo neutralization assays, and immunohistochemistry with tissue sections from different sources including human, primate, or any other source as the need may be.

The term "immunologically functional immunoglobulin fragment" as used herein refers to a polypeptide fragment that contains at least the CDRs of the immunoglobulin heavy or light chains from which the polypeptide fragment was derived. An immunologically functional immunoglobulin fragment is capable of binding to a target antigen.

A "neutralizing" antibody-like binding protein as used herein refers to a molecule that is able to block or substantially reduce an effector function of a target antigen to which it binds. As used herein, "substantially reduce" means at least about 60%, preferably at least about 70%, more preferably at least about 75%, even more preferably at least about 80%, still more preferably at least about 85%, most preferably at least about 90% reduction of an effector function of the target antigen.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or antibody-like binding protein. In certain embodiments, an antibody-like binding protein is said to specifically bind an antigen when it preferentially recognizes its target antigen in a complex mixture of proteins and/or macromolecules. In preferred embodiments, an antibody-like binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of an antibody-like binding protein can be determined, for example, by surface plasmon resonance. Generally, surface plasmon resonance analysis measures real-time binding interactions between ligand (a target antigen on a biosensor matrix) and analyte (an antibody-like binding protein in solution) by surface plasmon resonance (SPR) using the BIAcore system (Pharmacia Biosensor; Piscataway, N.J.). Surface plasmon analysis can also be performed by immobilizing the analyte (antibody-like binding protein on a biosensor matrix) and presenting the ligand (target antigen). The term "$K_D$," as used herein refers to the dissociation constant of the interaction between a particular antibody-like binding protein and a target antigen.

The term "specifically binds" as used herein refers to the ability of an antibody-like protein or an antigen-binding fragment thereof to bind to an antigen containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers described herein are referred to as $L_1$, which is located on the light chain between the N-terminal $V_{L1}$ and $V_{L2}$ domains; $L_2$, which is also on the light chain is located between the $V_{L2}$ and C-terminal $C_L$ domains. The heavy chain linkers are known as $L_3$, which is located between the N-terminal $V_{H2}$ and $V_{H1}$ domains; and $L_4$, which is located between the $V_{H1}$ and $C_{H1}$-Fc domains. The linkers $L_1$, $L_2$, $L_3$, and $L_4$ are independent, but they may in some cases have the same sequence and/or length.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the invention is intended to include other forms of expression vectors, such as viral vectors (e.g., replication defective retroviruses, adenoviruses, and adeno-associated viruses), which serve equivalent functions.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription, and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the antibody-like binding proteins of the invention, including bacterial, yeast, baculoviral, and mammalian expression systems (as well as phage display expression systems). An example of a suitable bacterial expression vector is pUC19. To express an antibody-like binding protein recombinantly, a host cell is transformed or transfected with one or more recombinant expression vectors carrying DNA fragments encoding the polypeptide chains of the antibody-like binding protein such that the polypeptide chains are expressed in the host cell and, preferably, secreted into the medium in which the host cells are cultured, from which medium the antibody-like binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids such as α-, α-disubstituted amino acids, N-alkyl amino acids, lactic acid, and other unconventional amino acids may also be suitable components for the polypeptide chains of the antibody-like binding proteins of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
 (1) hydrophobic: Met, Ala, Val, Leu, Ile, Phe, Trp, Tyr, Pro;
 (2) polar hydrophilic: Arg, Asn, Asp, Gln, Glu, His, Lys, Ser, Thr;
 (3) aliphatic: Ala, Gly, Ile, Leu, Val, Pro;
 (4) aliphatic hydrophobic: Ala, Ile, Leu, Val, Pro;
 (5) neutral hydrophilic: Cys, Ser, Thr, Asn, Gln;
 (6) acidic: Asp, Glu;
 (7) basic: His, Lys, Arg;
 (8) residues that influence chain orientation: Gly, Pro;
 (9) aromatic: His, Trp, Tyr, Phe; and
 (10) aromatic hydrophobic: Phe, Trp, Tyr.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid residues. Non-conservative substitutions may involve the exchange of a member of one of these classes for a member from another class.

A skilled artisan will be able to determine suitable variants of the polypeptide chains of the antibody-like binding proteins of the invention using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects.

A "disorder" is any condition that would benefit from treatment using the antibody-like binding proteins of the invention. "Disorder" and "condition" are used interchangeably herein and include chronic and acute disorders or diseases, including those pathological conditions that predispose a patient to the disorder in question.

The terms "treatment" or "treat" as used herein refer to both therapeutic treatment and prophylactic or preventative measures. Those in need of treatment include those having the disorder as well as those prone to have the disorder or those in which the disorder is to be prevented.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of an antibody-like binding protein.

The terms "effective amount" and "therapeutically effective amount" when used in reference to a pharmaceutical composition comprising one or more antibody-like binding proteins refer to an amount or dosage sufficient to produce a desired therapeutic result. More specifically, a therapeutically effective amount is an amount of an antibody-like binding protein sufficient to inhibit, for some period of time, one or more of the clinically defined pathological processes associated with the condition being treated. The effective amount may vary depending on the specific antibody-like binding protein that is being used, and also depends on a variety of factors and conditions related to the patient being treated and the severity of the disorder. For example, if the antibody-like binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the invention provides a pharmaceutical composition comprising a pharmaceutically acceptable carrier and a therapeutically effective amount of an antibody-like binding protein.

2. ANTIBODY-LIKE BINDING PROTEINS

In one embodiment of the invention, the antibody-like binding proteins comprise four polypeptide chains that form four antigen binding sites, wherein two polypeptide chains have a structure represented by the formula:

$$V_{L1}\text{-}L_1\text{-}V_{L2}\text{-}L_2\text{-}C_L \qquad [I]$$

and two polypeptide chains have a structure represented by the formula:

$$V_{H2}\text{-}L_3\text{-}V_{H1}\text{-}L_4\text{-}C_{H1}\text{-}Fc \qquad [II]$$

wherein:
 $V_{L1}$ is a first immunoglobulin light chain variable domain;
 $V_{L2}$ is a second immunoglobulin light chain variable domain;
 $V_{H1}$ is a first immunoglobulin heavy chain variable domain;
 $V_{H2}$ is a second immunoglobulin heavy chain variable domain;
 $C_L$ is an immunoglobulin light chain constant domain;
 $C_{H1}$ is the immunoglobulin $C_{H1}$ heavy chain constant domain;
 Fc is the immunoglobulin hinge region and $C_{H2}$, $C_{H3}$ immunoglobulin heavy chain constant domains;
 $L_1$, $L_2$, $L_3$, and $L_4$ are amino acid linkers;
and wherein the polypeptides of formula I and the polypeptides of formula II form a cross-over light chain-heavy chain pair.

In another embodiment of the invention, the antibody-like binding proteins comprise two polypeptide chains that form two antigen binding sites, wherein a first polypeptide chain has a structure represented by the formula:

$$V_{L1}\text{-}L_1\text{-}V_{L2}\text{-}L_2\text{-}C_L \qquad [I]$$

and a second polypeptide chain has a structure represented by the formula:

$$V_{H2}\text{-}L_3\text{-}V_{H1}\text{-}L_4\text{-}C_{H1}\text{-}Fc \qquad [II]$$

wherein:
 $V_{L1}$ is a first immunoglobulin light chain variable domain;
 $V_{L2}$ is a second immunoglobulin light chain variable domain;
 $V_{H1}$ is a first immunoglobulin heavy chain variable domain;
 $V_{H2}$ is a second immunoglobulin heavy chain variable domain;
 $C_L$ is an immunoglobulin light chain constant domain;
 $C_{H1}$ is the immunoglobulin $C_{H1}$ heavy chain constant domain;
 $L_1$, $L_2$, $L_3$, and $L_4$ are amino acid linkers; and wherein the first and second polypeptides form a cross-over light chain-heavy chain pair.

The antibody-like binding proteins of the invention may be prepared using domains or sequences obtained or derived from any human or non-human antibody, including, for example, human, murine, or humanized antibodies.

In some antibody-like binding proteins of the invention, the length of $L_3$ is at least twice the length of $L_1$. In other antibody-like binding proteins of the invention, the length of $L_4$ is at least twice the length of $L_2$. In some antibody-like binding proteins of the invention, the length of $L_1$ is at least twice the length of $L_3$. In other antibody-like binding proteins of the invention, the length of $L_2$ is at least twice the length of $L_4$.

In some antibody-like binding proteins of the invention, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In other antibody-like binding proteins, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In a preferred antibody-like binding protein, $L_1$ is 7 amino acid residues in length, $L_2$ is 5 amino acid residues in length, $L_3$ is 1 amino acid residues in length, and $L_4$ is 2 amino acid residues in length.

In some antibody-like binding proteins of the invention, $L_1$ is 1 to 3 amino acid residues in length, $L_2$ is 1 to 4 amino acid residues in length, $L_3$ is 2 to 15 amino acid residues in length, and $L_4$ is 2 to 15 amino acid residues in length. In other antibody-like binding proteins, $L_1$ is 1 to 2 amino acid residues in length, $L_2$ is 1 to 2 amino acid residues in length, $L_3$ is 4 to 12 amino acid residues in length, and $L_4$ is 2 to 12 amino acid residues in length. In a preferred antibody-like binding protein, $L_1$ is 1 amino acid residue in length, $L_2$ is 2 amino acid residues in length, $L_3$ is 7 amino acid residues in length, and $L_4$ is 5 amino acid residues in length.

In some antibody-like binding proteins of the invention, $L_1$, $L_3$, or $L_4$ may be equal to zero. However, in antibody-like binding proteins wherein $L_1$, $L_3$, or $L_4$ is equal to zero, the corresponding transition linker between the variable region and constant region or between the dual variable domains on the other chain cannot be zero. In some embodiments, $L_1$ is equal to zero and $L_3$ is 2 or more amino acid residues, $L_3$ is equal to zero and $L_1$ is equal to 1 or more amino acid residues, or $L_4$ is equal to 0 and $L_2$ is 3 or more amino acid residues.

In some antibody-like binding proteins of the invention, at least one of the linkers selected from the group consisting of $L_1$, $L_2$, $L_3$, and $L_4$ contains at least one cysteine residue.

Examples of suitable linkers include a single glycine (Gly) residue; a diglycine peptide (Gly-Gly); a tripeptide (Gly-Gly-Gly); a peptide with four glycine residues (Gly-Gly-Gly-Gly; SEQ ID NO: 25); a peptide with five glycine residues (Gly-Gly-Gly-Gly-Gly; SEQ ID NO: 26); a peptide with six glycine residues (Gly-Gly-Gly-Gly-Gly-Gly; SEQ ID NO: 27); a peptide with seven glycine residues (Gly-Gly-Gly-Gly-Gly-Gly-Gly; SEQ ID NO: 28); a peptide with eight glycine residues (Gly-Gly-Gly-Gly-Gly-Gly-Gly-Gly; SEQ ID NO: 29). Other combinations of amino acid residues may be used such as the peptide Gly-Gly-Gly-Gly-Ser (SEQ ID NO: 30) and the peptide Gly-Gly-Gly-Gly-Ser-Gly-Gly-Gly-Gly-Ser (SEQ ID NO: 31). Other suitable linkers include a single Ser, and Val residue; the dipeptide Arg-Thr, Gln-Pro, Ser-Ser, Thr-Lys, and Ser-Leu; Thr-Lys-Gly-Pro-Ser (SEQ ID NO: 52), Thr-Val-Ala-Ala-Pro (SEQ ID NO: 53), Gln-Pro-Lys-Ala-Ala (SEQ ID NO: 54), Gln-Arg-Ile-Glu-Gly (SEQ ID NO: 55); Ala-Ser-Thr-Lys-Gly-Pro-Ser (SEQ ID NO: 48), Arg-Thr-Val-Ala-Ala-Pro-Ser (SEQ ID NO: 49), Gly-Gln-Pro-Lys-Ala-Ala-Pro (SEQ ID NO: 50), and His-Ile-Asp-Ser-Pro-Asn-Lys (SEQ ID NO: 51). The examples listed above are not intended to limit the scope of the invention in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the antibody-like binding proteins of the invention (see Example 12).

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In some antibody-like binding proteins of the invention, $V_{L1}$ comprises the amino acid sequence of SEQ ID NO: 1; $V_{L2}$ comprises the amino acid sequence of SEQ ID NO: 3; $V_{H1}$ comprises the amino acid sequence of SEQ ID NO: 2; and $V_{H2}$ comprises the amino acid sequence of SEQ ID NO: 4.

In some embodiments of the invention, the antibody-like binding protein is capable of specifically binding one or more antigen targets. In preferred embodiments of the invention, the antibody-like binding protein is capable of specifically binding at least one antigen target selected from the group consisting of B7.1, B7.2, BAFF, BlyS, C3, C5, CCL11 (eotaxin), CCL15 (MIP-1d), CCL17 (TARC), CCL19 (MIP-3b), CCL2 (MCP-1), CCL20 (MIP-3a), CCL21 (MIP-2), SLC, CCL24 (MPIF-2/eotaxin-2), CCL25 (TECK), CCL26 (eotaxin-3), CCL3 (MIP-1a), CCL4 (MIP-1b), CCL5 (RANTES), CCL7 (MCP-3), CCL8 (mcp-2), CD3, CD19, CD20, CD24, CD40, CD40L, CD80, CD86, CDH1 (E-cadherin), Chitinase, CSF1 (M-CSF), CSF2 (GM-CSF), CSF3 (GCSF), CTLA4, CX3CL1 (SCYD1), CXCL12 (SDF1), CXCL13, EGFR, FCER1A, FCER2, HER2, IGF1R, IL-1, IL-12, IL13, IL15, IL17, IL18, IL1A, IL1B, IL1F10, IL1β, IL2, IL4, IL6, IL7, IL8, IL9, IL12/23, IL22, IL23, IL25, IL27, IL35, ITGB4 (b 4 integrin), LEP (leptin), MHC class II, TLR2, TLR4, TLR5, TNF, TNF-a, TNFSF4 (OX40 ligand), TNFSF5 (CD40 ligand), Toll-like receptors, TREM1, TSLP, TWEAK, XCR1 (GPR5/CCXCR1), DNGR-1 (CLEC91), and HMGB1. In other embodiments of the invention, the antibody-like binding protein is capable of inhibiting the function of one or more of the antigen targets.

In some embodiments of the invention, the antibody-like binding protein is bispecific and capable of binding two different antigen targets or epitopes. In a preferred embodiment of the invention, the antibody-like binding protein is bispecific and each light chain-heavy chain pair is capable of binding two different antigen targets or epitopes. In a more preferred embodiment, the antibody-like binding protein is capable of binding two different antigen targets that are selected from the group consisting of IL4 and IL13, IGF1R and HER2, IGF1R and EGFR, EGFR and HER2, BK and IL13, PDL-1 and CTLA-4, CTLA4 and MHC class II, IL-12 and IL-18, IL-1α and IL-1β, TNFα and IL12/23, TNFα and IL-12p40, TNFα and IL-1β, TNFα and IL-23, and IL17 and IL23. In an even more preferred embodiment, the antibody-like binding protein is capable of binding the antigen targets IL4 and IL13.

In some embodiments of the invention, the antibody-like binding protein specifically binds IL4 with an on-rate of 2.97 E+07 and an off-rate of 3.30 E-04 and specifically binds IL13 with an on-rate of 1.39 E+06 and an off-rate of 1.63 E-04. In other embodiments of the invention, the antibody-like binding protein specifically binds IL4 with an on-rate of 3.16 E+07 and an off-rate of 2.89 E-04 and specifically binds IL13 with an on-rate of 1.20 E+06 and an off-rate of 1.12 E-04.

In one embodiment of the invention, an antibody-like binding protein comprising four polypeptide chains that form four antigen binding sites is prepared by identifying a first antibody variable domain that binds a first target antigen and a second antibody variable domain that binds a second target antigen, each containing a $V_L$, and a $V_H$; assigning either the light chain or the heavy chain as template chain; assigning the $V_L$ of the first antibody variable domain or the second antibody variable domain as $V_{L1}$; assigning a $V_{L2}$, a $V_{H1}$, and a $V_{H2}$ according to formulas [I] and [II] below:

$$V_{L1}\text{-}L_1\text{-}V_{L2}\text{-}L_2\text{-}C_L \quad [\text{I}]$$

$$V_{H2}\text{-}L_3\text{-}V_{H1}\text{-}L_4\text{-}C_{H1}\text{-}Fc \quad [\text{II}]$$

determining maximum and minimum lengths for $L_1$, $L_2$, $L_3$, and $L_4$; generating polypeptide structures of formulas I and II; selecting polypeptide structures of formulas I and II that bind the first target antigen and the second target antigen when combined to form the antibody-like binding protein; wherein:

$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$, $C_{H3}$ immunoglobulin heavy chain constant domains; and
$L_1$, $L_2$, $L_3$, and $L_4$ are amino acid linkers;

and wherein the polypeptides of formula I and the polypeptides of formula II form a cross-over light chain-heavy chain pair.

In another embodiment of the invention, an antibody-like binding protein comprising four polypeptide chains that form four antigen binding sites is prepared by identifying a first antibody variable domain that binds a first target antigen and a second antibody variable domain that binds a second target antigen, each containing a $V_L$, and a $V_H$; assigning either the light chain or the heavy chain as template chain; assigning the $V_L$ of the first antibody variable domain or the second antibody variable domain as $V_{L1}$; assigning a $V_{L2}$, a $V_{H1}$, and a $V_{H2}$ according to formulas [I] and [II] below:

$$V_{L1}\text{-}L_1\text{-}V_{L2}\text{-}L_2\text{-}C_L \quad [\text{I}]$$

$$V_{H2}\text{-}L_3\text{-}V_{H1}\text{-}L_4\text{-}C_{H1}\text{-}Fc \quad [\text{II}]$$

determining maximum and minimum lengths for $L_1$, $L_2$, $L_3$, and $L_4$; generating polypeptide structures of formulas I and II; selecting polypeptide structures of formulas I and II that bind the first target antigen and the second target antigen when combined to form the antibody-like binding protein; wherein:

$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain; and
$L_1$, $L_2$, $L_3$, and $L_4$ are an amino acid linkers;

and wherein the polypeptides of formula I and the polypeptides of formula II form a cross-over light chain-heavy chain pair.

In other embodiments of the invention, an antibody-like binding protein in which the first antibody variable domain and the second antibody variable domain are the same is prepared.

One embodiment of the invention provides a method for making an antibody-like binding protein, comprising expressing in a cell one or more nucleic acid molecules encoding polypeptides having structures represented by the formulas [I] and [II] below:

$$V_{L1}\text{-}L_1\text{-}V_{L2}\text{-}L_2\text{-}C_L \quad [\text{I}]$$

$$V_{H2}\text{-}L_3\text{-}V_{H1}\text{-}L_4\text{-}C_{H1}\text{-}Fc \quad [\text{II}]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain;
Fc is the immunoglobulin hinge region and $C_{H2}$, $C_{H3}$ immunoglobulin heavy chain constant domains; and
$L_1$, $L_2$, $L_3$, and $L_4$ are amino acid linkers;

and wherein the polypeptides of formula I and the polypeptides of formula II form a cross-over light chain-heavy chain pair.

Another embodiment of the invention provides a method for making an antibody-like binding protein, comprising expressing in a cell one or more nucleic acid molecules encoding polypeptides having structures represented by the formulas [I] and [II] below:

$$V_{L1}\text{-}L_1\text{-}V_{L2}\text{-}L_2\text{-}C_L \quad [\text{I}]$$

$$V_{H2}\text{-}L_3\text{-}V_{H1}\text{-}L_4\text{-}C_{H1}\text{-}Fc \quad [\text{II}]$$

wherein:
$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is the immunoglobulin $C_{H1}$ heavy chain constant domain; and
$L_1$, $L_2$, $L_3$, and $L_4$ are amino acid linkers;

and wherein the polypeptide of formula I and the polypeptide of formula II form a cross-over light chain-heavy chain pair.

3. USES FOR ANTIBODY-LIKE BINDING PROTEINS

The antibody-like binding proteins of the invention can be employed in any known assay method, such as competitive binding assays, direct and indirect sandwich assays, and immunoprecipitation assays for the detection and quantitation of one or more target antigens. The antibody-like binding proteins will bind the one or more target antigens with an affinity that is appropriate for the assay method being employed.

For diagnostic applications, in certain embodiments, antibody-like binding proteins can be labeled with a detectable moiety. The detectable moiety can be any one that is capable of producing, either directly or indirectly, a detectable signal. For example, the detectable moiety can be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase.

The antibody-like binding proteins of the invention are also useful for in vivo imaging. An antibody-like binding protein labeled with a detectable moiety can be administered to an animal, preferably into the bloodstream, and the presence and location of the labeled antibody in the host assayed. The antibody-like binding protein can be labeled with any moiety that is detectable in an animal, whether by nuclear magnetic resonance, radiology, or other detection means known in the art.

The invention also relates to a kit comprising an antibody-like binding protein and other reagents useful for detecting target antigen levels in biological samples. Such reagents can include a detectable label, blocking serum, positive and negative control samples, and detection reagents.

4. ANTIBODY-LIKE BINDING PROTEIN THERAPEUTIC COMPOSITIONS AND ADMINISTRATION THEREOF

Therapeutic or pharmaceutical compositions comprising antibody-like binding proteins are within the scope of the invention. Such therapeutic or pharmaceutical compositions can comprise a therapeutically effective amount of an antibody-like binding protein, or antibody-like binding protein-drug conjugate, in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the antibody-like binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the invention, antibody-like binding protein compositions can be prepared for storage by mixing the selected composition having the desired degree of purity with optional formulation agents in the form of a lyophilized cake or an aqueous solution. Further, the antibody-like binding protein can be formulated as a lyophilizate using appropriate excipients such as sucrose.

The pharmaceutical compositions of the invention can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired antibody-like binding protein in a pharmaceutically acceptable vehicle. A particularly suitable vehicle for parenteral injection is sterile distilled water in which an antibody-like binding protein is formulated as a sterile, isotonic solution, properly preserved. Yet another preparation can involve the formulation of the desired molecule with an agent, such as injectable microspheres, bioerodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, an antibody-like binding protein can be formulated as a dry powder for inhalation. Antibody-like binding protein inhalation solutions can also be formulated with a propellant for aerosol delivery. In yet another embodiment, solutions can be nebulized.

It is also contemplated that certain formulations can be administered orally. In one embodiment of the invention, antibody-like binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the antibody-like binding protein. Diluents, flavorings, low melting point waxes, vegetable oils, lubricants, suspending agents, tablet disintegrating agents, and binders can also be employed.

Another pharmaceutical composition can involve an effective quantity of antibody-like binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the invention will be evident to those skilled in the art, including formulations involving antibody-like binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions of the invention to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The invention also encompasses kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of an antibody-like binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the antibody-like binding protein is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg.

Dosing frequency will depend upon the pharmacokinetic parameters of the antibody-like binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

5. EXAMPLES

The Examples that follow are illustrative of specific embodiments of the invention, and various uses thereof. They are set forth for explanatory purposes only, and should not be construed as limiting the scope of the invention in any way.

Example 1

Design and Engineering of Bispecific Cross-Over Dual Variable Region Antibody-Like Binding Proteins The cross-over dual variable region in an Fv format was described in U.S. Pat. No. 5,989,830 and was referred to as a cross-over double head (CODH) configuration. Molecular modeling predicted that the cross-over double-head (CODH) design results in a complex with both binding sites facing in opposite directions, without the restraints suggested for the Dual-Fv configuration. The CODH Fv format was examined to determine whether it could be converted into complete antibody-like molecules by adding a $C_L$ domain to the light chain and an Fc region to the heavy chain. A similar conversion was successful for the corresponding dual variable domains (DVD-Ig) and TBTI as described in U.S. Pat. No.

7,612,181 and International Publication No. WO 2009/052081. The arrangement of the variable regions in the CODH format is shown in the structures below, which indicate the amino to carboxyl orientation of the peptide chains:

(a) light chain: $NH_2$-$V_{L1}$-Linker-$V_{L2}$-COOH
(b) heavy chain: $NH_2$-$V_{H2}$-Linker-$V_{H1}$-COOH The amino to carboxyl terminal arrangement of the variable regions in (a) and (b) above can be distinguished from the arrangement in the Dual-Fv configuration shown in (c) and (d) below:

(c) light chain: $NH_2$-$V_{L1}$-Linker-$V_{L2}$-COOH
(d) heavy chain: $NH_2$-$V_{H1}$-Linker-$V_{H2}$-COOH The main difference to note is the distinct placement of the corresponding light chain and heavy chain variable regions ($V_{H1}/V_{L1}$ and $V_{H2}/V_{L2}$) with respect to each other in the two dual variable region configurations. The corresponding $V_{L1}$ and $V_{H1}$ domains were both at the N-terminus of the light and heavy chains in dual variable region configuration. In contrast, in the cross-over configuration, one half of one pair of an antibody variable region was separated spatially within the protein chain in the cross-over configuration. In the cross-over configuration, the $V_{L1}$ domain would be at the N-terminus of the protein light chain but the pairing $V_{H1}$ domain is at the C-terminus of the cross-over configuration heavy chain. The spatial relationship between $V_{L1}$ and $V_{H1}$ found in the dual variable region configuration is the arrangement found in natural antibodies.

One potential disadvantage of the dual Fv configuration is that the linker $L_L$ separating the two variable regions protrudes into the antigen binding site of the Fv2 domain (see FIG. 1). This protrusion may interfere with antigen binding and result in a perturbed accessibility of Antigen 2 to Fv2. This perturbed accessibility or interference may prevent antigen binding. In addition, this interference might be more pronounced where the size of Antigen 2 is larger. Indeed, it has been documented in U.S. Pat. No. 7,612,181 that the binding affinity and neutralization ability of a DVD-Ig molecule depends on which antigen specificity is presented at the N-terminus or C-terminus. See U.S. Pat. No. 7,612,181, Example 2.

Therefore, to create more stable antibody-like binding proteins that are not subject to loss of antigen affinity as compared to the parental antibody, cross-over dual variable region molecules having a $C_L$ domain on the light chain and an Fc region on the heavy chain were designed and constructed. The polypeptides that form these antibody-like proteins have the structures shown below, in which the amino to carboxyl terminal orientation of the polypeptide chains is indicated:

(e) light chain: $NH_2$-$V_{L1}$-Linker-$V_{L2}$-$C_L$-COOH
(f) heavy chain: $NH_2$-$V_{H2}$-Linker-$V_{H1}$-$C_{H1}$-Fc-COOH To evaluate whether this bispecific antibody-like protein design would bind to two different antigens, two previously generated and humanized variable regions from antibodies specific for IL4 (parental humanized anti-IL4) and IL13 (parental humanized anti-IL13) were used to construct the bispecific antibody-like molecules shown in Table 1. Sequencing of the mouse antibodies and the humanization process were described in International Publication No. WO 2009/052081 (TBTI). Briefly, amino acid sequences of the variable heavy and light chains of the murine anti-IL13 clone B-B13 and the murine anti-IL4 clone 8D4-8 were determined by amino acid sequencing. The murine sequences were humanized and then back-translated into nucleotide sequences as described in Example 5 of International Publication No. WO 2009/052081, which is incorporated herein by reference in its entirety. The parental humanized anti-IL4 $V_H$ and $V_L$, and parental humanized anti-IL13 $V_H$ and $V_L$ sequences were combined and arranged as shown in Table 1. The shorthand codes in column one of Table 1 were created to simplify discussion of these antibody-like binding proteins. The antibody-like binding proteins differ in the size of the linker inserted between the two variable regions as shown in Table 1. DNA molecules encoding the polypeptides shown in Table 1 were generated from the back-translated parental anti-IL4 and anti-IL13 antibodies. $C_{H1}$, $C_L$, and Fc domains were obtained from IGHG1 (GenBank Accession No. 569F4) and IGKC (GenBank Accession No. Q502W4).

TABLE 1

Cross-over Double Head Immunoglobulins

| | Protein Description | SEQ ID NO: |
|---|---|---|
| Shorthand Code for Protein | | |
| Parental anti-IL4 Light Chain | anti-IL4 $V_L$ | 1 |
| Parental anti-IL4 Heavy Chain | anti-IL4 $V_H$ | 2 |
| Parental anti-IL13 Light Chain | anti-IL13 $V_L$ | 3 |
| Parental anti-IL13 Heavy Chain | anti-IL13 $V_H$ | 4 |
| Heavy Chain Codes | | |
| IL13(G4S)IL4CH1-Fc | anti-IL13 $V_H$-(G4S)-anti-IL4 $V_H$-$C_{H1}$-Fc | 5 |
| IL13(G4S2)IL4CH1-Fc | anti-IL13 $V_H$-(G4S)$_2$-anti-IL4 $V_H$-$C_{H1}$-Fc | 6 |
| IL4(G4S)IL13CH1-Fc | anti-IL4 $V_H$-(G4S)-anti-IL13 $V_H$-$C_{H1}$-Fc | 7 |
| IL4(G4S2)IL13CH1-Fc | anti-IL4 $V_H$-(G4S)$_2$-anti-IL13 $V_H$-$C_{H1}$-Fc | 8 |
| Light Chain Codes | | |
| IL13(G4S)IL4CL | anti-IL13 $V_L$-(G4S)-anti-IL4 $V_L$-CL | 9 |
| IL13(G4S2)IL4CL | anti-IL13 $V_L$-(G4S)$_2$-anti-IL4 $V_L$-CL | 10 |
| IL4(G4S)IL13CL | anti-IL4 $V_L$-(G4S)-anti-IL13 $V_L$-CL | 11 |
| IL4(G4S2)IL13CL | anti-IL4 $V_L$-(G4S)$_2$-anti-IL13 $V_L$-CL | 12 |

The protein combinations shown in Table 2 were expressed by transient transfection and purified by Protein A chromatography. In each case, size exclusion chromatography revealed less than 12% aggregation, with most having less than 7% aggregation; but none of the cross-over double head immunoglobulins were found to display any ability to bind either IL4 or IL13. However, no functional antibody-like binding could be detected and the reasons for this lack of activity could not be ascertained. It was previously predicted that this arrangement would show superior stability over the dual variable region domain antibodies described in U.S. Pat. No. 7,612,181 and International Publication No. WO 2009/052081.

TABLE 2

Binding of CODH-Ig to IL4 and IL13

| Protein Combination | Aggregation | IL4 binding | IL13 binding |
|---|---|---|---|
| anti-IL13 $V_H$-(G4S)-anti-IL4 $V_H$-$C_{H1}$-Fc<br>anti-IL4 $V_L$-(G4S)-anti-IL13 $V_L$-$C_L$ | 5.4% | ND* | ND |
| anti-IL13 $V_H$-(G4S)-anti-IL4 $V_H$-$C_{H1}$-Fc<br>anti-IL4 $V_L$-(G4S)$_2$-anti-IL13 $V_L$-CL | 6.3% | ND | ND |
| anti-IL13 $V_H$-(G4S)$_2$-anti-IL4 $V_H$-$C_{H1}$-Fc<br>anti-IL4 $V_L$-(G4S)-anti-IL13 $V_L$-CL | 11.5% | ND | ND |
| anti-IL13 $V_H$-(G4S)$_2$-anti-IL4 $V_H$-$C_{H1}$-Fc<br>anti-IL4 $V_L$-(G4S)$_2$-anti-IL13 $V_L$-CL | 10.1% | ND | ND |

TABLE 2-continued

Binding of CODH-Ig to IL4 and IL13

| Protein Combination | Aggregation | IL4 binding | IL13 binding |
|---|---|---|---|
| anti-IL4 V$_H$-(G$_4$S)-anti-IL13 V$_H$-C$_{H1}$-Fc anti-IL13 V$_L$-(G$_4$S)-anti-IL4 V$_L$-CL | 2.7% | ND | ND |
| anti-IL4 V$_H$-(G$_4$S)-anti-IL13 V$_H$-C$_{H1}$-Fc anti-IL13 V$_L$-(G$_4$S)$_2$-anti-IL4 V$_L$-CL | 3.6% | ND | ND |
| anti-IL4 V$_H$-(G$_4$S)$_2$-anti-IL13 V$_H$-C$_{H1}$-Fc anti-IL13 V$_L$-(G$_4$S)-anti-IL4 V$_L$-CL | 2.9% | ND | ND |
| anti-IL4 V$_H$-(G$_4$S)$_2$-anti-IL13 V$_H$-C$_{H1}$-Fc anti-IL13 V$_L$-(G$_4$S)$_2$-anti-IL4 V$_L$-CL | 10.8% | ND | ND |

*ND means none detected

Example 2

Design of CODV-Ig Proteins by Molecular Modeling

Figure 2:
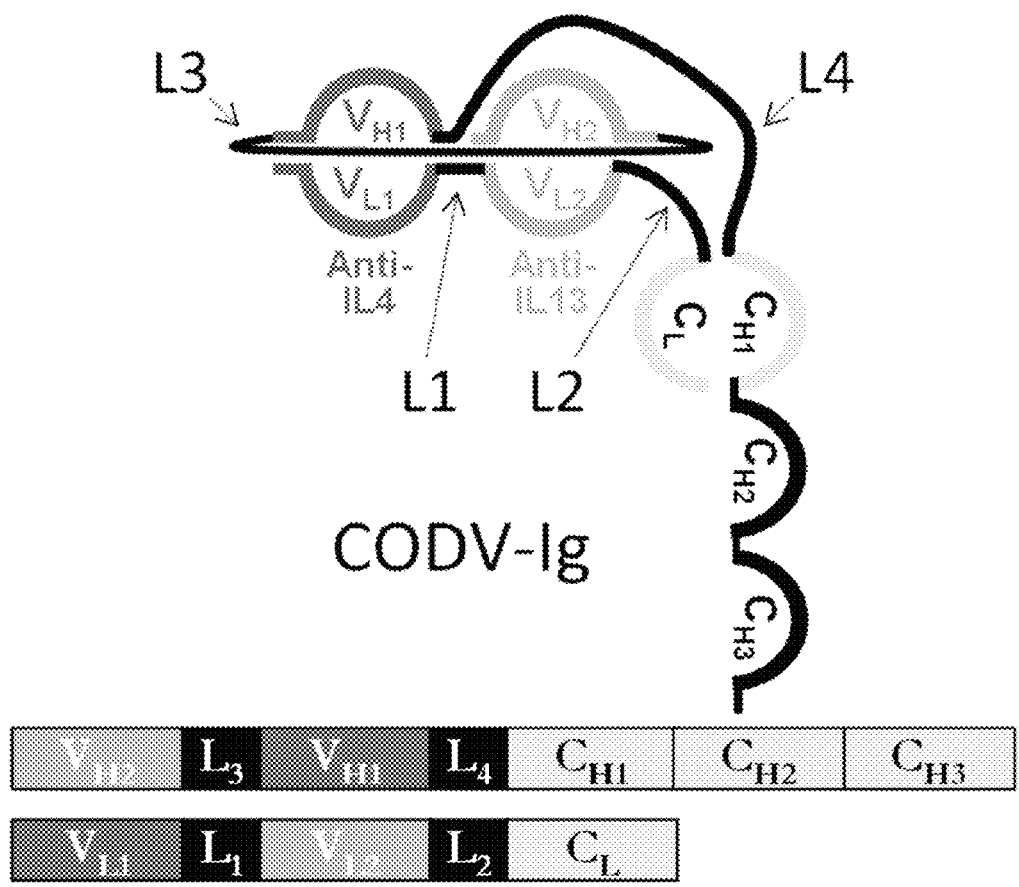
FIG. 2. Schematic diagram (2D) of the antigen binding domains Fv1 (anti-IL4) and Fv2 (anti-IL13) within the cross-over dual variable (CODV) configuration and the arrangement of their respective peptide linkers.

To obtain fully functional antibody-like proteins utilizing the cross-over double head configuration that are amendable to incorporation of the Fc and C$_{L1}$ domains, a molecular modeling protocol was developed for the inclusion and evaluation of different linkers between the constant and variable domains and between the dual variable domains on both the heavy and light chains. The question was whether the addition of unique linkers between each constant/variable domain interface and between the two variable/variable domain interfaces on both the heavy and light chains would allow proper protein folding to occur and produce functional antibody-like molecules in the cross-over dual variable region configuration (see FIG. 2). In other words, a total of four independent and unique linkers were evaluated (see FIG. 2). This molecular modeling protocol was based on protein-protein docking of homology models and experimental models of the Fv$_{IL4}$ and Fv$_{IL13}$ regions, respectively, in combination with appropriate linkers between the Fv$_{IL4}$ and Fv$_{IL13}$ regions and between the Fv and constant or Fc regions.

The independent linkers were assigned unique names as follows: L$_1$ refers to the linker between N-terminal V$_L$ and the C-terminal V$_L$ on the light chain; L$_2$ refers to the linker between the C-terminal V$_L$ and C$_L$ on the light chain; L$_3$ refers to the linker between N-terminal V$_H$ and the C-terminal V$_H$ on the heavy chain; L$_4$ refers to the linker between the C-terminal V$_H$ and C$_{H1}$ (and Fc) on the heavy chain. It should be noted that the designations V$_H$ and V$_L$ refer only to the domain's location on a particular protein chain in the final format. For example, V$_{H1}$ and V$_{H2}$ could be derived from V$_{L1}$ and V$_{L2}$ domains in parent antibodies and placed into the V$_{H1}$ and V$_{H2}$ positions in a CODV-Ig. Likewise, V$_{L1}$ and V$_{L2}$ could be derived from V$_{H1}$ and V$_{H2}$ domains in parent antibodies and placed into the V$_{H1}$ and V$_{H2}$ positions in a CODV-Ig. Thus, V$_H$ and V$_L$ designations refer to present location and not the original location in a parent antibody.

In more detail, a homology model of Fv$_{IL4}$ was constructed on PDB entries 1YLD (light chain) and 1IQW (heavy chain). The Fv$_{IL4}$ dimer was recomposed on an in-house crystal structure of the IL13/anti-IL13 Fab$_{IL13}$ complex and optimized. In order to obtain an estimate of the volume required by IL4 when bound to Fv$_{IL4}$, the crystal structure of IL4 (1RCB.pdb) was docked to the homology model of Fv$_{IL4}$. Next, twenty-two putative models of the complex were generated that merited further consideration.

Figure 3:
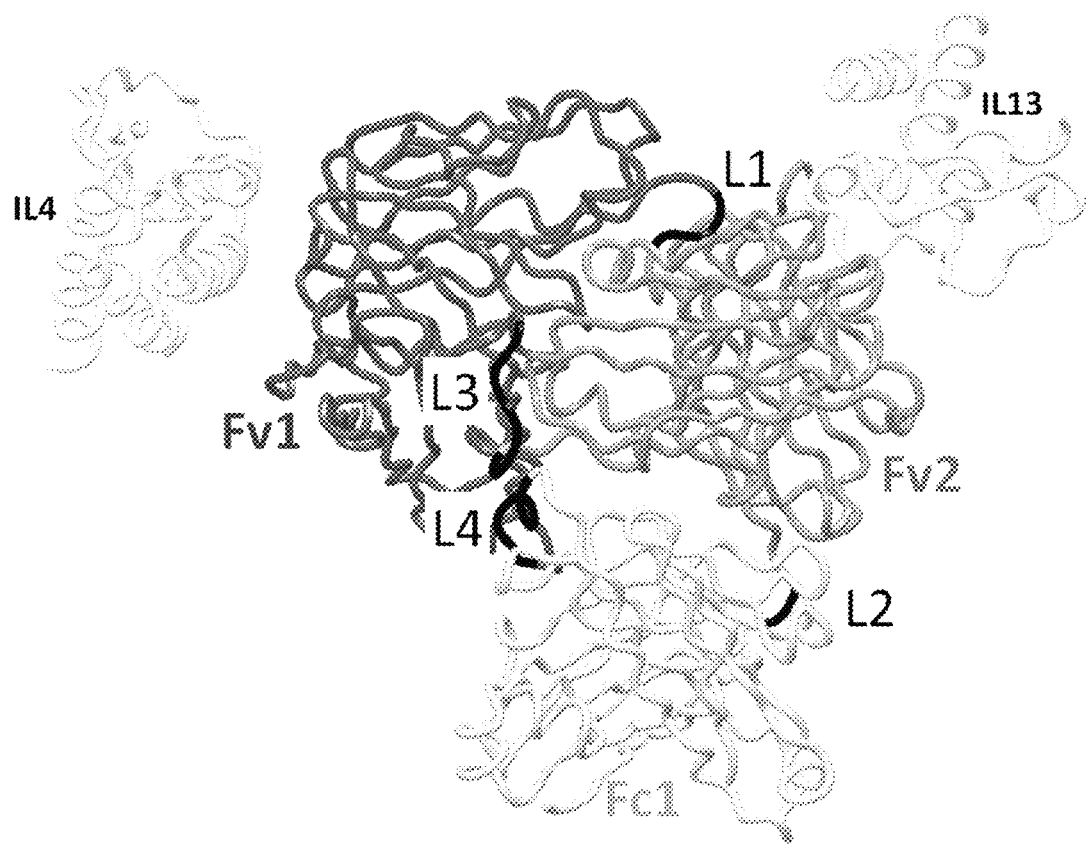
FIG. 3. Schematic representation of the Fv anti-IL4 and Fab anti-IL13 showing one possible spatial arrangement obtained by protein-protein docking of Fv of anti-IL4 and the Fv of anti-IL13.
Figure 4:
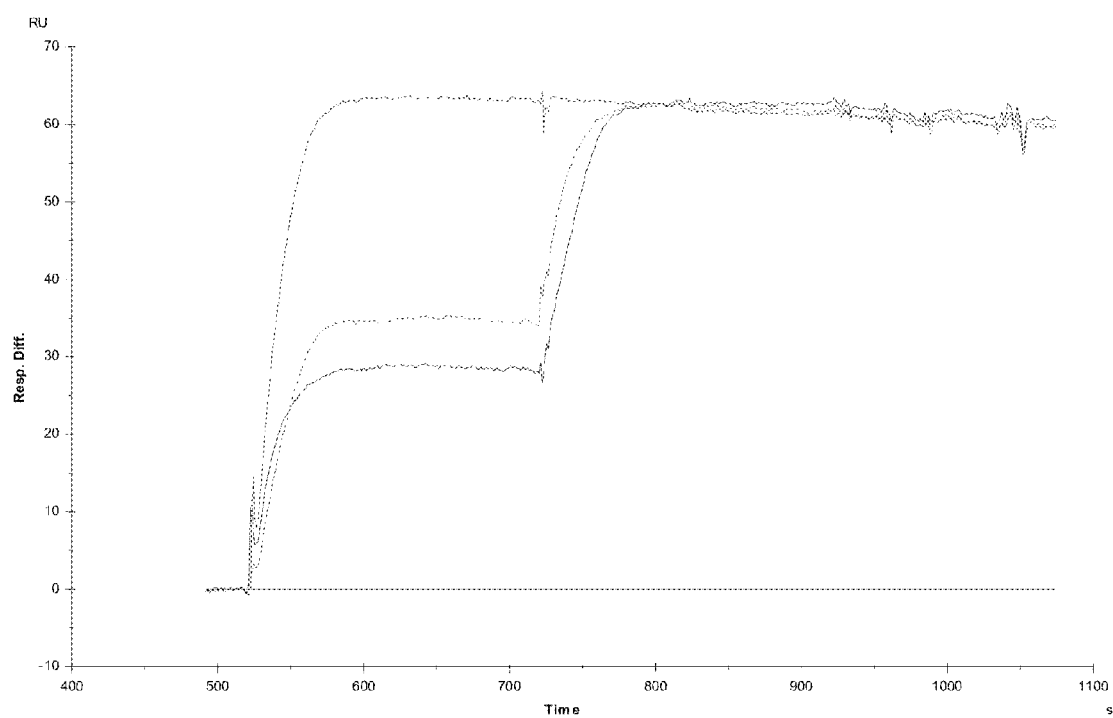
FIG. 4. Assessment of tetravalent and bispecific binding ability of the CODV protein in a BIACORE assay by injecting the two antigens sequentially or simultaneously over a DVD-Ig protein-coated chip. The maximal signal observed by sequential injection can be obtained by co-injection of both antigens, demonstrating saturation of all binding sites.

In parallel, the homology model of Fv$_{IL4}$ was docked to Fv$_{IL13}$ extracted from an in-house crystal structure of the IL13/Fab$_{IL13}$ complex. One superior solution was found that permitted construction of relatively short linkers while showing no steric interference for antigen binding and placement of the constant domains as was the case for dual variable region immunoglobulins (see FIG. 3). In this arrangement Fv$_{IL4}$ (V$_{L1}$) was placed at the N-terminus of the light chain, followed by Fv$_{IL13}$ (V$_{L2}$) and Fc (C$_{L1}$) on the light chain C-terminus. On the heavy chain, Fv$_{IL13}$ (V$_{H2}$) was placed N-terminally, followed by Fv$_{IL4}$ (V$_{H1}$) and the constant regions (C$_{H1}$-C$_{H2}$-C$_{H3}$).

As shown in Table 3, the models of the light chain suggested that the linker L$_1$ between the V$_{L1}$ and V$_{L2}$ domains and the linker L$_2$ between the V$_{L2}$ and C$_{L1}$ domains should be between one to three and zero to two glycine residues long, respectively. Models of the heavy chain suggested that the linker L$_3$ between the V$_{H2}$ and V$_{H1}$ domains and the linker L$_4$ between the V$_{H1}$ and C$_{H1}$ domains should be between two to six and four to seven glycine residues long, respectively (see Table 3 and FIG. 2). In this example, glycine was used as a prototypical amino acid for the linkers but other amino acid residues may also serve as linkers. The structural stability of the proposed models was verified by optimization of the linker conformations, minimization, and molecular dynamics calculations. Systematic combination between four light chain and six heavy chain constructs resulted in 24 possible cross-over dual variable region bispecific anti-IL4 and anti-IL13 antibody-like binding proteins (see Table 4).

TABLE 3

Proposed Linker Lengths

| Linker Between | Maximal Linker Insertion | Minimal Linker Insertion | Linker Name |
|---|---|---|---|
| V$_{L1}$-V$_{L2}$ | Gly$_3$ | Gly | L$_1$ |
| V$_{L2}$-C$_L$ | Gly$_2$ | None | L$_2$ |
| V$_{H2}$-V$_{H1}$ | Gly$_6$ | Gly$_2$ | L$_3$ |
| V$_{H1}$-C$_{H1}$ | Gly$_7$ | Gly$_4$ | L$_4$ |

TABLE 4

CODV-Ig for Expression

| Code* | | SEQ ID NO: |
|---|---|---|
| Heavy Chains (N to C terminal) | | |
| HC1 | IL13 V$_H$-(Gly6)-IL4 V$_H$-(Gly7)-C$_{H1}$-Fc | 13 |
| HC2 | IL13 V$_H$-(Gly6)-IL4 V$_H$-(Gly4)-C$_{H1}$-Fc | 14 |
| HC3 | IL13 V$_H$-(Gly2)-IL4 V$_H$-(Gly7)-C$_{H1}$-Fc | 15 |
| HC4 | IL13 V$_H$-(Gly2)-IL4 V$_H$-(Gly4)-C$_{H1}$-Fc | 16 |
| HC5 | IL13 V$_H$-(Gly4)-IL4 V$_H$-(Gly7)-C$_{H1}$-Fc | 17 |
| HC6 | IL13 V$_H$-(Gly4)-IL4 V$_H$-(Gly4)-C$_{H1}$-Fc | 18 |
| Light Chains (N to C terminal) | | |
| LC1 | IL4 V$_L$-(Gly3)-IL13 V$_L$-C$_{L1}$ | 19 |
| LC2 | IL4 V$_L$-(Gly)-IL13 V$_L$-C$_{L1}$ | 20 |
| LC3 | IL4 V$_L$-(Gly3)-IL13 V$_L$-(Gly2)-C$_{L1}$ | 21 |
| LC4 | IL4 V$_L$-(Gly)-IL13 V$_L$-(Gly2)-C$_{L1}$ | 22 |
| C$_{L1}$ | C$_{L1}$ human light chain constant domain | 23 |
| C$_{H1}$-Fc | C$_{H1}$ human heavy chain constant domain and Fc region | 24 |
| Gly4 | peptide linker with 4 glycines (GGGG) | 25 |
| Gly5 | peptide linker with 5 glycines (GGGGG) | 26 |
| Gly6 | peptide linker with 6 glycines (GGGGGG) | 27 |
| Gly7 | peptide linker with 7 glycines (GGGGGGG) | 28 |
| Gly8 | peptide linker with 8 glycines (GGGG GGGG) | 29 |

*A short hand code was devised to represent the associated structures. Codes beginning with HC represent the adjacent heavy chain and codes beginning with LC represent the adjacent light chains.

In Table 4, the prefix "anti" is not included but it is intended to mean that IL13 refers to anti-IL13 and IL4 refers to anti-IL4.

Example 3

Generation of CODV-Ig Expression Plasmids

Nucleic acid molecules encoding the variable heavy and light chains of the six heavy chains and four light chains described in Table 4 were generated by gene synthesis at Geneart (Regensburg, Germany). The variable light chain domains were fused to the constant light chain (IGKC, GenBank Accession No. Q502W4) by digestion with the restriction endonucleases ApaLI and BsiWI and subsequently ligated into the ApaLI/BsiWI sites of the episomal expression vector pFF, an analogon of the pTT vector described by Durocher et al., (2002, *Nucl. Acids Res.* 30(2): E9), creating the mammalian expression plasmid for expression of the light chains.

The variable heavy chain domains were fused to the "Ted" variant of the human constant heavy chain (IGHG1, GenBank Accession No. 569F4), or alternatively, to a 6×His tagged $C_{H1}$ domain from the human constant IGHG1 in order to create a bispecific Fab. Next, the $V_H$ domain was digested with the restriction endonucleases ApaLI and ApaI and then fused to the IGHG1 or His tagged $C_{H1}$ domain respectively, by ligation into the ApaLI/ApaI sites of the episomal expression vector pFF, creating the mammalian expression plasmids for expression of the heavy chains (IgG1 or Fab respectively).

Example 4

Expression of CODV-Ig

The expression plasmids encoding the heavy and light chains of the corresponding constructs were propagated in *E. coli* DH5a cells. Plasmids used for transfection were prepared from *E. coli* using the Qiagen EndoFree Plasmid Mega Kit.

HEK 293-FS cells growing in Freestyle Medium (Invitrogen) were transfected with indicated LC and HC plasmids encoding the heavy chains and light chains shown in Table 4 using 293fectin (Invitrogen) transfection reagent as described by the manufacturer. After 7 days, cells were removed by centrifugation and the supernatant was passed over a 0.22 µm filter to remove particles.

CODV-IgG1 constructs were purified by affinity chromatography on Protein A columns (HiTrap Protein A HP Columns, GE Life Sciences). After elution from the column with 100 mM acetate buffer and 100 mM NaCl, pH 3.5, the CODV-IgG1 constructs were desalted using HiPrep 26/10 Desalting Columns, formulated in PBS at a concentration of 1 mg/mL and filtered using a 0.22 µm membrane.

Bispecific CODV Fab constructs were purified by IMAC on HiTrap IMAC HP Columns (GE Life Sciences). After elution from the column with a linear gradient (Elution buffer: 20 mM sodium phosphate, 0.5 M NaCl, 50-500 mM imidazole, pH 7.4), the protein containing fractions were pooled and desalted using HiPrep 26/10 Desalting Columns, formulated in PBS at a concentration of 1 mg/mL and filtered using a 0.22 µm membrane.

Protein concentration was determined by measurement of absorbance at 280 nm. Each batch was analyzed by SDS-PAGE under reducing and non-reducing conditions to determine the purity and molecular weight of each subunit and of the monomer.

A Nunc F96-MaxiSorp-Immuno plate was coated with goat anti-Human IgG (Fc specific) [NatuTec A80-104A]. The antibody was diluted to 10 µg/ml in carbonate coating buffer (50 mM sodium carbonate, pH 9.6) and dispensed at 50 µL per well. The plate was sealed with adhesive tape, and stored overnight at 4° C. The plate was washed three times with Wash buffer (PBS, pH 7.4 and 0.1% Tween20). 150 µL of blocking solution (1% BSA/PBS) was dispensed into each well to cover the plate. After 1 hour at room temperature, the plate was washed three times with Wash buffer. 100 µL of sample or standards (in a range from 1500 ng/ml to 120 ng/ml) were added and allowed to sit for 1 hour at room temperature. The plate was washed three times with Wash buffer. 100 µL of goat anti-Human IgG-FC-HRP conjugate [NatuTec A80-104P-60] diluted 1:10.000 were added using incubation solution (0.1% BSA, PBS, pH 7.4, and 0.05% Tween20). After 1 hour incubation at room temperature, the plate was washed three times with Wash buffer. 100 µL of ABTS substrate (10 mg ABTS tablet (Pierce 34026) in 0.1 M $Na_2HPO_4$, 0.05 M citric acid solution, pH 5.0). Addition of 10 µL of 30% $H_2O_2$/10 ml Substrate buffer prior to use) were dispensed to each well, and the color was allowed to develop. After the color developed (approximately 10 to 15 minutes), 50 µL of 1% SDS solution were added to stop the reaction. The plate was read at $A_{405}$.

Example 5

Characterization of CODV-Ig Variants

To determine whether the CODV-Ig antibody-like protein heavy and light chains were pairing and folding properly, the aggregation level was measured by analytical size-exclusion chromatography (SEC). Analytical SEC was performed on assembled pairs using an ÄKTA explorer 10 (GE Healthcare) equipped with a TSKgel G3000SWXL column (7.8 mm×30 cm) and TSKgel SWXL guard column (Tosoh Bioscience). The analysis was run at 1 ml/min using 250 mM NaCl, 100 mM Na-phosphate, pH 6.7, with detection at 280 nm. 30 µL of protein sample (at 0.5-1 mg/ml) were applied onto the column. For estimation of the molecular size, the column was calibrated using a gel filtration standard mixture (MWGF-1000, SIGMA Aldrich). Data evaluation was performed using UNICORN software v5.11.

Table 5 shows the results of the first set of 24 different CODV-Ig molecules made using the anti-IL4 and anti-IL13 variable region combinations described in Table 4. The codes assigned in Table 4 represent the adjacent structures shown in Table 4. For the pairs of light chain and heavy chains where protein was produced, aggregation levels were measured using SEC. The results are shown in Table 5 where LC4 ($L_1$=1; $L_2$=2) was most successful in pairing with all six heavy chains. LC4 corresponds to the structure IL4 $V_L$-(Gly)-IL13 $V_L$-(Gly2)-$C_{L1}$ having linker $L_1$ equal to 1, where a single amino acid residue separated the two $V_L$ domains of the dual variable region light chain. In addition, LC4 had $L_2$ equal to 2, which contained a Gly-Gly dipeptide linker between the central $V_L$ and the C-terminal $C_{H1}$.

TABLE 5

Levels of Aggregation Among Pairs of Heavy and Light Chains

|  | HC1 | HC2 | HC3 | HC4 | HC5 | HC6 |
| --- | --- | --- | --- | --- | --- | --- |
| LC1 | >50% | >50% | ND* | ND | ND | ND |
| LC2 | ND | ND | ND | >50% | ND | ND |

TABLE 5-continued

Levels of Aggregation Among Pairs of Heavy and Light Chains

|  | HC1 | HC2 | HC3 | HC4 | HC5 | HC6 |
|---|---|---|---|---|---|---|
| LC3 | ND | ND | ND | ND | ND | ND |
| LC4 | 7.2% | 6.8% | 6.8% | 7.1% | 6.3% | 5.9% |

*ND indicates that no protein was produced

Where CODV-Ig molecules were produced, a single-concentration BIACORE experiment at intermediate IL13 and IL4 concentrations was performed to verify binding to target antigens. CODV-Ig antibody-like molecules corresponding to the LC4:HC4 and LC4:HC6 combinations described in Table 4 were chosen for assessment of a full kinetic analysis using surface plasmon resonance.

As depicted in Table 5, most of the CODV-Ig molecules could not be produced at all or only as aggregates (up to 90%). The heavy chain/light chain combinations giving rise to acceptable aggregation levels (5-10%) after one chromatography step were the ones combined with the light chain IL4 $V_L$-(Gly)-IL13 $V_L$-(Gly2)-$C_{L1}$. The light chain was the most finicky chain within these CODV-Ig variants and served as platform to accept different heavy chains with different linker compositions.

1. Kinetic Analysis

Two pairs of heavy and light chains were selected for full kinetic analysis. Recombinant human IL13 and IL4 was purchased from Chemicon (USA). Kinetic characterization of purified antibodies was performed using surface plasmon resonance technology on a BIACORE 3000 (GE Healthcare). A capture assay using a species specific antibody (e.g., human-Fc specific MAB 1302, Chemicon) for capture and orientation of the investigated antibodies was used. The capture antibody was immobilized via primary amine groups (11000 RU) on a research grade CM5 chip (GE Life Sciences) using standard procedures. The analyzed antibody was captured at a flow rate of 10 μL/min with an adjusted RU value that would result in maximal analyte binding of 30 RU. Binding kinetics were measured against recombinant human IL4 and IL13 over a concentration range between 0 to 25 nM in HBS EP (10 mM HEPES, pH 7.4, 150 mM NaCl, 3 mM EDTA, and 0.005% Surfactant P20) at a flow rate of 30 μl/min. Chip surfaces were regenerated with 10 mM glycine, pH 2.5. Kinetic parameters were analyzed and calculated in the BIAevaluation program package v4.1 using a flow cell without captured antibody as reference.

Table 6 below shows the comparison of kinetics of the parental BB13 (anti-IL13) and 8D4 (anti-IL4) antibodies (expressed as IgGs) with the respective domains within the CODV-Ig format (Table 4, Codes LC4:HC4 and LC4:HC6). As shown in Table 6, the CODV-Ig constructs did not exhibit decreased binding properties against the corresponding antigens, when compared to the parental anti-IL13 and anti-IL4 antibodies. The loss in the on-rate observed in the DVD-Ig/TBTI format using the same Fv sequences did not occur with the CODV-Ig configuration. The opposite facing binding sites should allow for binding large antigens or bridging different cells with a bispecific antibody-like configuration, and would also be suitable for a wider selection of parental antibodies. A further advantage of the CODV-Ig was that no linker residues protrude into the antigen binding site and reduce accessibility of the antigen.

TABLE 6

| Kinetic Analysis of LC4:HC4 and LC4:HC6 | | | | |
|---|---|---|---|---|
| Code | | On-rate [1/Ms] | Off-rate [1/s] | KD [M] |
| | parental anti-IL4 mAb | 2.49E+07 | 1.95E−04 | 7.83E−12 |
| | parental anti-IL13 mAb | 1.59E+06 | 1.30E−04 | 8.18E−11 |
| LC4:HC4 | CODV-Ig with IL4 | 3.16E+07 | 2.89E−04 | 9.14E−12 |
| LC4:HC4 | CODV-IG with IL13 | 1.20E+06 | 1.12E−04 | 9.34E−11 |
| LC4:HC6 | CODV-Ig with IL4 | 2.97E+07 | 3.30E−04 | 1.11E−11 |
| LC4:HC6 | CODV-IG with IL13 | 1.39E+06 | 1.63E−04 | 1.18E−10 |

2. Co-injection of IL4 and IL13 for Demonstration of Additive Antigen Binding by CODV-Ig To investigate additive binding of both antigens, a wizard-driven co-inject method was applied in which one antigen was injected immediately followed by the other antigen after a lag time (IL4 then IL13 and vice versa). The resulting binding level could be compared to that achieved with a 1:1 mixture of both antigens in the same concentration. In order to show additive binding of both the IL4 and IL13 antigens by the CODV-Ig molecules, a BIACORE experiment was performed with a CODV-Ig combination [HC4:LC4] by co-injection of both antigens in three separate analysis cycles (see FIG. 4). The co-injection was done with 3.125 nM IL4/25 nM IL13 (and vice versa) and with a 1:1 mixture of 3.125 nM IL4 and 25 nM IL13. A co-injection of HBS-EP buffer was done as a reference. At a time point of 800 seconds, an identical binding level of 63 RU was achieved after injection of the antigen mixture or co-injection of the antigens, regardless of the co-injection sequence. When CODV-Ig protein had been saturated by the first antigen (IL4), the second antigen (IL13) was injected and a second binding signal was observed. This observation was reproduced when the antigen injection sequence was reversed. This demonstrates the additive and non-inhibition of binding of both antigens by the CODV-Ig. Therefore, the CODV-Ig construct was able to bind both antigens simultaneously (i.e., exhibit bispecificity) saturating all binding sites (i.e., exhibited tetravalency).

Example 6

Tolerance of Linker Lengths for CODV-Ig

The tolerance for linkers of various lengths was evaluated by constructing CODV-Ig molecules having different combinations of linker lengths for $L_1$, $L_2$ on the light chain and $L_3$ and $L_4$ on the heavy chain. CODV-Ig constructs were generated with heavy chain linkers $L_3$ and $L_4$ varying between 1 through 8 residues for $L_3$ and either 0 or 1 residues for $L_4$. The heavy chain contained anti-IL4 as the N-terminal binding domain and anti-IL13 as the C-terminal binding domain followed by $C_{H1}$-Fc. The light chain linkers $L_1$ and $L_2$ were varied from 3 to 12 residues for $L_1$ and from 3 to 14 residues for $L_2$. The light chain contained anti-IL13 as the N-terminal binding domain and anti-IL4 as the C-terminal binding domain followed by $C_{L1}$.

1. Characterization of CODV-Ig Variants

Determination of aggregation level was by analytical size-exclusion chromatography (SEC). Analytical SEC was performed using an ÄKTA explorer 10 (GE Healthcare) equipped with a TSKgel G3000SWXL column (7.8 mm×30 cm) and TSKgel SWXL guard column (Tosoh Bioscience). The analysis was run at 1 ml/min using 250 mM NaCl, 100 mM Na-phosphate pH 6.7, with detection at 280 nm. 30 μL of protein sample (at 0.5-1 mg/ml) was applied onto the column. For estimation of the molecular size, the column was calibrated using a gel filtration standard mixture (MWGF-1000, SIGMA Aldrich). Data evaluation was performed using UNICORN software v5.11.

Recombinant human IL13 and IL4 were purchased from Chemicon (USA). Recombinant human TNF-α was purchased from Sigma Aldrich (H8916-10 μg), recombinant human IL-1β (201-LB/CF), recombinant human IL-23 (1290-IL/CF), recombinant human EGFR (344 ER), and recombinant human HER2 (1129-ER-50) were purchased from R&D Systems.

Kinetic binding analysis by Biacore was performed as follows. Surface plasmon resonance technology on a Biacore 3000 (GE Healthcare) was used for detailed kinetic characterization of purified antibodies. A capture assay using a species-specific antibody (e.g., human-Fc specific MAB 1302, Chemicon) for capture and orientation of the investigated antibodies was used. For determination of IL4 and IL13 binding kinetics, the corresponding CODV Fabs as in Example 10, Table 12 were captured using the anti-human Fab capture Kit (GE Healthcare). The capture antibody was immobilized via primary amine groups (11000 RU) on a research grade CM5 chip (GE Life Sciences) using standard procedures. The analyzed antibody was captured at a flow rate of 10 μL/min with an adjusted RU value that would result in maximal analyte binding of 30 RU. Binding kinetics were measured against recombinant human IL4 and IL13 over a concentration range between 0 to 25 nM in HBS EP (10 mM HEPES pH 7.4, 150 mM NaCl, 3 mM EDTA, 0.005% Surfactant P20) at a flow rate of 30 μL/min. Chip surfaces were regenerated with 10 mM glycine pH 2.5. Kinetic parameters were analyzed and calculated in the BIAevaluation program package v4.1 using a flow cell without captured antibody as a reference.

Binding affinities of CODV-Ig, CODV-Fab, and TBTI against EGFR and HER2 were measured using a Proteon XPR36 protein interaction array system (Biorad). The antigens were immobilized by amine reactive coupling on GLC sensor chips (Biorad). Dilution series of the bispecific antibody variants in PBSET buffer (Biorad) were analyzed in parallel in one-shot kinetics mode with double referencing. Data were analyzed using Proteon Manager Software v3.0 (Biorad) with either Langmuir 1:1 model with mass transfer or bivalent analyte model.

Table 7 summarizes the results for yield, aggregation (as measured by size exclusion chromatography), and binding affinity for CODV-Ig having different size combinations of linkers. The results revealed that CODV-Ig molecules in which $L_2$ was zero generally could not be produced, or where protein was produced, there was a high level of aggregation (see Batch ID Nos. 101, 102, 106-111, and 132-137 in Table 7). Therefore, in contrast to the molecular modeling prediction from Example 2, where $L_2$ equal to zero was within the acceptable range, these results indicate that the $V_{L2}$-$C_L$ transition (or $L_2$) requires a linker of at least one residue (see Table 7).

TABLE 7

Optimization of Linker Sizes for CODV-Ig

| Batch ID | Alignment on LC1* | $L_1$ | $L_2$ | $L_3$ | $L_4$ | Yield[1] [mg/L] | Aggregation [%] | KD (Antigen1) IL4 [pM] | KD (Antigen2) IL13 [pM] |
|---|---|---|---|---|---|---|---|---|---|
| 101 | IL4 x IL13 | 0 | 0 | 0 | 0 | n.p. | — | — | — |
| 102 | IL4 x IL13 | 0 | 0 | 2 | 4 | 1.0 | 66.4 | 35 | 125 |
| 103 | IL4 x IL13 | 0 | 1 | 2 | 4 | 2.0 | 10.8 | 4 | 124 |
| 104 | IL4 x IL13 | 0 | 2 | 2 | 4 | 1.0 | 10.0 | 3 | 137 |
| 105 | IL4 x IL13 | 0 | 2 | 4 | 4 | 2.0 | 8.5 | 6 | 94 |
| 106 | IL4 x IL13 | 1 | 0 | 2 | 4 | 4.2 | 61.0 | — | — |
| 107 | IL4 x IL13 | 1 | 0 | 2 | 7 | n.p. | — | — | — |
| 108 | IL4 x IL13 | 1 | 0 | 4 | 4 | n.p. | — | — | — |
| 109 | IL4 x IL13 | 1 | 0 | 4 | 7 | n.p. | — | — | — |
| 110 | IL4 x IL13 | 1 | 0 | 6 | 4 | 3.0 | 75.0 | — | — |
| 111 | IL4 x IL13 | 1 | 0 | 6 | 7 | 5.6 | 91.0 | — | — |
| 112 | IL4 x IL13 | 1 | 1 | 2 | 4 | 5.3 | 8.8 | 5 | 55 |
| 113 | IL4 x IL13 | 1 | 2 | 0 | 0 | 2.0 | 1.9 | 6 | 59 |
| 114 | IL4 x IL13 | 1 | 2 | 0 | 2 | 1.0 | 7.2 | 4 | 75 |
| 115 | IL4 x IL13 | 1 | 2 | 0 | 4 | 2.0 | 8.0 | 11 | 62 |
| 116 | IL4 x IL13 | 1 | 2 | 1 | 4 | 3.0 | 5.7 | 5 | 74 |
| 117 | IL4 x IL13 | 1 | 2 | 12 | 12 | 4.0 | 9.2 | 7 | 75 |
| 118 | IL4 x IL13 | 1 | 2 | 12 | 9 | 7.0 | 11.8 | 7 | 74 |
| 119 | IL4 x IL13 | 1 | 2 | 15 | 15 | 10.0 | 7.9 | 6 | 64 |
| 120 | IL4 x IL13 | 1 | 2 | 2 | 2 | 2.0 | 5.9 | 6 | 70 |
| 121 | IL4 x IL13 | 1 | 2 | 2 | 4 | 7.0 | 7.1 | 11 | 118 |
| 122 | IL4 x IL13 | 1 | 2 | 2 | 7 | 6.6 | 6.8 | 1 | 50 |
| 123 | IL4 x IL13 | 1 | 2 | 4 | 4 | 5.8 | 5.9 | 9 | 93 |
| 124 | IL4 x IL13 | 1 | 2 | 4 | 7 | 5.6 | 6.3 | 6 | 51 |
| 125 | IL4 x IL13 | 1 | 2 | 6 | 4 | 7.6 | 6.8 | 8 | 64 |
| 126 | IL4 x IL13 | 1 | 2 | 6 | 7 | 8.2 | 7.2 | 9 | 56 |
| 127 | IL4 x IL13 | 1 | 2 | 9 | 12 | 4.0 | 8.7 | 2 | 83 |
| 128 | IL4 x IL13 | 1 | 2 | 9 | 9 | 10.2 | 14.0 | 12 | 94 |
| 129 | IL4 x IL13 | 1 | 3 | 2 | 4 | 4.0 | 4.7 | 5 | 70 |
| 130 | IL4 x IL13 | 1 | 4 | 2 | 4 | 7.1 | 6.0 | 4 | 57 |
| 131 | IL4 x IL13 | 2 | 2 | 2 | 4 | 1.0 | 7.3 | 5 | 50 |
| 132 | IL4 x IL13 | 3 | 0 | 2 | 4 | n.p. | — | — | — |
| 133 | IL4 x IL13 | 3 | 0 | 2 | 7 | n.p. | — | — | — |
| 134 | IL4 x IL13 | 3 | 0 | 4 | 4 | n.p. | — | — | — |
| 135 | IL4 x IL13 | 3 | 0 | 4 | 7 | n.p. | — | — | — |
| 136 | IL4 x IL13 | 3 | 0 | 6 | 4 | 9.8 | 93.0 | — | — |
| 137 | IL4 x IL13 | 3 | 0 | 6 | 7 | 5.8 | 90.0 | — | — |
| 138 | IL4 x IL13 | 3 | 2 | 2 | 4 | n.p. | — | — | — |

TABLE 7-continued

Optimization of Linker Sizes for CODV-Ig

| Batch ID | Alignment on LC1* | $L_1$ | $L_2$ | $L_3$ | $L_4$ | Yield[1] [mg/L] | Aggregation [%] | KD (Antigen1) IL4 [pM] | KD (Antigen2) IL13 [pM] |
|---|---|---|---|---|---|---|---|---|---|
| 139 | IL4 x IL13 | 3 | 2 | 2 | 7 | n.p. | — | — | — |
| 140 | IL4 x IL13 | 3 | 2 | 4 | 4 | n.p. | — | — | — |
| 141 | IL4 x IL13 | 3 | 2 | 4 | 7 | n.p. | — | — | — |
| 142 | IL4 x IL13 | 3 | 2 | 6 | 4 | n.p. | — | — | — |
| 143 | IL4 x IL13 | 3 | 2 | 6 | 7 | n.p. | — | — | — |

*Alignment on the heavy chain must be IL13$V_H$-$L_3$-IL4$V_H$-$L_4$-$C_{H1}$-Fc
[1] n.p. means the construct was not producible.

In addition, the CODV-Ig linker lengths described above were found to be more sensitive to increases in 1 amino acid residue than increases in 2 amino acid residues. For example, while Batch ID Nos. 103 and 104 differ by 1 amino acid residue in $L_2$, Batch ID No. 103 shows 6 fold more aggregation and Batch ID No. 104 displays less aggregation and twice the yield. In contrast, Batch ID Nos. 104 and 105, which differ by two residues in $L_2$, displayed similar profiles with respect to yield, aggregation, and binding.

Example 7

Heavy Chain as Template Chain for CODV-Ig

Figure 5:
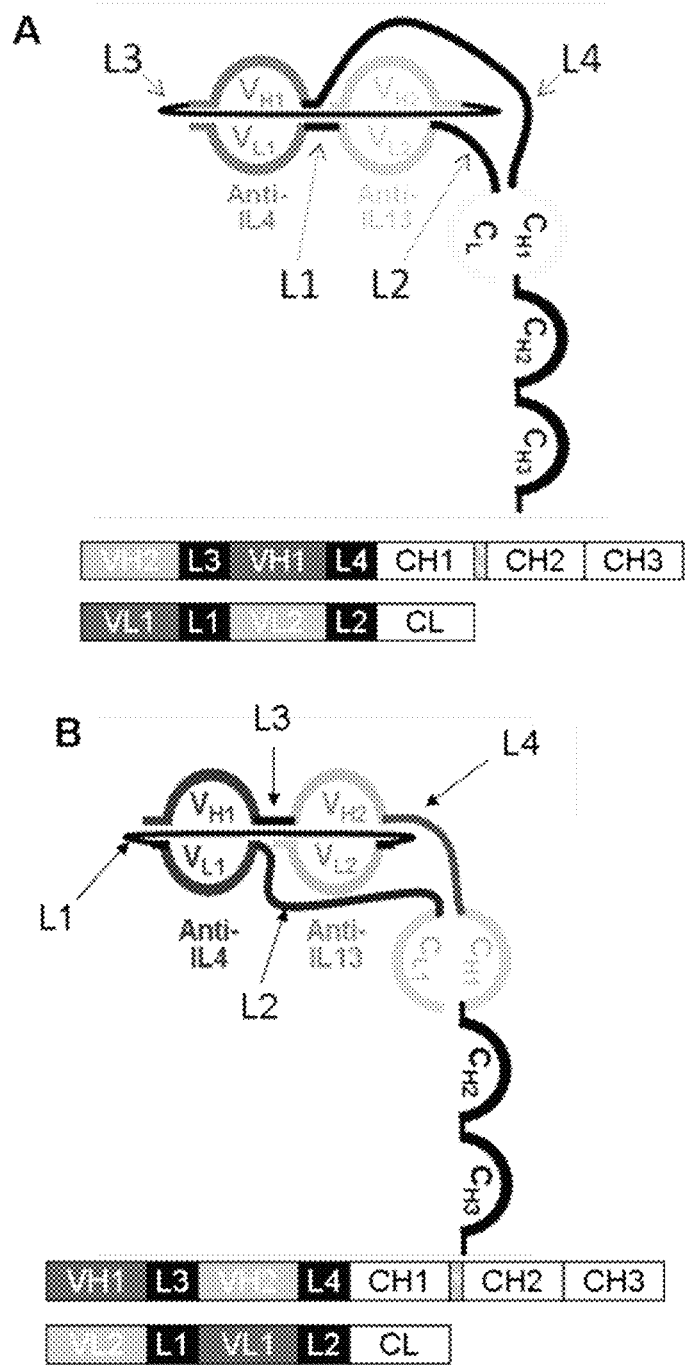
FIG. 5. Schematic diagram (2D) of the antigen binding domains within the CODV configuration and arrangement of their respective peptide linker $L_L$ ($L_1$ and $L_2$) and $L_H$ ($L_3$ and $L_4$). In panel A, the light chain is kept in a "linear or template" alignment, whereas the heavy chain is in the "cross-over" configuration. In panel B, the heavy chain is kept in a "linear or template" alignment and the light chain is in the "cross-over" configuration.

In examples 1 through 5, the optimal short linker sizes on the light chain suggested that the light chain was serving as a template by remaining in a linear arrangement and that larger linkers were required on the heavy chain in order for the heavy chain to fold properly into the cross-over configuration to conform to the template light chain (see FIG. 5, Panel A). Whether the short linkers specifically placed on the heavy chain to maintain a liner arrangement on the heavy chain rendered the heavy chain the "template" chain, and whether the pattern would repeat itself and larger linkers would be required to allow the non-template chain to fold properly and accommodate the now template heavy chain was evaluated next (see FIG. 5, Panel B).

Figure 6:
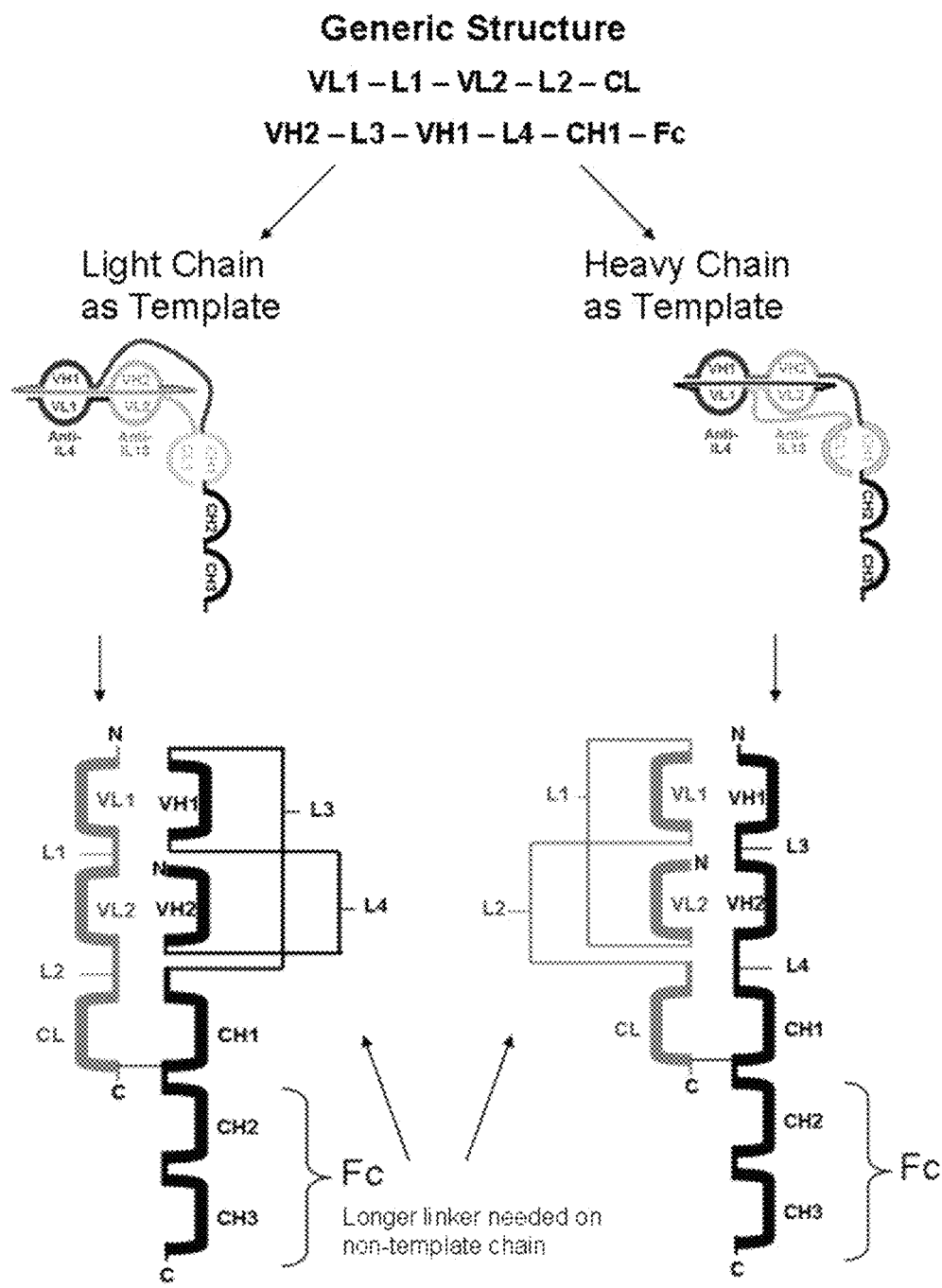
FIG. 6. Schematic representation of CODV-Ig design based on whether the light chain or heavy chain is used as "template."

FIG. 6 illustrates these principles of CODV-Ig design based on having either the light chain or the heavy chain as the "template." To evaluate the generic nature of this concept, CODV-Ig constructs were generated with heavy chain linkers $L_3$ and $L_4$ varying between 1 through 8 residues for $L_3$ and either 0 or 1 residues for $L_4$. The heavy chain contained anti-IL4 as the N-terminal binding domain and anti-IL13 as the C-terminal binding domain followed by $C_{H1}$-Fc. The light chain linkers $L_1$ and $L_2$ were varied from 3 to 12 residues for $L_1$ and from 3 to 14 residues for $L_2$. The light chain contained anti-IL13 as the N-terminal binding domain and anti-IL4 as the C-terminal binding domain followed by $C_{L1}$.

Table 8 summarizes the results for yield, aggregation (as measured by size exclusion chromatography), and binding affinity for CODV-Ig having different size combinations of linkers and where the heavy chain is maintained in a linear arrangement as the template chain and the light chain is allowed to fold in a cross-over configuration. The results revealed that CODV-Ig molecules in which $L_4$ was zero generally could not be produced, or where protein was produced, there was a high level of aggregation (similar to molecules in which $L_2$ was equal to zero) (see Batch ID Nos. 207-209, 211-212, 219-224, 231-236, 243-252, and 263-266 in Table 8). One exception was Batch ID No. 210, in which $L_1$ was 7, $L_2$ was 5, $L_3$ was 2, and $L_4$ was zero. This arrangement produced a sufficient amount of protein and had an acceptable level of aggregation and binding, which suggested that some combination of linker sizes could be found to compensate for a zero length linker at $L_4$ in some circumstances.

TABLE 8

Optimization of Linker Sizes with Heavy Chain as Template

| Batch ID | Alignment on HC* | $L_1$ | $L_2$ | $L_3$ | $L_4$ | Yield [mg/L] | Aggregation [%] | KD (Antigen1) IL4 [pM] | KD (Antigen2) IL13 [pM] |
|---|---|---|---|---|---|---|---|---|---|
| 201 | IL4 x IL13 | 5 | 3 | 1 | 2 | 6.3 | 12 | 4 | 72 |
| 202 | IL4 x IL13 | 5 | 5 | 1 | 2 | 10.5 | 7.0 | 9 | 54 |
| 203 | IL4 x IL13 | 7 | 3 | 1 | 2 | 19.3 | 9.4 | 80 | 46 |
| 204 | IL4 x IL13 | 7 | 5 | 1 | 2 | 15.3 | 5.2 | 3 | 25 |
| 205 | IL4 x IL13 | 10 | 3 | 1 | 2 | 4.7 | 4.0 | 8 | 58 |
| 206 | IL4 x IL13 | 10 | 5 | 1 | 2 | 9.1 | 3.9 | 4 | 58 |
| 207 | IL4 x IL13 | 5 | 3 | 2 | 0 | 6.7 | 25.3 | 3 | 33 |
| 208 | IL4 x IL13 | 5 | 5 | 2 | 0 | 10.2 | 18.4 | 10 | 77 |
| 209 | IL4 x IL13 | 7 | 3 | 2 | 0 | 16.2 | 22.2 | 5 | 47 |
| 210 | IL4 x IL13 | 7 | 5 | 2 | 0 | 14.7 | 9.7 | 4 | 47 |
| 211 | IL4 x IL13 | 10 | 3 | 2 | 0 | 2.1 | 12.8 | 7 | 53 |
| 212 | IL4 x IL13 | 10 | 5 | 2 | 0 | 7.0 | 36.3 | 10 | 29 |
| 213 | IL4 x IL13 | 5 | 3 | 2 | 2 | 4.0 | 13.2 | 5 | 27 |
| 214 | IL4 x IL13 | 5 | 5 | 2 | 2 | 8.0 | 7.9 | 10 | 53 |
| 215 | IL4 x IL13 | 7 | 3 | 2 | 2 | 14.9 | 11.5 | 4 | 50 |
| 216 | IL4 x IL13 | 7 | 5 | 2 | 2 | 7.5 | 3.6 | 11 | 40 |
| 217 | IL4 x IL13 | 10 | 3 | 2 | 2 | 2.4 | 4.4 | 8 | 79 |
| 218 | IL4 x IL13 | 10 | 5 | 2 | 2 | 4.6 | 6.6 | 4 | 36 |
| 219 | IL4 x IL13 | 3 | 6 | 3 | 0 | 2.1 | 51.8 | 8 | 71 |
| 220 | IL4 x IL13 | 3 | 10 | 3 | 0 | 3.9 | 59.4 | 1 | 42 |

TABLE 8-continued

Optimization of Linker Sizes with Heavy Chain as Template

| Batch ID | Alignment on HC* | $L_1$ | $L_2$ | $L_3$ | $L_4$ | Yield [mg/L] | Aggregation [%] | KD (Antigen1) IL4 [pM] | KD (Antigen2) IL13 [pM] |
|---|---|---|---|---|---|---|---|---|---|
| 221 | IL4 x IL13 | 3 | 14 | 3 | 0 | 1.9 | 57.6 | 35 | 81 |
| 222 | IL4 x IL13 | 6 | 6 | 3 | 0 | 4.0 | 11.8 | 7 | 53 |
| 223 | IL4 x IL13 | 6 | 10 | 3 | 0 | 10.3 | 16.6 | 6 | 23 |
| 224 | IL4 x IL13 | 6 | 14 | 3 | 0 | 5.1 | 13.5 | 9 | 52 |
| 225 | IL4 x IL13 | 3 | 6 | 3 | 2 | 2.8 | 71.6 | 6 | 68 |
| 226 | IL4 x IL13 | 3 | 10 | 3 | 2 | 7.3 | 65.8 | 6 | 64 |
| 227 | IL4 x IL13 | 3 | 14 | 3 | 2 | 1.6 | 53.6 | 7 | 39 |
| 228 | IL4 x IL13 | 6 | 6 | 3 | 2 | 4.0 | 19.1 | 7 | 44 |
| 229 | IL4 x IL13 | 6 | 10 | 3 | 2 | 2.2 | 15.4 | 3 | 14 |
| 230 | IL4 x IL13 | 6 | 14 | 3 | 2 | 4.0 | 16.2 | 6 | 76 |
| 231 | IL4 x IL13 | 5 | 3 | 5 | 0 | n.p. | — | — | — |
| 232 | IL4 x IL13 | 5 | 5 | 5 | 0 | 0.6 | 24.9 | 8 | 70 |
| 233 | IL4 x IL13 | 7 | 3 | 5 | 0 | 0.4 | 15.1 | 3 | 113 |
| 234 | IL4 x IL13 | 7 | 5 | 5 | 0 | 1.3 | 30.7 | 3 | 122 |
| 235 | IL4 x IL13 | 10 | 3 | 5 | 0 | 0.1 | 11.3 | 2 | 82 |
| 236 | IL4 x IL13 | 10 | 5 | 5 | 0 | 0.4 | 18.6 | 11 | 112 |
| 237 | IL4 x IL13 | 5 | 3 | 5 | 2 | 2.1 | 45.3 | 8.1 | 101.0 |
| 238 | IL4 x IL13 | 5 | 5 | 5 | 2 | 0.6 | 45.4 | 9.3 | 67.2 |
| 239 | IL4 x IL13 | 7 | 3 | 5 | 2 | n.p. | — | — | — |
| 240 | IL4 x IL13 | 7 | 5 | 5 | 2 | 1.6 | 31.7 | 4 | 65 |
| 241 | IL4 x IL13 | 10 | 3 | 5 | 2 | 0.2 | 14.7 | 7 | 119 |
| 242 | IL4 x IL13 | 10 | 5 | 5 | 2 | 1.1 | 17.6 | 10 | 37 |
| 243 | IL4 x IL13 | 3 | 6 | 6 | 0 | 1.6 | 54.3 | 5 | 50 |
| 244 | IL4 x IL13 | 3 | 10 | 6 | 0 | 1.5 | 63.9 | 10 | 10 |
| 245 | IL4 x IL13 | 3 | 14 | 6 | 0 | 1.0 | 61.5 | 10 | 69 |
| 246 | IL4 x IL13 | 6 | 6 | 6 | 0 | 1.1 | 16.2 | 6 | 57 |
| 247 | IL4 x IL13 | 6 | 10 | 6 | 0 | 4.7 | 27.9 | 2 | 41 |
| 248 | IL4 x IL13 | 6 | 14 | 6 | 0 | 0.9 | 18.1 | 10 | 79 |
| 249 | IL4 x IL13 | 10 | 6 | 6 | 0 | 0.3 | 8.7 | 3 | 87 |
| 250 | IL4 x IL13 | 10 | 8 | 6 | 0 | 0.7 | 21.3 | 8 | 53 |
| 251 | IL4 x IL13 | 12 | 6 | 6 | 0 | 1.3 | 9.7 | 8 | 70 |
| 252 | IL4 x IL13 | 12 | 8 | 6 | 0 | 1.3 | 11.7 | 7 | 85 |
| 253 | IL4 x IL13 | 3 | 6 | 6 | 2 | 5.1 | 66.8 | 6 | 66 |
| 254 | IL4 x IL13 | 3 | 10 | 6 | 2 | 2.4 | 62.4 | 6 | 80 |
| 255 | IL4 x IL13 | 3 | 14 | 6 | 2 | 2.0 | 72.1 | 2 | 60 |
| 256 | IL4 x IL13 | 6 | 6 | 6 | 2 | 2.0 | 32.4 | 4 | 81 |
| 257 | IL4 x IL13 | 6 | 10 | 6 | 2 | 1.9 | 29.8 | 7 | 30 |
| 258 | IL4 x IL13 | 6 | 14 | 6 | 2 | 2.5 | 24.6 | 5 | 70 |
| 259 | IL4 x IL13 | 10 | 6 | 6 | 2 | 1.4 | 16.4 | 8 | 71 |
| 260 | IL4 x IL13 | 10 | 8 | 6 | 2 | 0.8 | 16.6 | 10 | 71 |
| 261 | IL4 x IL13 | 12 | 6 | 6 | 2 | 1.2 | 12.3 | 5 | 265 |
| 262 | IL4 x IL13 | 12 | 8 | 6 | 2 | 1.1 | 13.2 | 4 | 111 |
| 263 | IL4 x IL13 | 10 | 6 | 8 | 0 | 2.4 | 10.8 | 2 | 74 |
| 264 | IL4 x IL13 | 10 | 8 | 8 | 0 | 0.8 | 8.0 | 7 | 22 |
| 265 | IL4 x IL13 | 12 | 6 | 8 | 0 | 1.0 | 9.5 | 8 | 66 |
| 266 | IL4 x IL13 | 12 | 8 | 8 | 0 | 2.0 | 9.3 | 3 | 69 |
| 267 | IL4 x IL13 | 10 | 6 | 8 | 2 | 1.4 | 15.0 | 9 | 170 |
| 268 | IL4 x IL13 | 10 | 8 | 8 | 2 | 1.0 | 12.9 | 4 | 52 |
| 269 | IL4 x IL13 | 12 | 6 | 8 | 2 | 1.2 | 8.8 | 5 | 66 |
| 270 | IL4 x IL13 | 12 | 8 | 8 | 2 | 2.4 | 11.7 | 3 | 72 |

*Alignment on the light chain must be $IL13V_L$-$L_1$-$IL4V_L$-$L_2$-$C_{L1}$

The results from Tables 7 and 8 clearly show that linkers are required between the variable and constant domains to allow optimal folding. Only in rare arrangements was a linker equal to zero tolerated (see Batch ID Nos. 103-105, in which $L_1$ (LC) was zero, and Batch No. 210, in which $L_4$ was zero). However, in each case, the corresponding transition linker between the variable region and constant region on the other chain could not be zero.

The results above indicated that the combinations $L_1$=7, $L_2$=5, $L_3$=1, and $L_4$=2 were a good starting point for optimizing a new CODV-Ig in which the heavy chain is the template. The ranges in Table 9 were shown to be reasonable ranges for successfully engineering a new CODV-Ig from two parent antibodies.

TABLE 9

| Ranges of Linker Sizes for Either LC or HC as Template | | | | |
|---|---|---|---|---|
| | LC as Template | | HC as Template | |
| Linker | Max Range | Min Range | Max Range | Min Range |
| $L_1$ | 1-3 | 1-2 | 3-12 | 5-10 |
| $L_2$ | 1-4 | 1-2 | 3-14 | 5-8 |
| $L_3$ | 2-15 | 4-12 | 1-8 | 1-5 |
| $L_4$ | 2-15 | 2-12 | 1-3 | 1-2 |

Example 8

Universal Applicability of CODV-Ig Format

To evaluate the suitability of the CODV-Ig format for engineering new antibody-like binding proteins the variable regions from numerous existing human and humanized antibodies having specificity for insulin-like growth factor 1 receptor (IGF1R(1)), a second antibody to insulin-like growth factor 1 receptor (IGF1R(2)), human epidermal growth factor receptor 2 (HER2), epidermal growth factor receptor (EGFR), tumor necrosis factor-alpha (TNFα), Interleukin 12 and 23 (IL-12/23) and interleukin 1beta (IL-1β) were incorporated into the CODV-Ig format (see Table 10).

TABLE 10

Descriptive Codes for Heavy and Light Chains Used in Bispecific CODV-Ig

| Code* | | SEQ ID NO: |
|---|---|---|
| Heavy Chains (N to C terminal) | | |
| HC10 | IGF1R(1) $V_H$-(Gly)-HER2 $V_H$-(Gly2)-$C_{H1}$-Fc | 32 |
| HC11 | HER2 $V_H$-(Gly)-IGF1R(1) $V_H$-(Gly2)-$C_{H1}$-Fc | 33 |
| HC12 | IGF1R(2) $V_H$-(Gly)-EGFR $V_H$-(Gly2)-$C_{H1}$-Fc | 34 |
| HC13 | EGFR $V_H$-(Gly)-IGF1R(2) $V_H$-(Gly2)-$C_{H1}$-Fc | 35 |
| HC14 | TNFα $V_H$-(Gly)-IL12/23 $V_H$-(Gly2)-$C_{H1}$-Fc | 36 |
| HC15 | IL12/23 $V_H$-(Gly)-TNFα $V_H$-(Gly2)-$C_{H1}$-Fc | 37 |
| HC16 | TNFα $V_H$-(Gly)-IL1β $V_H$-(Gly2)-$C_{H1}$-Fc | 38 |
| HC17 | IL1β $V_H$-(Gly)-TNFα $V_H$-(Gly2)-$C_{H1}$-Fc | 39 |
| Light Chains (N to C terminal) | | |
| LC10 | HER2 $V_L$-(Gly7)-IGF1R(1) $V_L$-(Gly5)-$C_{L1}$ | 40 |
| LC11 | IGF1R(1) $V_L$-(Gly7)-HER2 $V_L$-(Gly5)-$C_{L1}$ | 41 |
| LC12 | EGFR $V_L$-(Gly7)-IGF1R(2) $V_L$-(Gly5)-$C_{L1}$ | 42 |
| LC13 | IGF1R(2) $V_L$-(Gly7)-EGFR $V_L$-(Gly5)-$C_{L1}$ | 43 |
| LC14 | IL12/23 $V_L$-(Gly7)-TNFα $V_L$-(Gly5)-$C_{L1}$ | 44 |
| LC15 | TNFα $V_L$-(Gly7)-IL12/23 $V_L$-(Gly5)-$C_{L1}$ | 45 |
| LC16 | IL1β $V_L$-(Gly7)-TNFα $V_L$-(Gly5)-$C_{L1}$ | 46 |
| LC17 | TNFα $V_L$-(Gly7)-IL1β $V_L$-(Gly5)-$C_{L1}$ | 47 |
| $C_{L1}$ | $C_{L1}$ human light chain constant domain | 23 |
| $C_{H1}$-Fc | $C_{H1}$ human heavy chain constant domain and Fc region | 24 |
| Gly4 | peptide linker with 4 glycines (GGGG) | 25 |
| Gly5 | peptide linker with 5 glycines (GGGGG) | 26 |
| Gly6 | peptide linker with 6 glycines (GGGGGG) | 27 |
| Gly7 | peptide linker with 7 glycines (GGGGGGG) | 28 |
| Gly8 | peptide linker with 8 glycines (GGGG GGGG) | 29 |

*A short hand code was devised to represent the associated structures. Codes beginning with HC represent the adjacent heavy chain and codes beginning with LC represent the adjacent light chains.

The antibody variable regions from known human and humanized antibodies were used to test the universal applicability of the CODV-Ig format in designing bispecific antibody-like binding proteins. In addition, the possibility of positional effects with regard to the placement of certain antibody variable regions either N-terminal or C-terminal on either the heavy chain or the light chain was examined. Based on the design of CODV-Ig molecules having a linker composition of $L_1=7$, $L_2=5$, $L_3=1$, and $L_4=2$, different sequences of antibodies were introduced into the CODV-Ig format.

Activities of bispecific antibodies or derivatives against IL1β and TNFα were determined by using commercially available HEK-Blue TNFα/IL1β reporter cells (InvivoGen). To determine antibody activities against TNFα and IL1β, the cytokines were pre-incubated for 1 hour with different concentrations of the antibodies and added to 50,000 HEK Blue TNFα/IL1β cells. Cytokine mediated induction of SEAP was measured after 24 hours in the culture supernatant with the QUANTI-Blue assay (InvivoGen).

As shown in Table 11, all constructs showed good to excellent protein yield and acceptable levels of aggregation (see, in particular, Batch ID Nos. 301 and 302 in Table 11). The measured affinity for each antibody variable domain was within the published or expected affinity. In cases where affinity was assessed, no positional effects were detected. In summary, as shown in the following tables, no positional effects were seen with any of the antibody variable domains used or with the use of these domains on either antibody chain.

TABLE 11

Universal Use of CODV-Ig Format for Bispecific Antibody-like Binding Proteins

| Batch ID DC/LC Codes[1] | Alignment on HC | $L_1$ | $L_2$ | $L_3$ | $L_4$ | Yield [mg/L] | Aggregation [%] | KD (Antigen 1) [pM] | KD (Antigen 2) [pM] | IC50 [pM] TNFα Cellular Assay |
|---|---|---|---|---|---|---|---|---|---|---|
| 301 HC10/LC10 | IGF1R(1) x HER2 | 7 | 5 | 1 | 2 | 70 | 5.9 | n.m. | 153 (HER2) | — |
| 302 HC11/LC11 | HER2 x IGF1R(1) | 7 | 5 | 1 | 2 | 60 | 1.8 | 163 (HER2) | n.m. | — |
| 303 HC12/LC12 | IGF1R(2) x EGFR | 7 | 5 | 1 | 2 | 17 | 2.7 | n.m. | — | — |
| 304 HC13/LC13 | EGFR x IGF1R(2) | 7 | 5 | 1 | 2 | 9.5 | 4.3 | — | n.m. | — |
| 305 HC14/LC14 | TNFα x IL12/23 | 7 | 5 | 1 | 2 | 7.1 | 7.5 | 321 (TNFα) | 65 (IL23) | 95 |
| 306 HC15/LC15 | IL12/23 x TNFα | 7 | 5 | 1 | 2 | 11.9 | 7.1 | 118 (IL23) | 543 (TNFα) | 138 |
| 307 HC16/LC16 | TNFα x IL1β | 7 | 5 | 1 | 2 | 6.6 | 13.6 | 340 (TNFα) | 155 (IL1β) | 136 |
| 308 HC17/LC17 | IL1β x TNFα | 7 | 5 | 1 | 2 | 2.4 | 5.7 | 97.5 (IL1β) | 358 (TNFα) | 138 |

*n.m. = not measurable by Biacore.
[1]Heavy chain and light chains corresponding to codes can be found in Table 10.

Example 9

Retention of Parental Antibody Affinity in CODV-Ig Format

Figure 7:
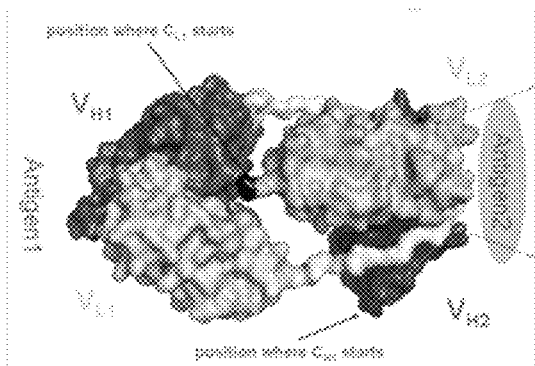
FIG. 7. Comparison of TBTI/DVD-Ig or CODV-Ig molecules incorporating anti-IL4 and anti-IL13 sequences.
Figure 7:
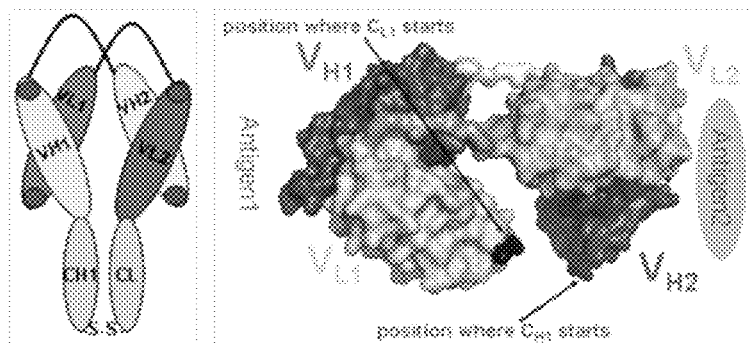

The identical antibody sequences for anti-IL4 and anti-IL13 were incorporated into either the TBTI/DVD-Ig or CODV-Ig formats for a direct comparison of these configurations, the positioning of the linkers, and affinities of the resulting molecules. As shown in FIG. 7, the parental affinity of each of the antibodies was maintained in the CODV format. As shown in the upper panel of FIG. 7, when the variable regions were placed in the TBTI/DVD-Ig format, a drop in affinity of the IL4 antibody positioned at the inner Fv2 position was manifested as a reduction of the on-rate of antibody binding to the antigen. In contrast, there was no loss in affinity for the CODV-Ig format as compared to the parental antibodies (see FIG. 7, lower panel).

Example 10

Adaptability of CODV-Ig to Fab Format

The ability of the CODV-Ig format to provide fragments such as Fab fragments was evaluated next. Two different variable heavy chains were fused to each other through linker $L_3$ and elongated C-terminally by linker $L_4$. This $V_H$ complex was then fused to the $C_{H1}$ domain of IGHG1 (GenBank Accession No. Q569F4) harboring C-terminally the five amino acid sequence DKTHT (SEQ ID NO: 60) from the hinge region followed by six histidine residues. Two different variable light chains were fused to each other in a cross-over configuration to the corresponding heavy chain through linker $L_1$ and extended C-terminally by linker $L_2$ and subsequently fused to the constant kappa chain (IGKC, GenBank Accession No. Q502W4).

Fab fragments were expressed by transient transfection as described previously. Seven days post-transfection, cells were removed by centrifugation, 10% vol/vol 1M Tris-HCl, pH 8.0, was added and the supernatant was passed over a 0.22 μm filter to remove particles. The Fab proteins were captured using HisTrap High Performance columns (GE Healthcare) and eluted via imidazole gradient. The protein containing fractions were pooled and desalted using PD-10 or Sephadex columns. Concentrated and sterile filtered (0.22 μm) protein solutions were adjusted to 1 mg/ml and kept at 4° C. until use.

Immediate advantages were observed in that the Fab-like molecules in a CODV orientation showed no tendency to aggregate and retained the affinities of the parental antibodies (see Table 12). Binding protein constructs from Batch ID Nos. 401-421 directly compared antibody-like proteins in which antibody variable regions were arranged as in CODV-Ig molecules with the heavy chain as the template (401, 402, 406, and 407), CODV Fab-like fragments (402, 408, 413, 418, and 421), four domain antibody-like molecules in TBTI/DVD-Ig format (404, 409, 414, and 419), and CODV-Ig with no linkers (405, 410, 415, and 420). As shown in Table 12, the results of this comparison indicated that there is more likely to be a loss in affinity as compared to the parent antibodies when the variable region is incorporated into a TBTI or DVD-Ig format. In contrast, both the CODV-Ig and CODV-Ig Fab-like formats were better able to maintain parental affinities. The results further confirmed that CODV-Ig molecules require linkers between the variable regions and between the variable regions and the constant domains (see Table 12).

TABLE 12

Use of CODV-Ig Format for Fab-like Fragments

| Batch ID | Sample-ID | Format | $L_1$ | $L_2$ | $L_3$ | $L_4$ | Yield [mg/L] | Aggregation [%] | KD (Antigen 1) [pM] | KD (Antigen 2) [pM] | IC50 [pM] TNFα Cellular Assay |
|---|---|---|---|---|---|---|---|---|---|---|---|
| 401 | TNFα x IL12/23 | CODV-Ig | 7 | 5 | 1 | 2 | 7.1 | 7.5 | 321 (TNFα) | 90 (IL23) | 95 |
| 402 | IL12/23 x TNFα | CODV-Ig | 7 | 5 | 1 | 2 | 11.9 | 7.1 | 118 (IL23) | 543 (TNFα) | 138 |
| 403 | TNFα x IL12/23 | CODV-Fab | 7 | 5 | 1 | 2 | 18.7 | 1.7 | 232 (TNFα) | 41 (IL23) | 785 |
| 404 | TNFα x IL12/23 | TBTI | (G4S)2 | 0 | (G4S)2 | 0 | 26.0 | 8.7 | 219 (TNFα) | 399 (IL23) | — |
| 405 | TNFα x IL12/23 | CODV-Ig | 0 | 0 | 0 | 0 | 3.5 | 71 | — | — | — |
| 406 | IL1β x TNFα | CODV-Ig | 7 | 5 | 1 | 2 | 2.4 | 5.7 | 98 (IL1β) | 358 (TNFα) | 139 |
| 407 | TNFα x IL1β | CODV-Ig | 7 | 5 | 1 | 2 | 6.6 | 13.6 | 340 (TNFα) | 155 (IL1β) | 122 |
| 408 | IL1β x TNFα | CODV-Fab | 7 | 5 | 1 | 2 | 8.6 | 0 | 179 (IL1β) | — | — |
| 409 | IL1β x TNFα | TBTI | (G4S)2 | 0 | (G4S)2 | 0 | 1.3 | 40.5 | 133 (IL1β) | 456 (TNFα) | — |
| 410 | TNFα x IL1β | CODV-Ig | 0 | 0 | 0 | 0 | n.p. | — | — | — | — |
| 411 | EGFR x IGF1R(2) | CODV-Ig | 7 | 5 | 1 | 2 | 9.5 | 4.3 | 124 nM (EGFR) | n.m. | — |
| 412 | IGF1R(2) x EGFR | CODV-Ig | 7 | 5 | 1 | 2 | 17 | 2.7 | n.m. | — | — |
| 413 | EGFR x IGF1R(2) | CODV-Fab | 7 | 5 | 1 | 2 | 13.3 | 0 | 42 nM (EGFR) | n.m. | — |
| 414 | EGFR x IGF1R(2) | TBTI | (G4S)2 | 0 | (G4S)2 | 0 | 2.1 | 2.9 | 7 nM (EGFR) | n.m. | — |
| 415 | EGFR x IGF1R(2) | CODV-Ig | 0 | 0 | 0 | 0 | 4.4 | 100 | — | — | — |
| 416 | HER2 x IGF1R(1) | CODV-Ig | 7 | 5 | 1 | 2 | 60.0 | 1.8 | 163 (HER2) | n.m. | — |
| 417 | IGF1R(1) x HER2 | CODV-Ig | 7 | 5 | 1 | 2 | 70 | 5.9 | n.m. | 41 (HER2) | — |
| 418 | HER2 x IGF1R(1) | CODV-Fab | 7 | 5 | 1 | 2 | 34.4 | 0 | 190 (HER2) | n.m. | — |
| 419 | HER2 x IGF1R(1) | TBTI | (G4S)2 | 0 | (G4S)2 | 0 | 6.3 | 6.8 | 56 (HER2) | n.m. | — |
| 420 | IGF1R(1) x HER2 | CODV-Ig | 0 | 0 | 0 | 0 | 0.35 | 54.5 | — | — | — |
| 421 | IL4 x IL13 | CODV-Fab | 7 | 5 | 1 | 2 | 8.7 | 14 | 12 (IL4) | 48 (IL13) | — |

Example 11

Substitution of Variable Domains within CODV-Ig and CODV-Fab

To characterize the CODV format in a T-cell engaging approach, bispecific CODV Fab-like binding proteins (CODV-Fab) having a TCR binding site (CD3epsilon) and a CD19 binding site were generated and compared to a bispecific Fab derived from the TBTI/DVD-Ig format (B-Fab). To investigate the importance of the orientation of the binding sites (TCR×CD19 vs. CD19×TCR), both orientations were evaluated for each of the binding proteins.

The binding proteins were characterized in a cytotoxic assay using NALM-6 (CD19 expressing) cells as target cells and primary human T-cells as effector cells. CD3 positive cells were isolated from freshly prepared human PBMC's. Effector and target cells were mixed at a ratio of 10:1 and incubated for 20 hours with the indicated concentrations of bispecific binding proteins (see FIG. 8). Apoptotic target cells were determined in a FACS-based assay using 7-Aminoactinomycin staining The B-Fab format in the configuration CD3-CD19 (1060) was shown to be active in inducing T-cell mediated cytotoxicity towards NALM-6 cells with an EC50 of 3.7 ng/ml. A similarly high activity was observed for the CD19-CD3 CODV-Fab (1109) with an EC50 of 3.2 ng/ml (see FIG. 8).

Figure 8:
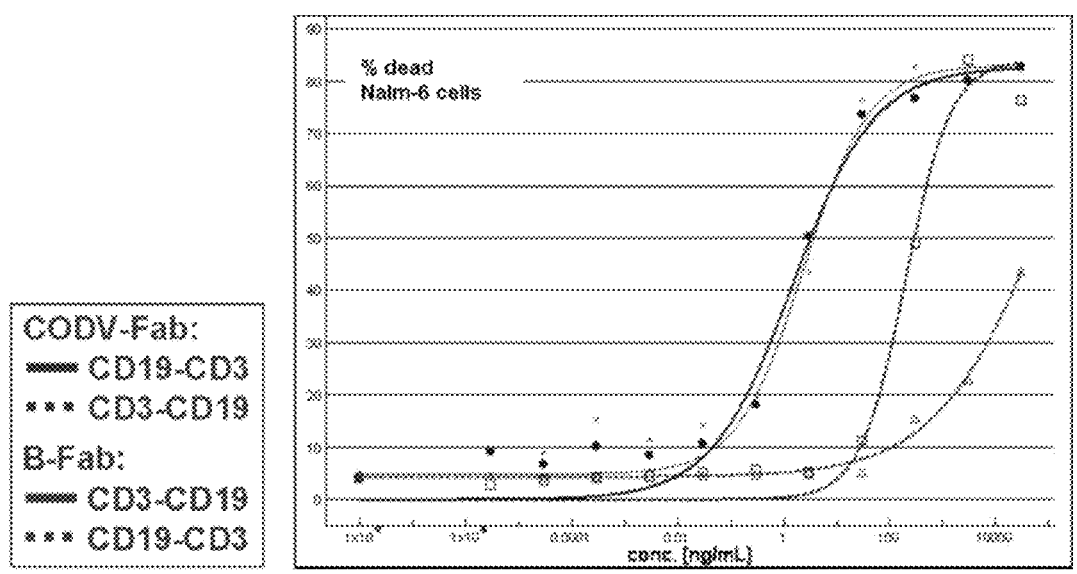
FIG. 8. Comparison of CODV-Fab and B-Fab formats in a cytotoxic assay using NALM-6 cells.

A swap of the configuration of the B-Fab molecule (Fab of the TBTI/DVD-Ig format) to a CD19-CD3 orientation resulted in a significant loss of activity (see FIG. 8). The swapped B-Fab molecule showed no activity at concentrations that were maximal for both orientations of CODV-Ig Fab and the other orientation of B-Fab. For the CODV-Ig Fabs and one orientation of B-Fab, a maximum response was observed (ranging between 1 and 100 ng/ml). For the CD19-CD3 orientation of B-Fab, even at the maximal concentration (30 μg/ml), the optimal cytotoxic response was not reached. In sharp contrast, a change in the orientation of the domains in the CODV-Fab towards CD3-CD19 (1108), resulted in a molecule with significant activity in this assay (see FIG. 8). Although domain swapping in the CODV-Fab also reduced the induction of T-cell mediated cytotoxicity (increase of EC50 by factor ~100), this effect was far less pronounced than was seen in the B-Fab format and the molecule was able to induce cytotoxicity up to the maximal level. The data were representative and obtained from three independent experiments.

Example 12

Influence of Amino Acid Sequence Identity on CODV-Ig Linkers

The optimized construct corresponding to Batch ID 204 (see Example 7 and Table 8) was chosen to investigate the influence of linker composition on the linkers $L_1$ to $L_4$. Linker lengths were set at 7, 5, 1, and 2 residues in length for $L_1$, $L_2$, $L_3$, and $L_4$, respectively (see Table 13). Test sequences were derived from naturally occurring linkers at the transitions between natural antibody $V_H$ and $C_{H1}$ domains or between antibody Fv and $C_L$ domains of kappa or lambda light chains. The candidate sequences were ASTKGPS (SEQ ID NO: 48), which is derived from the $V_H$ and $C_{H1}$ domain transition, RTVAAPS (SEQ ID NO: 49) and GQPKAAP (SEQ ID NO: 50), which were derived from the Fv and $C_L$ domain transitions of kappa and lambda light chains, respectively. Furthermore, one construct was generated with an arbitrary linker composition to show that any sequence can be potentially used in linkers $L_1$ to $L_4$. This linker composition was obtained by randomly distributing the amino acids valine, leucine, isoleucine, serine, threonine, lysine, arginine, histidine, aspartate, glutamate, asparagine, glutamine, glycine, and proline at the 15 positions of the four linkers. The aromatic amino acids phenylalanine, tyrosine, and tryptophan, as well as the amino acids methionine and cysteine were deliberately excluded to avoid potential increases in aggregation.

A three-dimensional model of the construct for Batch ID No. 204 was generated to assure suitability or refine the choices of linker composition. Thus, serine was chosen for linker $L_3$ as positively and negatively charged residues are observed nearby in the three-dimensional model. The residues in linker $L_4$ were selected to be compatible with solvent exposure of these positions as suggested by the model. Similarly, no problems were anticipated or predicted for the linker compositions of $L_1$ and $L_2$. Three-dimensional models of selected proposals for linker composition were constructed.

As shown in Table 12, linker composition may have a dramatic influence on yield. Sequences that were derived from lambda chain on $L_1$ (comparing Batch ID Nos. 505-507 with Batch ID Nos. 501-503) were more productive protein generators (up to 8 fold increase). Indeed, the linkers based on random generation also produced good yields, as shown in Table 13, Batch ID No. 508. Therefore, linker composition should be one parameter considered during CODV-Ig optimization.

TABLE 13

Effect of Linker Composition on CODV-Ig

| Batch ID | Alignment on HC | $L_1$ | $L_2$ | $L_3$ | $L_4$ | Yield [mg/L] | Aggregation [%] | KD (IL4) [pM] | KD (IL13) [pM] | IC50 Cellular Assay IL4 [nM] | IC50 Cellular Assay IL13 [nM] |
|---|---|---|---|---|---|---|---|---|---|---|---|
| 501 | IL4 × IL13 | ASTKGPS (SEQ ID NO: 48) | TKGPS (SEQ ID NO: 52) | S | RT | 10.8 | 1.2 | 1 | 55 | 0.034 | 4.5 |
| 502 | IL4 × IL13 | ASTKGPS (SEQ ID NO: 48) | TVAAP (SEQ ID NO: 53) | S | QP | 15.8 | 2.9 | 3 | 61 | 0.049 | 2.4 |
| 503 | IL4 × IL13 | ASTKGPS (SEQ ID NO: 48) | TVAAP (SEQ ID NO: 53) | S | SS | 11.6 | 3.5 | 3 | 52 | 0.047 | 2.1 |
| 504 | IL4 × IL13 | RTVAAPS (SEQ ID NO: 49) | QPKAA (SEQ ID NO: 54) | S | TK | 15 | 1.9 | 8 | 71 | 0.042 | 1.4 |

TABLE 13-continued

Effect of Linker Composition on CODV-Ig

| Batch ID | Alignment on HC | $L_1$ | $L_2$ | $L_3$ | $L_4$ | Yield [mg/L] | A

TABLE 14

Effect of Disulfide Bridge Stabilization on CODV-Ig

| Batch

TABLE 16B

Effect of Disulfide Bridge Stabilization on CODV-Iq

| Batch ID | Alignment on HC | Introduced Mutations LC | Introduced Mutations HC | L₁ | L₂

-continued

IL4 antibody

<400> SEQUENCE: 2

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 3
<211> LENGTH: 111
<212> TYPE: PRT
<213> ORGANISM: Artificial Sequence
<220> FEATURE:
<223> OTHER INFORMATION: Humanized light chain V region (VL) from an
      anti-IL13 antibody

<400> SEQUENCE: 3

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
            100                 105                 110

<210> SEQ ID NO 4
<211> LENGTH: 118
<212> TYPE: PRT
<213> ORGANISM: Artificial Sequence
<220> FEATURE:
<223> OTHER INFORMATION: Humanized heavy chain V region (VH) from an
      anti-IL-13 antibody.

<400> SEQUENCE: 4

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

```
Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                    85                  90                  95

Arg Asp Gly Tyr Phe Pro Tyr Ala Met Asp Phe Trp Gly Gln Gly Thr
                100                 105                 110

Ser Val Thr Val Ser Ser
            115

<210> SEQ ID NO 5
<211> LENGTH: 575
<212> TYPE: PRT
<213> ORGANISM: Artificial Sequence
<220> FEATURE:
<223> OTHER INFORMATION: Heavy chain of cross over double head construct
      IL13(G4S)IL4CHFc

<400> SEQUENCE: 5

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                    85                  90                  95

Arg Asp Gly Tyr Phe Pro Tyr Ala Met Asp Phe Trp Gly Gln Gly Thr
                100                 105                 110

Ser Val Thr Val Ser Ser Gly Gly Gly Gly Ser Gln Val Gln Leu Gln
            115                 120                 125

Gln Ser Gly Pro Glu Leu Val Lys Pro Gly Ala Ser Val Lys Ile Ser
        130                 135                 140

Cys Lys Ala Ser Gly Tyr Ser Phe Thr Ser Tyr Trp Ile His Trp Ile
145                 150                 155                 160

Lys Gln Arg Pro Gly Gln Gly Leu Glu Trp Ile Gly Met Ile Asp Pro
                165                 170                 175

Ser Asp Gly Glu Thr Arg Leu Asn Gln Arg Phe Gln Gly Arg Ala Thr
                180                 185                 190

Leu Thr Val Asp Glu Ser Thr Ser Thr Ala Tyr Met Gln Leu Arg Ser
            195                 200                 205

Pro Thr Ser Glu Asp Ser Ala Val Tyr Tyr Cys Thr Arg Leu Lys Glu
        210                 215                 220

Tyr Gly Asn Tyr Asp Ser Phe Tyr Phe Asp Val Trp Gly Ala Gly Thr
225                 230                 235                 240

Leu Val Thr Val Ser Ser Ala Ser Thr Lys Gly Pro Ser Val Phe Pro
                245                 250                 255

Leu Ala Pro Ser Ser Lys Ser Thr Ser Gly Gly Thr Ala Ala Leu Gly
                260                 265                 270

Cys Leu Val Lys Asp Tyr Phe Pro Glu Pro Val Thr Val Ser Trp Asn
```

```
                275                 280                 285
Ser Gly Ala Leu Thr Ser Gly Val His Thr Phe Pro Ala Val Leu Gln
            290                 295                 300

Ser Ser Gly Leu Tyr Ser Leu Ser Ser Val Val Thr Val Pro Ser Ser
305                 310                 315                 320

Ser Leu Gly Thr Gln Thr Tyr Ile Cys Asn Val Asn His Lys Pro Ser
                325                 330                 335

Asn Thr Lys Val Asp Lys Lys Val Glu Pro Lys Ser Cys Asp Lys Thr
            340                 345                 350

His Thr Cys Pro Pro Cys Pro Ala Pro Glu Leu Leu Gly Gly Pro Ser
        355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
                405                 410                 415

Lys Thr Lys Pro Arg Glu Glu Gln Tyr Asn Ser Thr Tyr Arg Val Val
            420                 425                 430

Ser Val Leu Thr Val Leu His Gln Asp Trp Leu Asn Gly Lys Glu Tyr
        435                 440                 445

Lys Cys Lys Val Ser Asn Lys Ala Leu Pro Ala Pro Ile Glu Lys Thr
    450                 455                 460

Ile Ser Lys Ala Lys Gly Gln Pro Arg Glu Pro Gln Val Tyr Thr Leu
465                 470                 475                 480

Pro Pro Ser Arg Asp Glu Leu Thr Lys Asn Gln Val Ser Leu Thr Cys
                485                 490                 495

Leu Val Lys Gly Phe Tyr Pro Ser Asp Ile Ala Val Glu Trp Glu Ser
            500                 505                 510

Asn Gly Gln Pro Glu Asn Asn Tyr Lys Thr Thr Pro Pro Val Leu Asp
        515                 520                 525

Ser Asp Gly Ser Phe Phe Leu Tyr Ser Lys Leu Thr Val Asp Lys Ser
    530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly
                565                 570                 575

<210> SEQ ID NO 6
<211> LENGTH: 580
<212> TYPE: PRT
<213> ORGANISM: Artificial Sequence
<220> FEATURE:
<223> OTHER INFORMATION: heavy chain of cross over double head construct
      IL13(G4S2)IL4CHFc

<400> SEQUENCE: 6

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60
```

-continued

```
Ser Arg Leu Ser Ile Ser Lys Asp Ser Ser Lys Ser Gln Val Phe Leu
 65                  70                  75                  80

Glu Met Thr Ser Leu Arg Thr Asp Asp Thr Ala Thr Tyr Tyr Cys Ala
                 85                  90                  95

Arg Asp Gly Tyr Phe Pro Tyr Ala Met Asp Phe Trp Gly Gln Gly Thr
            100                 105                 110

Ser Val Thr Val Ser Ser Gly Gly Gly Gly Ser Gly Gly Gly Gly Ser
        115                 120                 125

Gln Val Gln Leu Gln Gln Ser Gly Pro Glu Leu Val Lys Pro Gly Ala
    130                 135                 140

Ser Val Lys Ile Ser Cys Lys Ala Ser Gly Tyr Ser Phe Thr Ser Tyr
145                 150                 155                 160

Trp Ile His Trp Ile Lys Gln Arg Pro Gly Gln Gly Leu Glu Trp Ile
                165                 170                 175

Gly Met Ile Asp Pro Ser Asp Gly Glu Thr Arg Leu Asn Gln Arg Phe
            180                 185                 190

Gln Gly Arg Ala Thr Leu Thr Val Asp Glu Ser Thr Ser Thr Ala Tyr
        195                 200                 205

Met Gln Leu Arg Ser Pro Thr Ser Glu Asp Ser Ala Val Tyr Tyr Cys
    210                 215                 220

Thr Arg Leu Lys Glu Tyr Gly Asn Tyr Asp Ser Phe Tyr Phe Asp Val
225                 230                 235                 240

Trp Gly Ala Gly Thr Leu Val Thr Val Ser Ser Ala Ser Thr Lys Gly
                245                 250                 255

Pro Ser Val Phe Pro Leu Ala Pro Ser Ser Lys Ser Thr Ser Gly Gly
            260                 265                 270

Thr Ala Ala Leu Gly Cys Leu Val Lys Asp Tyr Phe Pro Glu Pro Val
        275                 280                 285

Thr Val Ser Trp Asn Ser Gly Ala Leu Thr Ser Gly Val His Thr Phe
    290                 295                 300

Pro Ala Val Leu Gln Ser Ser Gly Leu Tyr Ser Leu Ser Ser Val Val
305                 310                 315                 320

Thr Val Pro Ser Ser Ser Leu Gly Thr Gln Thr Tyr Ile Cys Asn Val
                325                 330                 335

Asn His Lys Pro Ser Asn Thr Lys Val Asp Lys Lys Val Glu Pro Lys
            340                 345                 350

Ser Cys Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
    450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Asp Glu Leu Thr Lys Asn Gln
```

```
                    485                 490                 495
Val Ser Leu Thr Cys Leu Val Lys Gly Phe Tyr Pro Ser Asp Ile Ala
                500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Tyr Ser Lys Leu
        530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly
            580

<210> SEQ ID NO 7
<211> LENGTH: 698
<212> TYPE: PRT
<213> ORGANISM: Artificial Sequence
<220> FEATURE:
<223> OTHER INFORMATION: Heavy chain cross over double head construct
      IL4(G4S)IL13CHFc

<400> SEQUENCE: 7

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Gly Gly Gly Gly Ser
        115                 120                 125

Glu Val Gln Leu Lys Glu Ser Gly Pro Gly Leu Val Ala Pro Gly Gly
    130                 135                 140

Ser Leu Ser Ile Thr Cys Thr Val Ser Gly Phe Ser Leu Thr Asp Ser
145                 150                 155                 160

Ser Ile Asn Trp Val Arg Gln Pro Pro Gly Lys Gly Leu Glu Trp Leu
                165                 170                 175

Gly Met Ile Trp Gly Asp Gly Arg Ile Asp Tyr Ala Asp Ala Leu Lys
            180                 185                 190

Ser Arg Leu Ser Ile Ser Lys Asp Ser Ser Lys Ser Gln Val Phe Leu
        195                 200                 205

Glu Met Thr Ser Leu Arg Thr Asp Asp Thr Ala Thr Tyr Tyr Cys Ala
    210                 215                 220

Arg Asp Gly Tyr Phe Pro Tyr Ala Met Asp Phe Trp Gly Gln Gly Thr
225                 230                 235                 240

Ser Val Thr Val Ser Ser Gln Val Gln Leu Gln Gln Ser Gly Pro Glu
                245                 250                 255
```

```
Leu Val Lys Pro Gly Ala Ser Val Lys Ile Ser Cys Lys Ala Ser Gly
            260                 265                 270

Tyr Ser Phe Thr Ser Tyr Trp Ile His Trp Ile Lys Gln Arg Pro Gly
            275                 280                 285

Gln Gly Leu Glu Trp Ile Gly Met Ile Asp Pro Ser Asp Gly Glu Thr
            290                 295                 300

Arg Leu Asn Gln Arg Phe Gln Gly Arg Ala Thr Leu Thr Val Asp Glu
305                 310                 315                 320

Ser Thr Ser Thr Ala Tyr Met Gln Leu Arg Ser Pro Thr Ser Glu Asp
            325                 330                 335

Ser Ala Val Tyr Tyr Cys Thr Arg Leu Lys Glu Tyr Gly Asn Tyr Asp
            340                 345                 350

Ser Phe Tyr Phe Asp Val Trp Gly Ala Gly Thr Leu Val Thr Val Ser
            355                 360                 365

Ser Ala Ser Thr Lys Gly Pro Ser Val Phe Pro Leu Ala Pro Ser Ser
            370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
            405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
            435                 440                 445

Thr Tyr Ile Cys Asn Val Asn His Lys Pro Ser Asn Thr Lys Val Asp
450                 455                 460

Lys Lys Val Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
            485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
            515                 520                 525

Trp Tyr Val Asp Gly Val Glu Val His Asn Ala Lys Thr Lys Pro Arg
530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
            565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Asp
            595                 600                 605

Glu Leu Thr Lys Asn Gln Val Ser Leu Thr Cys Leu Val Lys Gly Phe
            610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
            645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
```

-continued

```
            675                 680                 685
Thr Gln Lys Ser Leu Ser Leu Ser Pro Gly
    690                 695

<210> SEQ ID NO 8
<211> LENGTH: 703
<212> TYPE: PRT
<213> ORGANISM: Artificial Sequence
<220> FEATURE:
<223> OTHER INFORMATION: Heavy chain cross over double head construct
      IL4(G4S2)IL13CHFc

<400> SEQUENCE: 8

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Gly Gly Gly Gly Ser
        115                 120                 125

Gly Gly Gly Gly Ser Glu Val Gln Leu Lys Glu Ser Gly Pro Gly Leu
    130                 135                 140

Val Ala Pro Gly Gly Ser Leu Ser Ile Thr Cys Thr Val Ser Gly Phe
145                 150                 155                 160

Ser Leu Thr Asp Ser Ser Ile Asn Trp Val Arg Gln Pro Pro Gly Lys
                165                 170                 175

Gly Leu Glu Trp Leu Gly Met Ile Trp Gly Asp Gly Arg Ile Asp Tyr
            180                 185                 190

Ala Asp Ala Leu Lys Ser Arg Leu Ser Ile Ser Lys Asp Ser Ser Lys
        195                 200                 205

Ser Gln Val Phe Leu Glu Met Thr Ser Leu Arg Thr Asp Asp Thr Ala
    210                 215                 220

Thr Tyr Tyr Cys Ala Arg Asp Gly Tyr Phe Pro Tyr Ala Met Asp Phe
225                 230                 235                 240

Trp Gly Gln Gly Thr Ser Val Thr Val Ser Ser Gln Val Gln Leu Gln
                245                 250                 255

Gln Ser Gly Pro Glu Leu Val Lys Pro Gly Ala Ser Val Lys Ile Ser
            260                 265                 270

Cys Lys Ala Ser Gly Tyr Ser Phe Thr Ser Tyr Trp Ile His Trp Ile
        275                 280                 285

Lys Gln Arg Pro Gly Gln Gly Leu Glu Trp Ile Gly Met Ile Asp Pro
    290                 295                 300

Ser Asp Gly Glu Thr Arg Leu Asn Gln Arg Phe Gln Gly Arg Ala Thr
305                 310                 315                 320

Leu Thr Val Asp Glu Ser Thr Ser Thr Ala Tyr Met Gln Leu Arg Ser
                325                 330                 335
```

Pro Thr Ser Glu Asp Ser Ala Val Tyr Tyr Cys Thr Arg Leu Lys Glu
                340                 345                 350

Tyr Gly Asn Tyr Asp Ser Phe Tyr Phe Asp Val Trp Gly Ala Gly Thr
            355                 360                 365

Leu Val Thr Val Ser Ser Ala Ser Thr Lys Gly Pro Ser Val Phe Pro
        370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
        435                 440                 445

Ser Leu Gly Thr Gln Thr Tyr Ile Cys Asn Val Asn His Lys Pro Ser
450                 455                 460

Asn Thr Lys Val Asp Lys Lys Val Glu Pro Lys Ser Cys Asp Lys Thr
465                 470                 475                 480

His Thr Cys Pro Pro Cys Pro Ala Pro Glu Leu Leu Gly Gly Pro Ser
                485                 490                 495

Val Phe Leu Phe Pro Pro Lys Pro Lys Asp Thr Leu Met Ile Ser Arg
            500                 505                 510

Thr Pro Glu Val Thr Cys Val Val Val Asp Val Ser His Glu Asp Pro
        515                 520                 525

Glu Val Lys Phe Asn Trp Tyr Val Asp Gly Val Glu Val His Asn Ala
530                 535                 540

Lys Thr Lys Pro Arg Glu Glu Gln Tyr Asn Ser Thr Tyr Arg Val Val
545                 550                 555                 560

Ser Val Leu Thr Val Leu His Gln Asp Trp Leu Asn Gly Lys Glu Tyr
                565                 570                 575

Lys Cys Lys Val Ser Asn Lys Ala Leu Pro Ala Pro Ile Glu Lys Thr
            580                 585                 590

Ile Ser Lys Ala Lys Gly Gln Pro Arg Glu Pro Gln Val Tyr Thr Leu
        595                 600                 605

Pro Pro Ser Arg Asp Glu Leu Thr Lys Asn Gln Val Ser Leu Thr Cys
610                 615                 620

Leu Val Lys Gly Phe Tyr Pro Ser Asp Ile Ala Val Glu Trp Glu Ser
625                 630                 635                 640

Asn Gly Gln Pro Glu Asn Asn Tyr Lys Thr Thr Pro Pro Val Leu Asp
                645                 650                 655

Ser Asp Gly Ser Phe Phe Leu Tyr Ser Lys Leu Thr Val Asp Lys Ser
            660                 665                 670

Arg Trp Gln Gln Gly Asn Val Phe Ser Cys Ser Val Met His Glu Ala
        675                 680                 685

Leu His Asn His Tyr Thr Gln Lys Ser Leu Ser Leu Ser Pro Gly
690                 695                 700

<210> SEQ ID NO 9
<211> LENGTH: 330
<212> TYPE: PRT
<213> ORGANISM: Artificial Sequence
<220> FEATURE:
<223> OTHER INFORMATION: Light chain cross over double head construct
      IL13(G4S)IL4CL

<400> SEQUENCE: 9

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys Gly
            100                 105                 110

Gly Gly Gly Ser Asp Ile Gln Met Thr Gln Ser Pro Ala Ser Leu Ser
        115                 120                 125

Val Ser Val Gly Asp Thr Ile Thr Leu Thr Cys His Ala Ser Gln Asn
130                 135                 140

Ile Asp Val Trp Leu Ser Trp Phe Gln Gln Lys Pro Gly Asn Ile Pro
145                 150                 155                 160

Lys Leu Leu Ile Tyr Lys Ala Ser Asn Leu His Thr Gly Val Pro Ser
                165                 170                 175

Arg Phe Ser Gly Ser Gly Ser Gly Thr Gly Phe Thr Leu Thr Ile Ser
            180                 185                 190

Ser Leu Gln Pro Glu Asp Ile Ala Thr Tyr Tyr Cys Gln Gln Ala His
        195                 200                 205

Ser Tyr Pro Phe Thr Phe Gly Gly Gly Thr Lys Leu Glu Ile Lys Arg
    210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
                245                 250                 255

Pro Arg Glu Ala Lys Val Gln Trp Lys Val Asp Asn Ala Leu Gln Ser
            260                 265                 270

Gly Asn Ser Gln Glu Ser Val Thr Glu Gln Asp Ser Lys Asp Ser Thr
        275                 280                 285

Tyr Ser Leu Ser Ser Thr Leu Thr Leu Ser Lys Ala Asp Tyr Glu Lys
    290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 10
<211> LENGTH: 335
<212> TYPE: PRT
<213> ORGANISM: Artificial Sequence
<220> FEATURE:
<223> OTHER INFORMATION: Light chain cross over double head construct
      IL13(G4S2)IL4CL

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr

-continued

```
                20                  25                  30
Gly Gln Ser Tyr Met His Trp Tyr Gln Gln Lys Ala Gly Gln Pro Pro
            35                  40                  45
Lys Leu Leu Ile Tyr Leu Ala Ser Asn Leu Glu Ser Gly Val Pro Ala
 50                  55                  60
Arg Phe Ser Gly Ser Gly Ser Arg Thr Asp Phe Thr Leu Thr Ile Asp
 65                  70                  75                  80
Pro Val Gln Ala Glu Asp Ala Ala Thr Tyr Tyr Cys Gln Gln Asn Ala
                85                  90                  95
Glu Asp Ser Arg Thr Phe Gly Gly Thr Lys Leu Glu Ile Lys Gly
            100                 105                 110
Gly Gly Gly Ser Gly Gly Gly Ser Asp Ile Gln Met Thr Gln Ser
            115                 120                 125
Pro Ala Ser Leu Ser Val Ser Val Gly Asp Thr Ile Thr Leu Thr Cys
            130                 135                 140
His Ala Ser Gln Asn Ile Asp Val Trp Leu Ser Trp Phe Gln Gln Lys
145                 150                 155                 160
Pro Gly Asn Ile Pro Lys Leu Leu Ile Tyr Lys Ala Ser Asn Leu His
                165                 170                 175
Thr Gly Val Pro Ser Arg Phe Ser Gly Ser Gly Ser Gly Thr Gly Phe
            180                 185                 190
Thr Leu Thr Ile Ser Ser Leu Gln Pro Glu Asp Ile Ala Thr Tyr Tyr
            195                 200                 205
Cys Gln Gln Ala His Ser Tyr Pro Phe Thr Phe Gly Gly Gly Thr Lys
            210                 215                 220
Leu Glu Ile Lys Arg Thr Val Ala Ala Pro Ser Val Phe Ile Phe Pro
225                 230                 235                 240
Pro Ser Asp Glu Gln Leu Lys Ser Gly Thr Ala Ser Val Val Cys Leu
                245                 250                 255
Leu Asn Asn Phe Tyr Pro Arg Glu Ala Lys Val Gln Trp Lys Val Asp
            260                 265                 270
Asn Ala Leu Gln Ser Gly Asn Ser Gln Glu Ser Val Thr Glu Gln Asp
            275                 280                 285
Ser Lys Asp Ser Thr Tyr Ser Leu Ser Ser Thr Leu Thr Leu Ser Lys
            290                 295                 300
Ala Asp Tyr Glu Lys His Lys Val Tyr Ala Cys Glu Val Thr His Gln
305                 310                 315                 320
Gly Leu Ser Ser Pro Val Thr Lys Ser Phe Asn Arg Gly Glu Cys
                325                 330                 335
```

<210> SEQ ID NO 11
<211> LENGTH: 330
<212> TYPE: PRT
<213> ORGANISM: Artificial Sequence
<220> FEATURE:
<223> OTHER INFORMATION: Light chain cross over double head construct IL4(G4S)IL13CL

<400> SEQUENCE: 11

```
Asp Ile Gln Met Thr Gln Ser Pro Ala Ser Leu Ser Val Ser Val Gly
 1               5                  10                  15
Asp Thr Ile Thr Leu Thr Cys His Ala Ser Gln Asn Ile Asp Val Trp
            20                  25                  30
Leu Ser Trp Phe Gln Gln Lys Pro Gly Asn Ile Pro Lys Leu Leu Ile
            35                  40                  45
```

```
Tyr Lys Ala Ser Asn Leu His Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Gly Gly Gly Gly Ser
                100                 105                 110

Asp Ile Val Leu Thr Gln Ser Pro Ala Ser Leu Ala Val Ser Leu Gly
                115                 120                 125

Gln Arg Ala Thr Ile Ser Cys Arg Ala Ser Glu Ser Val Asp Ser Tyr
    130                 135                 140

Gly Gln Ser Tyr Met His Trp Tyr Gln Gln Lys Ala Gly Gln Pro Pro
145                 150                 155                 160

Lys Leu Leu Ile Tyr Leu Ala Ser Asn Leu Glu Ser Gly Val Pro Ala
                165                 170                 175

Arg Phe Ser Gly Ser Gly Ser Arg Thr Asp Phe Thr Leu Thr Ile Asp
                180                 185                 190

Pro Val Gln Ala Glu Asp Ala Ala Thr Tyr Tyr Cys Gln Gln Asn Ala
                195                 200                 205

Glu Asp Ser Arg Thr Phe Gly Gly Gly Thr Lys Leu Glu Ile Lys Arg
210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
                245                 250                 255

Pro Arg Glu Ala Lys Val Gln Trp Lys Val Asp Asn Ala Leu Gln Ser
                260                 265                 270

Gly Asn Ser Gln Glu Ser Val Thr Glu Gln Asp Ser Lys Asp Ser Thr
            275                 280                 285

Tyr Ser Leu Ser Ser Thr Leu Thr Leu Ser Lys Ala Asp Tyr Glu Lys
290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 12
<211> LENGTH: 335
<212> TYPE: PRT
<213> ORGANISM: Artificial Sequence
<220> FEATURE:
<223> OTHER INFORMATION: Light chain cross over double head construct
      IL4(G4S2)IL13CL

<400> SEQUENCE: 12

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
                20                  25                  30

Leu Ser Trp Phe Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80
```

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Gly Gly Gly Gly Ser
            100                 105                 110

Gly Gly Gly Gly Ser Asp Ile Val Leu Thr Gln Ser Pro Ala Ser Leu
        115                 120                 125

Ala Val Ser Leu Gly Gln Arg Ala Thr Ile Ser Cys Arg Ala Ser Glu
130                 135                 140

Ser Val Asp Ser Tyr Gly Gln Ser Tyr Met His Trp Tyr Gln Gln Lys
145                 150                 155                 160

Ala Gly Gln Pro Pro Lys Leu Leu Ile Tyr Leu Ala Ser Asn Leu Glu
                165                 170                 175

Ser Gly Val Pro Ala Arg Phe Ser Gly Ser Gly Ser Arg Thr Asp Phe
            180                 185                 190

Thr Leu Thr Ile Asp Pro Val Gln Ala Glu Asp Ala Ala Thr Tyr Tyr
        195                 200                 205

Cys Gln Gln Asn Ala Glu Asp Ser Arg Thr Phe Gly Gly Gly Thr Lys
    210                 215                 220

Leu Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
            260                 265                 270

Asn Ala Leu Gln Ser Gly Asn Ser Gln Glu Ser Val Thr Glu Gln Asp
        275                 280                 285

Ser Lys Asp Ser Thr Tyr Ser Leu Ser Ser Thr Leu Thr Leu Ser Lys
    290                 295                 300

Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335

<210> SEQ ID NO 13
<211> LENGTH: 583
<212> TYPE: PRT
<213> ORGANISM: Artificial Sequence
<220> FEATURE:
<223> OTHER INFORMATION: Heavy chain sequence for cross over dual V-Ig
      having code HC1

<400> SEQUENCE: 13

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr

```
                100             105             110
Ser Val Thr Val Ser Gly Gly Gly Gly Gly Gln Val Gln Leu
            115             120             125
Gln Gln Ser Gly Pro Glu Leu Val Lys Pro Gly Ala Ser Val Lys Ile
            130             135             140
Ser Cys Lys Ala Ser Gly Tyr Ser Phe Thr Ser Tyr Trp Ile His Trp
145             150             155             160
Ile Lys Gln Arg Pro Gly Gln Gly Leu Glu Trp Ile Gly Met Ile Asp
            165             170             175
Pro Ser Asp Gly Glu Thr Arg Leu Asn Gln Arg Phe Gln Gly Arg Ala
            180             185             190
Thr Leu Thr Val Asp Glu Ser Thr Ser Thr Ala Tyr Met Gln Leu Arg
            195             200             205
Ser Pro Thr Ser Glu Asp Ser Ala Val Tyr Tyr Cys Thr Arg Leu Lys
            210             215             220
Glu Tyr Gly Asn Tyr Asp Ser Phe Tyr Phe Asp Val Trp Gly Ala Gly
225             230             235             240
Thr Leu Val Thr Val Ser Ser Gly Gly Gly Gly Gly Gly Ala Ser
            245             250             255
Thr Lys Gly Pro Ser Val Phe Pro Leu Ala Pro Ser Ser Lys Ser Thr
            260             265             270
Ser Gly Gly Thr Ala Ala Leu Gly Cys Leu Val Lys Asp Tyr Phe Pro
            275             280             285
Glu Pro Val Thr Val Ser Trp Asn Ser Gly Ala Leu Thr Ser Gly Val
            290             295             300
His Thr Phe Pro Ala Val Leu Gln Ser Ser Gly Leu Tyr Ser Leu Ser
305             310             315             320
Ser Val Val Thr Val Pro Ser Ser Leu Gly Thr Gln Thr Tyr Ile
            325             330             335
Cys Asn Val Asn His Lys Pro Ser Asn Thr Lys Val Asp Lys Lys Val
            340             345             350
Glu Pro Lys Ser Cys Asp Lys Thr His Thr Cys Pro Pro Cys Pro Ala
            355             360             365
Pro Glu Leu Leu Gly Gly Pro Ser Val Phe Leu Phe Pro Pro Lys Pro
            370             375             380
Lys Asp Thr Leu Met Ile Ser Arg Thr Pro Glu Val Thr Cys Val Val
385             390             395             400
Val Asp Val Ser His Glu Asp Pro Glu Val Lys Phe Asn Trp Tyr Val
            405             410             415
Asp Gly Val Glu Val His Asn Ala Lys Thr Lys Pro Arg Glu Glu Gln
            420             425             430
Tyr Asn Ser Thr Tyr Arg Val Val Ser Val Leu Thr Val Leu His Gln
            435             440             445
Asp Trp Leu Asn Gly Lys Glu Tyr Lys Cys Lys Val Ser Asn Lys Ala
450             455             460
Leu Pro Ala Pro Ile Glu Lys Thr Ile Ser Lys Ala Lys Gly Gln Pro
465             470             475             480
Arg Glu Pro Gln Val Tyr Thr Leu Pro Pro Ser Arg Asp Glu Leu Thr
            485             490             495
Lys Asn Gln Val Ser Leu Thr Cys Leu Val Lys Gly Phe Tyr Pro Ser
            500             505             510
Asp Ile Ala Val Glu Trp Glu Ser Asn Gly Gln Pro Glu Asn Asn Tyr
            515             520             525
```

```
Lys Thr Thr Pro Pro Val Leu Asp Ser Asp Gly Ser Phe Phe Leu Tyr
            530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly
            580

<210> SEQ ID NO 14
<211> LENGTH: 580
<212> TYPE: PRT
<213> ORGANISM: Artificial Sequence
<220> FEATURE:
<223> OTHER INFORMATION: Heavy chain sequence for cross over dual V-Ig
      having code HC2

<400> SEQUENCE: 14

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
            35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser Gly Gly Gly Gly Gly Gln Val Gln Leu
            115                 120                 125

Gln Gln Ser Gly Pro Glu Leu Val Lys Pro Gly Ala Ser Val Lys Ile
    130                 135                 140

Ser Cys Lys Ala Ser Gly Tyr Ser Phe Thr Ser Tyr Trp Ile His Trp
145                 150                 155                 160

Ile Lys Gln Arg Pro Gly Gln Gly Leu Glu Trp Ile Gly Met Ile Asp
                165                 170                 175

Pro Ser Asp Gly Glu Thr Arg Leu Asn Gln Arg Phe Gln Gly Arg Ala
            180                 185                 190

Thr Leu Thr Val Asp Glu Ser Thr Ser Thr Ala Tyr Met Gln Leu Arg
            195                 200                 205

Ser Pro Thr Ser Glu Asp Ser Ala Val Tyr Tyr Cys Thr Arg Leu Lys
    210                 215                 220

Glu Tyr Gly Asn Tyr Asp Ser Phe Tyr Phe Asp Val Trp Gly Ala Gly
225                 230                 235                 240

Thr Leu Val Thr Val Ser Ser Gly Gly Gly Gly Ala Ser Thr Lys Gly
                245                 250                 255

Pro Ser Val Phe Pro Leu Ala Pro Ser Ser Lys Ser Thr Ser Gly Gly
            260                 265                 270

Thr Ala Ala Leu Gly Cys Leu Val Lys Asp Tyr Phe Pro Glu Pro Val
            275                 280                 285

Thr Val Ser Trp Asn Ser Gly Ala Leu Thr Ser Gly Val His Thr Phe
```

```
                290                 295                 300
Pro Ala Val Leu Gln Ser Ser Gly Leu Tyr Ser Leu Ser Ser Val Val
305                 310                 315                 320

Thr Val Pro Ser Ser Ser Leu Gly Thr Gln Thr Tyr Ile Cys Asn Val
                325                 330                 335

Asn His Lys Pro Ser Asn Thr Lys Val Asp Lys Val Glu Pro Lys
                340                 345                 350

Ser Cys Asp Lys Thr His Thr Cys Pro Pro Cys Pro Ala Pro Glu Leu
            355                 360                 365

Leu Gly Gly Pro Ser Val Phe Leu Phe Pro Pro Lys Pro Lys Asp Thr
        370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
                420                 425                 430

Thr Tyr Arg Val Val Ser Val Leu Thr Val Leu His Gln Asp Trp Leu
            435                 440                 445

Asn Gly Lys Glu Tyr Lys Cys Lys Val Ser Asn Lys Ala Leu Pro Ala
        450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Asp Glu Leu Thr Lys Asn Gln
                485                 490                 495

Val Ser Leu Thr Cys Leu Val Lys Gly Phe Tyr Pro Ser Asp Ile Ala
                500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Tyr Ser Lys Leu
        530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly
            580

<210> SEQ ID NO 15
<211> LENGTH: 579
<212> TYPE: PRT
<213> ORGANISM: Artificial Sequence
<220> FEATURE:
<223> OTHER INFORMATION: Heavy chain sequence for cross over dual V-Ig
      having code HC3

<400> SEQUENCE: 15

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
                20                  25                  30

Ser Ile Asn Trp Val Arg Gln Pro Pro Gly Lys Gly Leu Glu Trp Leu
            35                  40                  45

Gly Met Ile Trp Gly Asp Gly Arg Ile Asp Tyr Ala Asp Ala Leu Lys
        50                  55                  60
```

-continued

```
Ser Arg Leu Ser Ile Ser Lys Asp Ser Ser Lys Ser Gln Val Phe Leu
 65                  70                  75                  80

Glu Met Thr Ser Leu Arg Thr Asp Asp Thr Ala Thr Tyr Tyr Cys Ala
                 85                  90                  95

Arg Asp Gly Tyr Phe Pro Tyr Ala Met Asp Phe Trp Gly Gln Gly Thr
            100                 105                 110

Ser Val Thr Val Ser Ser Gly Gly Gln Val Gln Leu Gln Gln Ser Gly
        115                 120                 125

Pro Glu Leu Val Lys Pro Gly Ala Ser Val Lys Ile Ser Cys Lys Ala
130                 135                 140

Ser Gly Tyr Ser Phe Thr Ser Tyr Trp Ile His Trp Ile Lys Gln Arg
145                 150                 155                 160

Pro Gly Gln Gly Leu Glu Trp Ile Gly Met Ile Asp Pro Ser Asp Gly
                165                 170                 175

Glu Thr Arg Leu Asn Gln Arg Phe Gln Gly Arg Ala Thr Leu Thr Val
            180                 185                 190

Asp Glu Ser Thr Ser Thr Ala Tyr Met Gln Leu Arg Ser Pro Thr Ser
        195                 200                 205

Glu Asp Ser Ala Val Tyr Tyr Cys Thr Arg Leu Lys Glu Tyr Gly Asn
210                 215                 220

Tyr Asp Ser Phe Tyr Phe Asp Val Trp Gly Ala Gly Thr Leu Val Thr
225                 230                 235                 240

Val Ser Ser Gly Gly Gly Gly Gly Ala Ser Thr Lys Gly Pro
                245                 250                 255

Ser Val Phe Pro Leu Ala Pro Ser Ser Lys Ser Thr Ser Gly Gly Thr
                260                 265                 270

Ala Ala Leu Gly Cys Leu Val Lys Asp Tyr Phe Pro Glu Pro Val Thr
            275                 280                 285

Val Ser Trp Asn Ser Gly Ala Leu Thr Ser Gly Val His Thr Phe Pro
        290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Gln Thr Tyr Ile Cys Asn Val Asn
                325                 330                 335

His Lys Pro Ser Asn Thr Lys Val Asp Lys Lys Val Glu Pro Lys Ser
            340                 345                 350

Cys Asp Lys Thr His Thr Cys Pro Pro Cys Pro Ala Pro Glu Leu Leu
        355                 360                 365

Gly Gly Pro Ser Val Phe Leu Phe Pro Pro Lys Pro Lys Asp Thr Leu
370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
                405                 410                 415

Val His Asn Ala Lys Thr Lys Pro Arg Glu Glu Gln Tyr Asn Ser Thr
            420                 425                 430

Tyr Arg Val Val Ser Val Leu Thr Val Leu His Gln Asp Trp Leu Asn
        435                 440                 445

Gly Lys Glu Tyr Lys Cys Lys Val Ser Asn Lys Ala Leu Pro Ala Pro
        450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Asp Glu Leu Thr Lys Asn Gln Val
```

```
                        485                 490                 495
Ser Leu Thr Cys Leu Val Lys Gly Phe Tyr Pro Ser Asp Ile Ala Val
                500                 505                 510

Glu Trp Glu Ser Asn Gly Gln Pro Glu Asn Asn Tyr Lys Thr Thr Pro
            515                 520                 525

Pro Val Leu Asp Ser Asp Gly Ser Phe Phe Leu Tyr Ser Lys Leu Thr
        530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly

<210> SEQ ID NO 16
<211> LENGTH: 576
<212> TYPE: PRT
<213> ORGANISM: Artificial Sequence
<220> FEATURE:
<223> OTHER INFORMATION: Heavy chain sequence for cross over dual V-Ig
      having code HC4

<400> SEQUENCE: 16

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
                20                  25                  30

Ser Ile Asn Trp Val Arg Gln Pro Pro Gly Lys Gly Leu Glu Trp Leu
            35                  40                  45

Gly Met Ile Trp Gly Asp Gly Arg Ile Asp Tyr Ala Asp Ala Leu Lys
        50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
                100                 105                 110

Ser Val Thr Val Ser Ser Gly Gly Gln Val Gln Leu Gln Gln Ser Gly
            115                 120                 125

Pro Glu Leu Val Lys Pro Gly Ala Ser Val Lys Ile Ser Cys Lys Ala
        130                 135                 140

Ser Gly Tyr Ser Phe Thr Ser Tyr Trp Ile His Trp Ile Lys Gln Arg
145                 150                 155                 160

Pro Gly Gln Gly Leu Glu Trp Ile Gly Met Ile Asp Pro Ser Asp Gly
                165                 170                 175

Glu Thr Arg Leu Asn Gln Arg Phe Gln Gly Arg Ala Thr Leu Thr Val
                180                 185                 190

Asp Glu Ser Thr Ser Thr Ala Tyr Met Gln Leu Arg Ser Pro Thr Ser
            195                 200                 205

Glu Asp Ser Ala Val Tyr Tyr Cys Thr Arg Leu Lys Glu Tyr Gly Asn
        210                 215                 220

Tyr Asp Ser Phe Tyr Phe Asp Val Trp Gly Ala Gly Thr Leu Val Thr
225                 230                 235                 240

Val Ser Ser Gly Gly Gly Gly Ala Ser Thr Lys Gly Pro Ser Val Phe
                245                 250                 255

Pro Leu Ala Pro Ser Ser Lys Ser Thr Ser Gly Gly Thr Ala Ala Leu
```

```
               260                 265                 270
Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
        290                 295                 300

Gln Ser Ser Gly Leu Tyr Ser Leu Ser Ser Val Val Thr Val Pro Ser
305                 310                 315                 320

Ser Ser Leu Gly Thr Gln Thr Tyr Ile Cys Asn Val Asn His Lys Pro
                325                 330                 335

Ser Asn Thr Lys Val Asp Lys Lys Val Glu Pro Lys Ser Cys Asp Lys
            340                 345                 350

Thr His Thr Cys Pro Pro Cys Pro Ala Pro Glu Leu Leu Gly Gly Pro
        355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
            420                 425                 430

Val Ser Val Leu Thr Val Leu His Gln Asp Trp Leu Asn Gly Lys Glu
        435                 440                 445

Tyr Lys Cys Lys Val Ser Asn Lys Ala Leu Pro Ala Pro Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Thr
                485                 490                 495

Cys Leu Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Lys Leu Thr Val Asp Lys
    530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

<210> SEQ ID NO 17
<211> LENGTH: 581
<212> TYPE: PRT
<213> ORGANISM: Artificial Sequence
<220> FEATURE:
<223> OTHER INFORMATION: Heavy chain sequence for cross over dual V-Ig
      having code HC5

<400> SEQUENCE: 17

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45
```

```
Gly Met Ile Trp Gly Asp Gly Arg Ile Asp Tyr Ala Asp Ala Leu Lys
 50              55                  60

Ser Arg Leu Ser Ile Ser Lys Asp Ser Ser Lys Ser Gln Val Phe Leu
 65              70                  75                      80

Glu Met Thr Ser Leu Arg Thr Asp Asp Thr Ala Thr Tyr Tyr Cys Ala
                 85              90                  95

Arg Asp Gly Tyr Phe Pro Tyr Ala Met Asp Phe Trp Gly Gln Gly Thr
            100             105                 110

Ser Val Thr Val Ser Ser Gly Gly Gly Gln Val Gln Leu Gln Gln
            115             120             125

Ser Gly Pro Glu Leu Val Lys Pro Gly Ala Ser Val Lys Ile Ser Cys
        130             135                 140

Lys Ala Ser Gly Tyr Ser Phe Thr Ser Tyr Trp Ile His Trp Ile Lys
145             150             155                         160

Gln Arg Pro Gly Gln Gly Leu Glu Trp Ile Gly Met Ile Asp Pro Ser
            165             170                 175

Asp Gly Glu Thr Arg Leu Asn Gln Arg Phe Gln Gly Arg Ala Thr Leu
            180             185                 190

Thr Val Asp Glu Ser Thr Ser Thr Ala Tyr Met Gln Leu Arg Ser Pro
        195             200             205

Thr Ser Glu Asp Ser Ala Val Tyr Tyr Cys Thr Arg Leu Lys Glu Tyr
        210             215             220

Gly Asn Tyr Asp Ser Phe Tyr Phe Asp Val Trp Gly Ala Gly Thr Leu
225             230             235                         240

Val Thr Val Ser Ser Gly Gly Gly Gly Gly Gly Ala Ser Thr Lys
            245             250             255

Gly Pro Ser Val Phe Pro Leu Ala Pro Ser Ser Lys Ser Thr Ser Gly
        260             265             270

Gly Thr Ala Ala Leu Gly Cys Leu Val Lys Asp Tyr Phe Pro Glu Pro
        275             280             285

Val Thr Val Ser Trp Asn Ser Gly Ala Leu Thr Ser Gly Val His Thr
        290             295             300

Phe Pro Ala Val Leu Gln Ser Ser Gly Leu Tyr Ser Leu Ser Ser Val
305             310             315                         320

Val Thr Val Pro Ser Ser Ser Leu Gly Thr Gln Thr Tyr Ile Cys Asn
                325             330             335

Val Asn His Lys Pro Ser Asn Thr Lys Val Asp Lys Lys Val Glu Pro
            340             345             350

Lys Ser Cys Asp Lys Thr His Thr Cys Pro Pro Cys Pro Ala Pro Glu
        355             360             365

Leu Leu Gly Gly Pro Ser Val Phe Leu Phe Pro Pro Lys Pro Lys Asp
        370             375             380

Thr Leu Met Ile Ser Arg Thr Pro Glu Val Thr Cys Val Val Val Asp
385             390             395                         400

Val Ser His Glu Asp Pro Glu Val Lys Phe Asn Trp Tyr Val Asp Gly
            405             410             415

Val Glu Val His Asn Ala Lys Thr Lys Pro Arg Glu Glu Gln Tyr Asn
            420             425             430

Ser Thr Tyr Arg Val Val Ser Val Leu Thr Val Leu His Gln Asp Trp
            435             440             445

Leu Asn Gly Lys Glu Tyr Lys Cys Lys Val Ser Asn Lys Ala Leu Pro
450             455             460

Ala Pro Ile Glu Lys Thr Ile Ser Lys Ala Lys Gly Gln Pro Arg Glu
```

```
                        465                 470                 475                 480
Pro Gln Val Tyr Thr Leu Pro Pro Ser Arg Asp Glu Leu Thr Lys Asn
                485                 490                 495

Gln Val Ser Leu Thr Cys Leu Val Lys Gly Phe Tyr Pro Ser Asp Ile
                500                 505                 510

Ala Val Glu Trp Glu Ser Asn Gly Gln Pro Glu Asn Asn Tyr Lys Thr
                515                 520                 525

Thr Pro Pro Val Leu Asp Ser Asp Gly Ser Phe Phe Leu Tyr Ser Lys
                530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly
                580

<210> SEQ ID NO 18
<211> LENGTH: 578
<212> TYPE: PRT
<213> ORGANISM: Artificial Sequence
<220> FEATURE:
<223> OTHER INFORMATION: Heavy chain for cross over dual V-Ig having
      code HC6

<400> SEQUENCE: 18

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
                20                  25                  30

Ser Ile Asn Trp Val Arg Gln Pro Pro Gly Lys Gly Leu Glu Trp Leu
            35                  40                  45

Gly Met Ile Trp Gly Asp Gly Arg Ile Asp Tyr Ala Asp Ala Leu Lys
        50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
                100                 105                 110

Ser Val Thr Val Ser Ser Gly Gly Gly Gly Gln Val Gln Leu Gln Gln
                115                 120                 125

Ser Gly Pro Glu Leu Val Lys Pro Gly Ala Ser Val Lys Ile Ser Cys
                130                 135                 140

Lys Ala Ser Gly Tyr Ser Phe Thr Ser Tyr Trp Ile His Trp Ile Lys
145                 150                 155                 160

Gln Arg Pro Gly Gln Gly Leu Glu Trp Ile Gly Met Ile Asp Pro Ser
                165                 170                 175

Asp Gly Glu Thr Arg Leu Asn Gln Arg Phe Gln Gly Arg Ala Thr Leu
                180                 185                 190

Thr Val Asp Glu Ser Thr Ser Thr Ala Tyr Met Gln Leu Arg Ser Pro
                195                 200                 205

Thr Ser Glu Asp Ser Ala Val Tyr Tyr Cys Thr Arg Leu Lys Glu Tyr
                210                 215                 220

Gly Asn Tyr Asp Ser Phe Tyr Phe Asp Val Trp Gly Ala Gly Thr Leu
225                 230                 235                 240
```

```
Val Thr Val Ser Ser Gly Gly Gly Gly Ala Ser Thr Lys Gly Pro Ser
            245                 250                 255

Val Phe Pro Leu Ala Pro Ser Ser Lys Ser Thr Ser Gly Gly Thr Ala
        260                 265                 270

Ala Leu Gly Cys Leu Val Lys Asp Tyr Phe Pro Glu Pro Val Thr Val
        275                 280                 285

Ser Trp Asn Ser Gly Ala Leu Thr Ser Gly Val His Thr Phe Pro Ala
        290                 295                 300

Val Leu Gln Ser Ser Gly Leu Tyr Ser Leu Ser Ser Val Val Thr Val
305                 310                 315                 320

Pro Ser Ser Ser Leu Gly Thr Gln Thr Tyr Ile Cys Asn Val Asn His
                325                 330                 335

Lys Pro Ser Asn Thr Lys Val Asp Lys Lys Val Glu Pro Lys Ser Cys
            340                 345                 350

Asp Lys Thr His Thr Cys Pro Pro Cys Pro Ala Pro Glu Leu Leu Gly
        355                 360                 365

Gly Pro Ser Val Phe Leu Phe Pro Pro Lys Pro Lys Asp Thr Leu Met
        370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Asn Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
        450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
                485                 490                 495

Leu Thr Cys Leu Val Lys Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
        515                 520                 525

Val Leu Asp Ser Asp Gly Ser Phe Phe Leu Tyr Ser Lys Leu Thr Val
        530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
                565                 570                 575

Pro Gly

<210> SEQ ID NO 19
<211> LENGTH: 328
<212> TYPE: PRT
<213> ORGANISM: Artificial Sequence
<220> FEATURE:
<223> OTHER INFORMATION: Light chain sequence for cross over dual V-Ig
      having code LC1

<400> SEQUENCE: 19

Asp Ile Gln Met Thr Gln Ser Pro Ala Ser Leu Ser Val Ser Val Gly
1               5                   10                  15
```

```
Asp Thr Ile Thr Leu Thr Cys His Ala Ser Gln Asn Ile Asp Val Trp
            20                  25                  30
Leu Ser Trp Phe Gln Gln Lys Pro Gly Asn Ile Pro Lys Leu Leu Ile
        35                  40                  45
Tyr Lys Ala Ser Asn Leu His Thr Gly Val Pro Ser Arg Phe Ser Gly
 50                  55                  60
Ser Gly Ser Gly Thr Gly Phe Thr Leu Thr Ile Ser Ser Leu Gln Pro
65                  70                  75                  80
Glu Asp Ile Ala Thr Tyr Tyr Cys Gln Gln Ala His Ser Tyr Pro Phe
                85                  90                  95
Thr Phe Gly Gly Gly Thr Lys Leu Glu Ile Lys Gly Gly Gly Asp Ile
            100                 105                 110
Val Leu Thr Gln Ser Pro Ala Ser Leu Ala Val Ser Leu Gly Gln Arg
        115                 120                 125
Ala Thr Ile Ser Cys Arg Ala Ser Glu Ser Val Asp Ser Tyr Gly Gln
130                 135                 140
Ser Tyr Met His Trp Tyr Gln Gln Lys Ala Gly Gln Pro Pro Lys Leu
145                 150                 155                 160
Leu Ile Tyr Leu Ala Ser Asn Leu Glu Ser Gly Val Pro Ala Arg Phe
                165                 170                 175
Ser Gly Ser Gly Ser Arg Thr Asp Phe Thr Leu Thr Ile Asp Pro Val
            180                 185                 190
Gln Ala Glu Asp Ala Ala Thr Tyr Tyr Cys Gln Gln Asn Ala Glu Asp
        195                 200                 205
Ser Arg Thr Phe Gly Gly Gly Thr Lys Leu Glu Ile Lys Arg Thr Val
210                 215                 220
Ala Ala Pro Ser Val Phe Ile Phe Pro Pro Ser Asp Glu Gln Leu Lys
225                 230                 235                 240
Ser Gly Thr Ala Ser Val Val Cys Leu Leu Asn Asn Phe Tyr Pro Arg
                245                 250                 255
Glu Ala Lys Val Gln Trp Lys Val Asp Asn Ala Leu Gln Ser Gly Asn
            260                 265                 270
Ser Gln Glu Ser Val Thr Glu Gln Asp Ser Lys Asp Ser Thr Tyr Ser
        275                 280                 285
Leu Ser Ser Thr Leu Thr Leu Ser Lys Ala Asp Tyr Glu Lys His Lys
290                 295                 300
Val Tyr Ala Cys Glu Val Thr His Gln Gly Leu Ser Ser Pro Val Thr
305                 310                 315                 320
Lys Ser Phe Asn Arg Gly Glu Cys
                325

<210> SEQ ID NO 20
<211> LENGTH: 326
<212> TYPE: PRT
<213> ORGANISM: Artificial Sequence
<220> FEATURE:
<223> OTHER INFORMATION: Light chain sequence for cross over dual V-Ig
      having code LC2

<400> SEQUENCE: 20

Asp Ile Gln Met Thr Gln Ser Pro Ala Ser Leu Ser Val Ser Val Gly
1               5                   10                  15
Asp Thr Ile Thr Leu Thr Cys His Ala Ser Gln Asn Ile Asp Val Trp
            20                  25                  30
Leu Ser Trp Phe Gln Gln Lys Pro Gly Asn Ile Pro Lys Leu Leu Ile
        35                  40                  45
```

Tyr Lys Ala Ser Asn Leu His Thr Gly Val Pro Ser Arg Phe Ser Gly
         50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Ala His Ser Tyr Pro Phe
                 85                  90                  95

Thr Phe Gly Gly Gly Thr Lys Leu Glu Ile Lys Gly Asp Ile Val Leu
                100                 105                 110

Thr Gln Ser Pro Ala Ser Leu Ala Val Ser Leu Gly Gln Arg Ala Thr
                115                 120                 125

Ile Ser Cys Arg Ala Ser Glu Ser Val Asp Ser Tyr Gly Gln Ser Tyr
        130                 135                 140

Met His Trp Tyr Gln Gln Lys Ala Gly Gln Pro Pro Lys Leu Leu Ile
145                 150                 155                 160

Tyr Leu Ala Ser Asn Leu Glu Ser Gly Val Pro Ala Arg Phe Ser Gly
                165                 170                 175

Ser Gly Ser Arg Thr Asp Phe Thr Leu Thr Ile Asp Pro Val Gln Ala
                180                 185                 190

Glu Asp Ala Ala Thr Tyr Tyr Cys Gln Gln Asn Ala Glu Asp Ser Arg
                195                 200                 205

Thr Phe Gly Gly Gly Thr Lys Leu Glu Ile Lys Arg Thr Val Ala Ala
                210                 215                 220

Pro Ser Val Phe Ile Phe Pro Pro Ser Asp Glu Gln Leu Lys Ser Gly
225                 230                 235                 240

Thr Ala Ser Val Val Cys Leu Leu Asn Asn Phe Tyr Pro Arg Glu Ala
                245                 250                 255

Lys Val Gln Trp Lys Val Asp Asn Ala Leu Gln Ser Gly Asn Ser Gln
                260                 265                 270

Glu Ser Val Thr Glu Gln Asp Ser Lys Asp Ser Thr Tyr Ser Leu Ser
                275                 280                 285

Ser Thr Leu Thr Leu Ser Lys Ala Asp Tyr Glu Lys His Lys Val Tyr
290                 295                 300

Ala Cys Glu Val Thr His Gln Gly Leu Ser Ser Pro Val Thr Lys Ser
305                 310                 315                 320

Phe Asn Arg Gly Glu Cys
                325

<210> SEQ ID NO 21
<211> LENGTH: 330
<212> TYPE: PRT
<213> ORGANISM: Artificial Sequence
<220> FEATURE:
<223> OTHER INFORMATION: Light chain sequence for cross over dual V-Ig
      having code LC3

<400> SEQUENCE: 21

Asp Ile Gln Met Thr Gln Ser Pro Ala Ser Leu Ser Val Ser Val Gly
 1               5                  10                  15

Asp Thr Ile Thr Leu Thr Cys His Ala Ser Gln Asn Ile Asp Val Trp
                 20                  25                  30

Leu Ser Trp Phe Gln Gln Lys Pro Gly Asn Ile Pro Lys Leu Leu Ile
                 35                  40                  45

Tyr Lys Ala Ser Asn Leu His Thr Gly Val Pro Ser Arg Phe Ser Gly
         50                  55                  60

Ser Gly Ser Gly Thr Gly Phe Thr Leu Thr Ile Ser Ser Leu Gln Pro

```
                65                  70                  75                  80
Glu Asp Ile Ala Thr Tyr Tyr Cys Gln Gln Ala His Ser Tyr Pro Phe
                    85                  90                  95

Thr Phe Gly Gly Gly Thr Lys Leu Glu Ile Lys Gly Gly Gly Asp Ile
                100                 105                 110

Val Leu Thr Gln Ser Pro Ala Ser Leu Ala Val Ser Leu Gly Gln Arg
                115                 120                 125

Ala Thr Ile Ser Cys Arg Ala Ser Glu Ser Val Asp Ser Tyr Gly Gln
            130                 135                 140

Ser Tyr Met His Trp Tyr Gln Gln Lys Ala Gly Gln Pro Pro Lys Leu
145                 150                 155                 160

Leu Ile Tyr Leu Ala Ser Asn Leu Glu Ser Gly Val Pro Ala Arg Phe
                165                 170                 175

Ser Gly Ser Gly Ser Arg Thr Asp Phe Thr Leu Thr Ile Asp Pro Val
                180                 185                 190

Gln Ala Glu Asp Ala Ala Thr Tyr Tyr Cys Gln Gln Asn Ala Glu Asp
                195                 200                 205

Ser Arg Thr Phe Gly Gly Gly Thr Lys Leu Glu Ile Lys Gly Gly Arg
            210                 215                 220

Thr Val Ala Ala Pro Ser Val Phe Ile Phe Pro Pro Ser Asp Glu Gln
225                 230                 235                 240

Leu Lys Ser Gly Thr Ala Ser Val Val Cys Leu Leu Asn Asn Phe Tyr
                245                 250                 255

Pro Arg Glu Ala Lys Val Gln Trp Lys Val Asp Asn Ala Leu Gln Ser
                260                 265                 270

Gly Asn Ser Gln Glu Ser Val Thr Glu Gln Asp Ser Lys Asp Ser Thr
            275                 280                 285

Tyr Ser Leu Ser Ser Thr Leu Thr Leu Ser Lys Ala Asp Tyr Glu Lys
                290                 295                 300

His Lys Val Tyr Ala Cys Glu Val Thr His Gln Gly Leu Ser Ser Pro
305                 310                 315                 320

Val Thr Lys Ser Phe Asn Arg Gly Glu Cys
                325                 330

<210> SEQ ID NO 22
<211> LENGTH: 328
<212> TYPE: PRT
<213> ORGANISM: Artificial Sequence
<220> FEATURE:
<223> OTHER INFORMATION: Light chain sequence for cross over dual V-Ig
      having code LC4

<400> SEQUENCE: 22

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
                20                  25                  30

Leu Ser Trp Phe Gln Gln Lys Pro Gly Asn Ile Pro Lys Leu Leu Ile
                35                  40                  45

Tyr Lys Ala Ser Asn Leu His Thr Gly Val Pro Ser Arg Phe Ser Gly
            50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95
```

-continued

```
Thr Phe Gly Gly Gly Thr Lys Leu Glu Ile Lys Gly Asp Ile Val Leu
            100                 105                 110

Thr Gln Ser Pro Ala Ser Leu Ala Val Ser Leu Gly Gln Arg Ala Thr
        115                 120                 125

Ile Ser Cys Arg Ala Ser Glu Ser Val Asp Ser Tyr Gly Gln Ser Tyr
    130                 135                 140

Met His Trp Tyr Gln Gln Lys Ala Gly Gln Pro Pro Lys Leu Leu Ile
145                 150                 155                 160

Tyr Leu Ala Ser Asn Leu Glu Ser Gly Val Pro Ala Arg Phe Ser Gly
                165                 170                 175

Ser Gly Ser Arg Thr Asp Phe Thr Leu Thr Ile Asp Pro Val Gln Ala
            180                 185                 190

Glu Asp Ala Ala Thr Tyr Tyr Cys Gln Gln Asn Ala Glu Asp Ser Arg
        195                 200                 205

Thr Phe Gly Gly Gly Thr Lys Leu Glu Ile Lys Gly Gly Arg Thr Val
    210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
            260                 265                 270

Ser Gln Glu Ser Val Thr Glu Gln Asp Ser Lys Asp Ser Thr Tyr Ser
        275                 280                 285

Leu Ser Ser Thr Leu Thr Leu Ser Lys Ala Asp Tyr Glu Lys His Lys
    290                 295                 300

Val Tyr Ala Cys Glu Val Thr His Gln Gly Leu Ser Ser Pro Val Thr
305                 310                 315                 320

Lys Ser Phe Asn Arg Gly Glu Cys
                325

<210> SEQ ID NO 23
<211> LENGTH: 107
<212> TYPE: PRT
<213> ORGANISM: Homo sapiens

<400> SEQUENCE: 23

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 24
<211> LENGTH: 329
<212> TYPE: PRT
<213> ORGANISM: Homo sapiens
```

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 25
<211> LENGTH: 4
<212> TYPE: PRT
<213> ORGANISM: Artificial Sequence
<220> FEATURE:
<223> OTHER INFORMATION: Peptide linker with four glycine residues

<400> SEQUENCE: 25

Gly Gly Gly Gly
1

```
<210> SEQ ID NO 26
<211> LENGTH: 5
<212> TYPE: PRT
<213> ORGANISM: Artificial Sequence
<220> FEATURE:
<223> OTHER INFORMATION: Peptide linker with 5 glycine amino acid
      residues

<400> SEQUENCE: 26

Gly Gly Gly Gly Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Peptide linker with 6 glycine amino acid
      residues.

<400> SEQUENCE: 27

Gly Gly Gly Gly Gly Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Peptide linker with seven glycine amino acid
      residues.

<400> SEQUENCE: 28

Gly Gly Gly Gly Gly Gly Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Peptide linker with eight glycine amino acid
      residues.

<400> SEQUENCE: 29

Gly Gly Gly Gly Gly Gly Gly Gly
1               5

<210> SEQ ID NO 30
<211> LENGTH: 5
<212> TYPE: PRT
<213> ORGANISM: Artificial Sequence
<220> FEATURE:
<223> OTHER INFORMATION: artificial peptide linker

<400> SEQUENCE: 30

Gly Gly Gly Gly Ser
1               5

<210> SEQ ID NO 31
<211> LENGTH: 10
<212> TYPE: PRT
<213> ORGANISM: Artificial Sequence
<220> FEATURE:
<223> OTHER INFORMATION: artificial peptide linker

<400> SEQUENCE: 31
```

```
Gly Gly Gly Gly Ser Gly Gly Gly Ser
1               5                   10
```

<210> SEQ ID NO 32
<211> LENGTH: 582
<212> TYPE: PRT
<213> ORGANISM: Artificial Sequence
<220> FEATURE:
<223> OTHER INFORMATION: Heavy chain sequence for cross over dual V-Ig having code HC10

<400> SEQUENCE: 32

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser Gly Glu Val Gln Leu Val Glu Ser Gly Gly Gly Leu Val Gln
    130                 135                 140

Pro Gly Gly Ser Leu Arg Leu Ser Cys Ala Ala Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Gly Asp Gly Phe Tyr Ala Met Asp Tyr
225                 230                 235                 240

Trp Gly Gln Gly Thr Leu Val Thr Val Ser Ser Gly Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Lys Val Glu
            340                 345                 350
```

-continued

Pro Lys Ser Cys Asp Lys Thr His Thr Cys Pro Pro Cys Pro Ala Pro
            355                 360                 365

Glu Leu Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Asp Glu Leu Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly
            580

<210> SEQ ID NO 33
<211> LENGTH: 582
<212> TYPE: PRT
<213> ORGANISM: Artificial Sequence
<220> FEATURE:
<223> OTHER INFORMATION: Heavy chain sequence for cross over dual V-Ig
      having code HC11

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Glu Val Gln Leu Val Gln Ser

```
                115                     120                     125
        Gly Ala Glu Val Lys Lys Pro Gly Ser Ser Val Lys Val Ser Cys Lys
            130                     135                     140
        Ala Ser Gly Gly Thr Phe Ser Ser Tyr Ala Ile Ser Trp Val Arg Gln
        145                     150                     155                 160
        Ala Pro Gly Gln Gly Leu Glu Trp Met Gly Ile Ile Pro Ile Phe
                            165                     170                     175
        Gly Thr Ala Asn Tyr Ala Gln Lys Phe Gln Gly Arg Val Thr Ile Thr
                        180                     185                     190
        Ala Asp Lys Ser Thr Ser Thr Ala Tyr Met Glu Leu Ser Ser Leu Arg
                    195                     200                     205
        Ser Glu Asp Thr Ala Val Tyr Tyr Cys Ala Arg Ala Pro Leu Arg Phe
                210                     215                     220
        Leu Glu Trp Ser Thr Gln Asp His Tyr Tyr Tyr Tyr Met Asp Val
        225                     230                     235                 240
        Trp Gly Lys Gly Thr Thr Val Thr Val Ser Ser Gly Gly Ala Ser Thr
                            245                     250                     255
        Lys Gly Pro Ser Val Phe Pro Leu Ala Pro Ser Ser Lys Ser Thr Ser
                        260                     265                     270
        Gly Gly Thr Ala Ala Leu Gly Cys Leu Val Lys Asp Tyr Phe Pro Glu
                    275                     280                     285
        Pro Val Thr Val Ser Trp Asn Ser Gly Ala Leu Thr Ser Gly Val His
                290                     295                     300
        Thr Phe Pro Ala Val Leu Gln Ser Ser Gly Leu Tyr Ser Leu Ser Ser
        305                     310                     315                 320
        Val Val Thr Val Pro Ser Ser Ser Leu Gly Thr Gln Thr Tyr Ile Cys
                            325                     330                     335
        Asn Val Asn His Lys Pro Ser Asn Thr Lys Val Asp Lys Lys Val Glu
                        340                     345                     350
        Pro Lys Ser Cys Asp Lys Thr His Thr Cys Pro Pro Cys Pro Ala Pro
                    355                     360                     365
        Glu Leu Leu Gly Gly Pro Ser Val Phe Leu Phe Pro Pro Lys Pro Lys
                370                     375                     380
        Asp Thr Leu Met Ile Ser Arg Thr Pro Glu Val Thr Cys Val Val Val
        385                     390                     395                 400
        Asp Val Ser His Glu Asp Pro Glu Val Lys Phe Asn Trp Tyr Val Asp
                            405                     410                     415
        Gly Val Glu Val His Asn Ala Lys Thr Lys Pro Arg Glu Glu Gln Tyr
                        420                     425                     430
        Asn Ser Thr Tyr Arg Val Val Ser Val Leu Thr Val Leu His Gln Asp
                    435                     440                     445
        Trp Leu Asn Gly Lys Glu Tyr Lys Cys Lys Val Ser Asn Lys Ala Leu
                450                     455                     460
        Pro Ala Pro Ile Glu Lys Thr Ile Ser Lys Ala Lys Gly Gln Pro Arg
        465                     470                     475                 480
        Glu Pro Gln Val Tyr Thr Leu Pro Pro Ser Arg Asp Glu Leu Thr Lys
                            485                     490                     495
        Asn Gln Val Ser Leu Thr Cys Leu Val Lys Gly Phe Tyr Pro Ser Asp
                        500                     505                     510
        Ile Ala Val Glu Trp Glu Ser Asn Gly Gln Pro Glu Asn Asn Tyr Lys
                    515                     520                     525
        Thr Thr Pro Pro Val Leu Asp Ser Asp Gly Ser Phe Phe Leu Tyr Ser
                530                     535                     540
```

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly
            580

<210> SEQ ID NO 34
<211> LENGTH: 571
<212> TYPE: PRT
<213> ORGANISM: Artificial Sequence
<220> FEATURE:
<223> OTHER INFORMATION: Heavy chain sequence for cross over dual V-Ig
      having code HC12

<400> SEQUENCE: 34

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Ala Met His Trp Val Arg Gln Ala Pro Gly Lys Gly Leu Glu Trp Ile
        35                  40                  45

Ser Val Ile Asp Thr Arg Gly Ala Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Leu Gly Asn Phe Tyr Tyr Gly Met Asp Val Trp Gly Gln Gly Thr
            100                 105                 110

Thr Val Thr Val Ser Ser Gly Gln Val Gln Leu Gln Glu Ser Gly Pro
        115                 120                 125

Gly Leu Val Lys Pro Ser Gln Thr Leu Ser Leu Thr Cys Thr Val Ser
    130                 135                 140

Gly Gly Ser Ile Ser Ser Gly Asp Tyr Tyr Trp Ser Trp Ile Arg Gln
145                 150                 155                 160

Pro Pro Gly Lys Gly Leu Glu Trp Ile Gly Tyr Ile Tyr Tyr Ser Gly
                165                 170                 175

Ser Thr Asp Tyr Asn Pro Ser Leu Lys Ser Arg Val Thr Met Ser Val
            180                 185                 190

Asp Thr Ser Lys Asn Gln Phe Ser Leu Lys Val Asn Ser Val Thr Ala
        195                 200                 205

Ala Asp Thr Ala Val Tyr Tyr Cys Ala Arg Val Ser Ile Phe Gly Val
    210                 215                 220

Gly Thr Phe Asp Tyr Trp Gly Gln Gly Thr Leu Val Thr Val Ser Ser
225                 230                 235                 240

Gly Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr

```
                    305                 310                 315                 320
Gln Thr Tyr Ile Cys Asn Val Asn His Lys Pro Ser Asn Thr Lys Val
                325                 330                 335

Asp Lys Lys Val Glu Pro Lys Ser Cys Asp Lys Thr His Thr Cys Pro
                340                 345                 350

Pro Cys Pro Ala Pro Glu Leu Leu Gly Gly Pro Ser Val Phe Leu Phe
                355                 360                 365

Pro Pro Lys Pro Lys Asp Thr Leu Met Ile Ser Arg Thr Pro Glu Val
                370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
                420                 425                 430

Val Leu His Gln Asp Trp Leu Asn Gly Lys Glu Tyr Lys Cys Lys Val
                435                 440                 445

Ser Asn Lys Ala Leu Pro Ala Pro Ile Glu Lys Thr Ile Ser Lys Ala
                450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
                500                 505                 510

Glu Asn Asn Tyr Lys Thr Thr Pro Pro Val Leu Asp Ser Asp Gly Ser
                515                 520                 525

Phe Phe Leu Tyr Ser Lys Leu Thr Val Asp Lys Ser Arg Trp Gln Gln
                530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 35
<211> LENGTH: 571
<212> TYPE: PRT
<213> ORGANISM: Artificial Sequence
<220> FEATURE:
<223> OTHER INFORMATION: Heavy chain sequence for cross over dual V-Ig
      having code HC13

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln Pro Pro Gly Lys Gly Leu Glu
                35                  40                  45

Trp Ile Gly Tyr Ile Tyr Tyr Ser Gly Ser Thr Asp Tyr Asn Pro Ser
                50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95
```

-continued

```
Cys Ala Arg Val Ser Ile Phe Gly Val Gly Thr Phe Asp Tyr Trp Gly
                100                 105                 110
Gln Gly Thr Leu Val Thr Val Ser Ser Gly Glu Val Gln Leu Val Gln
            115                 120                 125
Ser Gly Gly Gly Leu Val Lys Pro Gly Gly Ser Leu Arg Leu Ser Cys
        130                 135                 140
Ala Ala Ser Gly Phe Thr Phe Ser Ser Phe Ala Met His Trp Val Arg
145                 150                 155                 160
Gln Ala Pro Gly Lys Gly Leu Glu Trp Ile Ser Val Ile Asp Thr Arg
                165                 170                 175
Gly Ala Thr Tyr Tyr Ala Asp Ser Val Lys Gly Arg Phe Thr Ile Ser
            180                 185                 190
Arg Asp Asn Ala Lys Asn Ser Leu Tyr Leu Gln Met Asn Ser Leu Arg
        195                 200                 205
Ala Glu Asp Thr Ala Val Tyr Tyr Cys Ala Arg Leu Gly Asn Phe Tyr
210                 215                 220
Tyr Gly Met Asp Val Trp Gly Gln Gly Thr Thr Val Thr Val Ser Ser
225                 230                 235                 240
Gly Gly Ala Ser Thr Lys Gly Pro Ser Val Phe Pro Leu Ala Pro Ser
            245                 250                 255
Ser Lys Ser Thr Ser Gly Gly Thr Ala Ala Leu Gly Cys Leu Val Lys
        260                 265                 270
Asp Tyr Phe Pro Glu Pro Val Thr Val Ser Trp Asn Ser Gly Ala Leu
            275                 280                 285
Thr Ser Gly Val His Thr Phe Pro Ala Val Leu Gln Ser Ser Gly Leu
        290                 295                 300
Tyr Ser Leu Ser Ser Val Val Thr Val Pro Ser Ser Ser Leu Gly Thr
305                 310                 315                 320
Gln Thr Tyr Ile Cys Asn Val Asn His Lys Pro Ser Asn Thr Lys Val
                325                 330                 335
Asp Lys Lys Val Glu Pro Lys Ser Cys Asp Lys Thr His Thr Cys Pro
            340                 345                 350
Pro Cys Pro Ala Pro Glu Leu Leu Gly Gly Pro Ser Val Phe Leu Phe
        355                 360                 365
Pro Pro Lys Pro Lys Asp Thr Leu Met Ile Ser Arg Thr Pro Glu Val
370                 375                 380
Thr Cys Val Val Val Asp Val Ser His Glu Asp Pro Glu Val Lys Phe
385                 390                 395                 400
Asn Trp Tyr Val Asp Gly Val Glu Val His Asn Ala Lys Thr Lys Pro
                405                 410                 415
Arg Glu Glu Gln Tyr Asn Ser Thr Tyr Arg Val Val Ser Val Leu Thr
            420                 425                 430
Val Leu His Gln Asp Trp Leu Asn Gly Lys Glu Tyr Lys Cys Lys Val
        435                 440                 445
Ser Asn Lys Ala Leu Pro Ala Pro Ile Glu Lys Thr Ile Ser Lys Ala
        450                 455                 460
Lys Gly Gln Pro Arg Glu Pro Gln Val Tyr Thr Leu Pro Pro Ser Arg
465                 470                 475                 480
Asp Glu Leu Thr Lys Asn Gln Val Ser Leu Thr Cys Leu Val Lys Gly
                485                 490                 495
Phe Tyr Pro Ser Asp Ile Ala Val Glu Trp Glu Ser Asn Gly Gln Pro
            500                 505                 510
Glu Asn Asn Tyr Lys Thr Thr Pro Pro Val Leu Asp Ser Asp Gly Ser
```

-continued

```
                515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 36
<211> LENGTH: 572
<212> TYPE: PRT
<213> ORGANISM: Artificial Sequence
<220> FEATURE:
<223> OTHER INFORMATION: Heavy chain sequence for cross over dual V-Ig
      having code HC14

<400> SEQUENCE: 36

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gly Glu Val Gln Leu Val Gln
        115                 120                 125

Ser Gly Ala Glu Val Lys Lys Pro Gly Glu Ser Leu Lys Ile Ser Cys
    130                 135                 140

Lys Gly Ser Gly Tyr Ser Phe Thr Thr Tyr Trp Leu Gly Trp Val Arg
145                 150                 155                 160

Gln Met Pro Gly Lys Gly Leu Asp Trp Ile Gly Ile Met Ser Pro Val
                165                 170                 175

Asp Ser Asp Ile Arg Tyr Ser Pro Ser Phe Gln Gly Gln Val Thr Met
            180                 185                 190

Ser Val Asp Lys Ser Ile Thr Thr Ala Tyr Leu Gln Trp Asn Ser Leu
        195                 200                 205

Lys Ala Ser Asp Thr Ala Met Tyr Tyr Cys Ala Arg Arg Arg Pro Gly
    210                 215                 220

Gln Gly Tyr Phe Asp Phe Trp Gly Gln Gly Thr Leu Val Thr Val Ser
225                 230                 235                 240

Ser Gly Gly Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300
```

```
Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
            325                 330                 335

Val Asp Lys Lys Val Glu Pro Lys Ser Cys Asp Lys Thr His Thr Cys
        340                 345                 350

Pro Pro Cys Pro Ala Pro Glu Leu Leu Gly Gly Pro Ser Val Phe Leu
    355                 360                 365

Phe Pro Pro Lys Pro Lys Asp Thr Leu Met Ile Ser Arg Thr Pro Glu
370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
        435                 440                 445

Val Ser Asn Lys Ala Leu Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Asp Glu Leu Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
        515                 520                 525

Ser Phe Phe Leu Tyr Ser Lys Leu Thr Val Asp Lys Ser Arg Trp Gln
530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly
                565                 570

<210> SEQ ID NO 37
<211> LENGTH: 572
<212> TYPE: PRT
<213> ORGANISM: Artificial Sequence
<220> FEATURE:
<223> OTHER INFORMATION: Heavy chain sequence for cross over dual V-Ig
      having code HC15

<400> SEQUENCE: 37

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95
```

-continued

```
Ala Arg Arg Arg Pro Gly Gln Gly Tyr Phe Asp Phe Trp Gly Gln Gly
            100                 105                 110

Thr Leu Val Thr Val Ser Ser Gly Glu Val Gln Leu Val Glu Ser Gly
            115                 120                 125

Gly Gly Leu Val Gln Pro Gly Arg Ser Leu Arg Leu Ser Cys Ala Ala
            130                 135                 140

Ser Gly Phe Thr Phe Asp Asp Tyr Ala Met His Trp Val Arg Gln Ala
145                 150                 155                 160

Pro Gly Lys Gly Leu Glu Trp Val Ser Ala Ile Thr Trp Asn Ser Gly
            165                 170                 175

His Ile Asp Tyr Ala Asp Ser Val Glu Gly Arg Phe Thr Ile Ser Arg
            180                 185                 190

Asp Asn Ala Lys Asn Ser Leu Tyr Leu Gln Met Asn Ser Leu Arg Ala
            195                 200                 205

Glu Asp Thr Ala Val Tyr Tyr Cys Ala Lys Val Ser Tyr Leu Ser Thr
            210                 215                 220

Ala Ser Ser Leu Asp Tyr Trp Gly Gln Gly Thr Leu Val Thr Val Ser
225                 230                 235                 240

Ser Gly Gly Ala Ser Thr Lys Gly Pro Ser Val Phe Pro Leu Ala Pro
            245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
            290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
            325                 330                 335

Val Asp Lys Lys Val Glu Pro Lys Ser Cys Asp Lys Thr His Thr Cys
            340                 345                 350

Pro Pro Cys Pro Ala Pro Glu Leu Leu Gly Gly Pro Ser Val Phe Leu
            355                 360                 365

Phe Pro Pro Lys Pro Lys Asp Thr Leu Met Ile Ser Arg Thr Pro Glu
            370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
            435                 440                 445

Val Ser Asn Lys Ala Leu Pro Ala Pro Ile Glu Lys Thr Ile Ser Lys
            450                 455                 460

Ala Lys Gly Gln Pro Arg Glu Pro Gln Val Tyr Thr Leu Pro Pro Ser
465                 470                 475                 480

Arg Asp Glu Leu Thr Lys Asn Gln Val Ser Leu Thr Cys Leu Val Lys
            485                 490                 495

Gly Phe Tyr Pro Ser Asp Ile Ala Val Glu Trp Glu Ser Asn Gly Gln
            500                 505                 510
```

```
Pro Glu Asn Asn Tyr Lys Thr Thr Pro Pro Val Leu Asp Ser Asp Gly
            515                 520                 525

Ser Phe Phe Leu Tyr Ser Lys Leu Thr Val Asp Lys Ser Arg Trp Gln
        530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly
            565                 570

<210> SEQ ID NO 38
<211> LENGTH: 571
<212> TYPE: PRT
<213> ORGANISM: Artificial Sequence
<220> FEATURE:
<223> OTHER INFORMATION: Heavy chain sequence for cross over dual V-Ig
      having code HC16

<400> SEQUENCE: 38

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gly Gln Val Gln Leu Val Glu
        115                 120                 125

Ser Gly Gly Gly Val Val Gln Pro Gly Arg Ser Leu Arg Leu Ser Cys
    130                 135                 140

Ala Ala Ser Gly Phe Thr Phe Ser Val Tyr Gly Met Asn Trp Val Arg
145                 150                 155                 160

Gln Ala Pro Gly Lys Gly Leu Glu Trp Val Ala Ile Ile Trp Tyr Asp
                165                 170                 175

Gly Asp Asn Gln Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Gly Leu
        195                 200                 205

Arg Ala Glu Asp Thr Ala Val Tyr Tyr Cys Ala Arg Asp Leu Arg Thr
    210                 215                 220

Gly Pro Phe Asp Tyr Trp Gly Gln Gly Thr Leu Val Thr Val Ser Ser
225                 230                 235                 240

Gly Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300
```

```
Tyr Ser Leu Ser Ser Val Val Thr Val Pro Ser Ser Leu Gly Thr
305                 310                 315                 320

Gln Thr Tyr Ile Cys Asn Val Asn His Lys Pro Ser Asn Thr Lys Val
            325                 330                 335

Asp Lys Lys Val Glu Pro Lys Ser Cys Asp Lys Thr His Thr Cys Pro
        340                 345                 350

Pro Cys Pro Ala Pro Glu Leu Leu Gly Gly Pro Ser Val Phe Leu Phe
    355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 39
<211> LENGTH: 571
<212> TYPE: PRT
<213> ORGANISM: Artificial Sequence
<220> FEATURE:
<223> OTHER INFORMATION: Heavy chain sequence for cross over dual V-Ig
      having code HC17

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
```

```
                         85                  90                  95
Ala Arg Asp Leu Arg Thr Gly Pro Phe Asp Tyr Trp Gly Gln Gly Thr
                100                 105                 110

Leu Val Thr Val Ser Ser Gly Glu Val Gln Leu Val Glu Ser Gly Gly
                115                 120                 125

Gly Leu Val Gln Pro Gly Arg Ser Leu Arg Leu Ser Cys Ala Ala Ser
        130                 135                 140

Gly Phe Thr Phe Asp Asp Tyr Ala Met His Trp Val Arg Gln Ala Pro
145                 150                 155                 160

Gly Lys Gly Leu Glu Trp Val Ser Ala Ile Thr Trp Asn Ser Gly His
                165                 170                 175

Ile Asp Tyr Ala Asp Ser Val Glu Gly Arg Phe Thr Ile Ser Arg Asp
                180                 185                 190

Asn Ala Lys Asn Ser Leu Tyr Leu Gln Met Asn Ser Leu Arg Ala Glu
                195                 200                 205

Asp Thr Ala Val Tyr Tyr Cys Ala Lys Val Ser Tyr Leu Ser Thr Ala
        210                 215                 220

Ser Ser Leu Asp Tyr Trp Gly Gln Gly Thr Leu Val Thr Val Ser Ser
225                 230                 235                 240

Gly Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
                260                 265                 270

Asp Tyr Phe Pro Glu Pro Val Thr Val Ser Trp Asn Ser Gly Ala Leu
                275                 280                 285

Thr Ser Gly Val His Thr Phe Pro Ala Val Leu Gln Ser Ser Gly Leu
        290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Lys Val Glu Pro Lys Ser Cys Asp Lys Thr His Thr Cys Pro
                340                 345                 350

Pro Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
                420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
                500                 505                 510
```

Glu Asn Asn Tyr Lys Thr Thr Pro Val Leu Asp Ser Asp Gly Ser
            515                 520                 525

Phe Phe Leu Tyr Ser Lys Leu Thr Val Asp Lys Ser Arg Trp Gln Gln
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
            565                 570

<210> SEQ ID NO 40
<211> LENGTH: 334
<212> TYPE: PRT
<213> ORGANISM: Artificial Sequence
<220> FEATURE:
<223> OTHER INFORMATION: Light chain sequence for cross over dual V-Ig
      having code LC10

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Gly Gly Gly Gly
            100                 105                 110

Gly Gly Ser Ser Glu Leu Thr Gln Asp Pro Ala Val Ser Val Ala Leu
        115                 120                 125

Gly Gln Thr Val Arg Ile Thr Cys Gln Gly Asp Ser Leu Arg Ser Tyr
    130                 135                 140

Tyr Ala Thr Trp Tyr Gln Gln Lys Pro Gly Gln Ala Pro Ile Leu Val
145                 150                 155                 160

Ile Tyr Gly Glu Asn Lys Arg Pro Ser Gly Ile Pro Asp Arg Phe Ser
            165                 170                 175

Gly Ser Ser Ser Gly Asn Thr Ala Ser Leu Thr Ile Thr Gly Ala Gln
        180                 185                 190

Ala Glu Asp Glu Ala Asp Tyr Tyr Cys Lys Ser Arg Asp Gly Ser Gly
    195                 200                 205

Gln His Leu Val Phe Gly Gly Gly Thr Lys Leu Thr Val Leu Gly Gly
210                 215                 220

Gly Gly Gly Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
            245                 250                 255

Asn Asn Phe Tyr Pro Arg Glu Ala Lys Val Gln Trp Lys Val Asp Asn
        260                 265                 270

Ala Leu Gln Ser Gly Asn Ser Gln Glu Ser Val Thr Glu Gln Asp Ser
    275                 280                 285

Lys Asp Ser Thr Tyr Ser Leu Ser Ser Thr Leu Thr Leu Ser Lys Ala

```
                    290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                    325                 330

<210> SEQ ID NO 41
<211> LENGTH: 334
<212> TYPE: PRT
<213> ORGANISM: Artificial Sequence
<220> FEATURE:
<223> OTHER INFORMATION: Light chain sequence for cross over dual V-Ig
      having code LC11

<400> SEQUENCE: 41

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Thr Trp Tyr Gln Gln Lys Pro Gly Gln Ala Pro Ile Leu Val Ile Tyr
            35                  40                  45

Gly Glu Asn Lys Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly Gly Gly Gly
            100                 105                 110

Gly Gly Gly Asp Ile Gln Met Thr Gln Ser Pro Ser Ser Leu Ser Ala
        115                 120                 125

Ser Val Gly Asp Arg Val Thr Ile Thr Cys Arg Ala Ser Gln Asp Val
130                 135                 140

Asn Thr Ala Val Ala Trp Tyr Gln Gln Lys Pro Gly Lys Ala Pro Lys
145                 150                 155                 160

Leu Leu Ile Tyr Ser Ala Ser Phe Leu Tyr Ser Gly Val Pro Ser Arg
                165                 170                 175

Phe Ser Gly Ser Arg Ser Gly Thr Asp Phe Thr Leu Thr Ile Ser Ser
            180                 185                 190

Leu Gln Pro Glu Asp Phe Ala Thr Tyr Tyr Cys Gln Gln His Tyr Thr
        195                 200                 205

Thr Pro Pro Thr Phe Gly Gln Gly Thr Lys Val Glu Ile Lys Gly Gly
210                 215                 220

Gly Gly Gly Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
        290                 295                 300

Asp Tyr Glu Lys His Lys Val Tyr Ala Cys Glu Val Thr His Gln Gly
305                 310                 315                 320
```

-continued

Leu Ser Ser Pro Val Thr Lys Ser Phe Asn Arg Gly Glu Cys
              325                 330

<210> SEQ ID NO 42
<211> LENGTH: 333
<212> TYPE: PRT
<213> ORGANISM: Artificial Sequence
<220> FEATURE:
<223> OTHER INFORMATION: Light chain sequence for cross over dual V-Ig
      having code LC12

<400> SEQUENCE: 42

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Tyr Gly Ser Thr Pro Leu
                85                  90                  95

Thr Phe Gly Gly Gly Thr Lys Ala Glu Ile Lys Gly Gly Gly Gly
            100                 105                 110

Gly Gly Glu Ile Val Leu Thr Gln Ser Pro Gly Thr Leu Ser Val Ser
        115                 120                 125

Pro Gly Glu Arg Ala Thr Leu Ser Cys Arg Ala Ser Gln Ser Ile Gly
130                 135                 140

Ser Ser Leu His Trp Tyr Gln Gln Lys Pro Gly Gln Ala Pro Arg Leu
145                 150                 155                 160

Leu Ile Lys Tyr Ala Ser Gln Ser Leu Ser Gly Ile Pro Asp Arg Phe
                165                 170                 175

Ser Gly Ser Gly Ser Gly Thr Asp Phe Thr Leu Thr Ile Ser Arg Leu
            180                 185                 190

Glu Pro Glu Asp Phe Ala Val Tyr Tyr Cys His Gln Ser Ser Arg Leu
        195                 200                 205

Pro His Thr Phe Gly Gln Gly Thr Lys Val Glu Ile Lys Gly Gly Gly
    210                 215                 220

Gly Gly Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 43

<211> LENGTH: 333
<212> TYPE: PRT
<213> ORGANISM: Artificial Sequence
<220> FEATURE:
<223> OTHER INFORMATION: Light chain sequence for cross over dual V-Ig having code LC13

<400> SEQUENCE: 43

```
Glu Ile Val Leu Thr Gln Ser Pro Gly Thr Leu Ser Val Ser Pro Gly
1               5                   10                  15
Glu Arg Ala Thr Leu Ser Cys Arg Ala Ser Gln Ser Ile Gly Ser Ser
            20                  25                  30
Leu His Trp Tyr Gln Gln Lys Pro Gly Gln Ala Pro Arg Leu Leu Ile
        35                  40                  45
Lys Tyr Ala Ser Gln Ser Leu Ser Gly Ile Pro Asp Arg Phe Ser Gly
50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys His Gln Ser Ser Arg Leu Pro His
                85                  90                  95
Thr Phe Gly Gln Gly Thr Lys Val Glu Ile Lys Gly Gly Gly Gly
            100                 105                 110
Gly Gly Glu Ile Val Met Thr Gln Ser Pro Ala Thr Leu Ser Leu Ser
        115                 120                 125
Pro Gly Glu Arg Ala Thr Leu Ser Cys Arg Ala Ser Gln Ser Val Ser
130                 135                 140
Ser Tyr Leu Ala Trp Tyr Gln Gln Lys Pro Gly Gln Ala Pro Arg Leu
145                 150                 155                 160
Leu Ile Tyr Asp Ala Ser Asn Arg Ala Thr Gly Ile Pro Ala Arg Phe
                165                 170                 175
Ser Gly Ser Gly Ser Gly Thr Asp Phe Thr Leu Thr Ile Ser Ser Leu
            180                 185                 190
Glu Pro Glu Asp Phe Ala Val Tyr Tyr Cys His Gln Tyr Gly Ser Thr
        195                 200                 205
Pro Leu Thr Phe Gly Gly Gly Thr Lys Ala Glu Ile Lys Gly Gly Gly
210                 215                 220
Gly Gly Arg Thr Val Ala Ala Pro Ser Val Phe Ile Phe Pro Pro Ser
225                 230                 235                 240
Asp Glu Gln Leu Lys Ser Gly Thr Ala Ser Val Val Cys Leu Leu Asn
                245                 250                 255
Asn Phe Tyr Pro Arg Glu Ala Lys Val Gln Trp Lys Val Asp Asn Ala
            260                 265                 270
Leu Gln Ser Gly Asn Ser Gln Glu Ser Val Thr Glu Gln Asp Ser Lys
        275                 280                 285
Asp Ser Thr Tyr Ser Leu Ser Ser Thr Leu Thr Leu Ser Lys Ala Asp
290                 295                 300
Tyr Glu Lys His Lys Val Tyr Ala Cys Glu Val Thr His Gln Gly Leu
305                 310                 315                 320
Ser Ser Pro Val Thr Lys Ser Phe Asn Arg Gly Glu Cys
                325                 330
```

<210> SEQ ID NO 44
<211> LENGTH: 333
<212> TYPE: PRT
<213> ORGANISM: Artificial Sequence
<220> FEATURE:
<223> OTHER INFORMATION: Light chain sequence for cross over dual V-Ig having code LC14

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Gly Gly Gly Gly Gly
            100                 105                 110

Gly Gly Asp Ile Gln Met Thr Gln Ser Pro Ser Ser Leu Ser Ala Ser
        115                 120                 125

Val Gly Asp Arg Val Thr Ile Thr Cys Arg Ala Ser Gln Gly Ile Arg
130                 135                 140

Asn Tyr Leu Ala Trp Tyr Gln Gln Lys Pro Gly Lys Ala Pro Lys Leu
145                 150                 155                 160

Leu Ile Tyr Ala Ala Ser Thr Leu Gln Ser Gly Val Pro Ser Arg Phe
                165                 170                 175

Ser Gly Ser Gly Ser Gly Thr Asp Phe Thr Leu Thr Ile Ser Ser Leu
            180                 185                 190

Gln Pro Glu Asp Val Ala Thr Tyr Tyr Cys Gln Arg Tyr Asn Arg Ala
        195                 200                 205

Pro Tyr Thr Phe Gly Gln Gly Thr Lys Val Glu Ile Lys Gly Gly Gly
    210                 215                 220

Gly Gly Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 45
<211> LENGTH: 333
<212> TYPE: PRT
<213> ORGANISM: Artificial Sequence
<220> FEATURE:
<223> OTHER INFORMATION: Light chain sequence for cross over dual V-Ig
      having code LC15

<400> SEQUENCE: 45

Asp Ile Gln Met Thr Gln Ser Pro Ser Ser Leu Ser Ala Ser Val Gly

```
            1               5                  10                 15
         Asp Arg Val Thr Ile Thr Cys Arg Ala Ser Gln Gly Ile Arg Asn Tyr
                         20                 25                 30

Leu Ala Trp Tyr Gln Gln Lys Pro Gly Lys Ala Pro Lys Leu Leu Ile
                         35                 40                 45

Tyr Ala Ala Ser Thr Leu Gln Ser Gly Val Pro Ser Arg Phe Ser Gly
                         50                 55                 60

Ser Gly Ser Gly Thr Asp Phe Thr Leu Thr Ile Ser Ser Leu Gln Pro
         65                  70                 75                 80

Glu Asp Val Ala Thr Tyr Tyr Cys Gln Arg Tyr Asn Arg Ala Pro Tyr
                         85                 90                 95

Thr Phe Gly Gln Gly Thr Lys Val Glu Ile Lys Gly Gly Gly Gly Gly
                         100                105                110

Gly Gly Asp Ile Gln Met Thr Gln Ser Pro Ser Ser Leu Ser Ala Ser
                         115                120                125

Val Gly Asp Arg Val Thr Ile Thr Cys Arg Ala Ser Gln Gly Ile Ser
         130                 135                140

Ser Trp Leu Ala Trp Tyr Gln Gln Lys Pro Glu Lys Ala Pro Lys Ser
         145                 150                155                160

Leu Ile Tyr Ala Ala Ser Ser Leu Gln Ser Gly Val Pro Ser Arg Phe
                         165                170                175

Ser Gly Ser Gly Ser Gly Thr Asp Phe Thr Leu Thr Ile Ser Ser Leu
                         180                185                190

Gln Pro Glu Asp Phe Ala Thr Tyr Tyr Cys Gln Gln Tyr Asn Ile Tyr
                         195                200                205

Pro Tyr Thr Phe Gly Gln Gly Thr Lys Leu Glu Ile Lys Gly Gly Gly
                         210                215                220

Gly Gly Arg Thr Val Ala Ala Pro Ser Val Phe Ile Phe Pro Pro Ser
         225                 230                235                240

Asp Glu Gln Leu Lys Ser Gly Thr Ala Ser Val Val Cys Leu Leu Asn
                         245                250                255

Asn Phe Tyr Pro Arg Glu Ala Lys Val Gln Trp Lys Val Asp Asn Ala
                         260                265                270

Leu Gln Ser Gly Asn Ser Gln Glu Ser Val Thr Glu Gln Asp Ser Lys
                         275                280                285

Asp Ser Thr Tyr Ser Leu Ser Thr Leu Thr Leu Ser Lys Ala Asp
                         290                295                300

Tyr Glu Lys His Lys Val Tyr Ala Cys Glu Val Thr His Gln Gly Leu
         305                 310                315                320

Ser Ser Pro Val Thr Lys Ser Phe Asn Arg Gly Glu Cys
                         325                330

<210> SEQ ID NO 46
<211> LENGTH: 333
<212> TYPE: PRT
<213> ORGANISM: Artificial Sequence
<220> FEATURE:
<223> OTHER INFORMATION: Light chain sequence for cross over dual V-Ig
      having code LC16

<400> SEQUENCE: 46

Glu Ile Val Leu Thr Gln Ser Pro Asp Phe Gln Ser Val Thr Pro Lys
1               5                  10                 15

Glu Lys Val Thr Ile Thr Cys Arg Ala Ser Gln Ser Ile Gly Ser Ser
                20                 25                 30
```

-continued

```
Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys His Gln Ser Ser Ser Leu Pro Phe
                 85                  90                  95

Thr Phe Gly Pro Gly Thr Lys Val Asp Ile Lys Gly Gly Gly Gly
                100                 105                 110

Gly Gly Asp Ile Gln Met Thr Gln Ser Pro Ser Ser Leu Ser Ala Ser
            115                 120                 125

Val Gly Asp Arg Val Thr Ile Thr Cys Arg Ala Ser Gln Gly Ile Arg
130                 135                 140

Asn Tyr Leu Ala Trp Tyr Gln Gln Lys Pro Gly Lys Ala Pro Lys Leu
145                 150                 155                 160

Leu Ile Tyr Ala Ala Ser Thr Leu Gln Ser Gly Val Pro Ser Arg Phe
                165                 170                 175

Ser Gly Ser Gly Ser Gly Thr Asp Phe Thr Leu Thr Ile Ser Ser Leu
                180                 185                 190

Gln Pro Glu Asp Val Ala Thr Tyr Tyr Cys Gln Arg Tyr Asn Arg Ala
            195                 200                 205

Pro Tyr Thr Phe Gly Gln Gly Thr Lys Val Glu Ile Lys Gly Gly Gly
210                 215                 220

Gly Gly Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
                260                 265                 270

Leu Gln Ser Gly Asn Ser Gln Glu Ser Val Thr Glu Gln Asp Ser Lys
            275                 280                 285

Asp Ser Thr Tyr Ser Leu Ser Ser Thr Leu Thr Leu Ser Lys Ala Asp
290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330
```

<210> SEQ ID NO 47
<211> LENGTH: 333
<212> TYPE: PRT
<213> ORGANISM: Artificial Sequence
<220> FEATURE:
<223> OTHER INFORMATION: Light chain sequence for cross over dual V-Ig having code LC17

<400> SEQUENCE: 47

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Gly Gly Gly Gly Gly
            100                 105                 110

Gly Gly Glu Ile Val Leu Thr Gln Ser Pro Asp Phe Gln Ser Val Thr
        115                 120                 125

Pro Lys Glu Lys Val Thr Ile Thr Cys Arg Ala Ser Gln Ser Ile Gly
    130                 135                 140

Ser Ser Leu His Trp Tyr Gln Gln Lys Pro Asp Gln Ser Pro Lys Leu
145                 150                 155                 160

Leu Ile Lys Tyr Ala Ser Gln Ser Phe Ser Gly Val Pro Ser Arg Phe
                165                 170                 175

Ser Gly Ser Gly Ser Gly Thr Asp Phe Thr Leu Thr Ile Asn Ser Leu
            180                 185                 190

Glu Ala Glu Asp Ala Ala Tyr Tyr Cys His Gln Ser Ser Ser Leu
        195                 200                 205

Pro Phe Thr Phe Gly Pro Gly Thr Lys Val Asp Ile Lys Gly Gly Gly
    210                 215                 220

Gly Gly Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255

Asn Phe Tyr Pro Arg Glu Ala Lys Val Gln Trp Lys Val Asp Asn Ala
            260                 265                 270

Leu Gln Ser Gly Asn Ser Gln Glu Ser Val Thr Glu Gln Asp Ser Lys
        275                 280                 285

Asp Ser Thr Tyr Ser Leu Ser Ser Thr Leu Thr Leu Ser Lys Ala Asp
    290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 48
<211> LENGTH: 7
<212> TYPE: PRT
<213> ORGANISM: Artificial Sequence
<220> FEATURE:
<223> OTHER INFORMATION: Peptide linker

<400> SEQUENCE: 48

Ala Ser Thr Lys Gly Pro Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Peptide linker

<400> SEQUENCE: 49

Arg Thr Val Ala Ala Pro Ser
1               5
```

```
<210> SEQ ID NO 50
<211> LENGTH: 7
<212> TYPE: PRT
<213> ORGANISM: Artificial Sequence
<220> FEATURE:
<223> OTHER INFORMATION: Peptide linker

<400> SEQUENCE: 50

Gly Gln Pro Lys Ala Ala Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Peptide linker

<400> SEQUENCE: 51

His Ile Asp Ser Pro Asn Lys
1               5

<210> SEQ ID NO 52
<211> LENGTH: 5
<212> TYPE: PRT
<213> ORGANISM: Artificial Sequence
<220> FEATURE:
<223> OTHER INFORMATION: Peptide linker

<400> SEQUENCE: 52

Thr Lys Gly Pro Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Peptide linker

<400> SEQUENCE: 53

Thr Val Ala Ala Pro
1               5

<210> SEQ ID NO 54
<211> LENGTH: 5
<212> TYPE: PRT
<213> ORGANISM: Artificial Sequence
<220> FEATURE:
<223> OTHER INFORMATION: Peptide linker

<400> SEQUENCE: 54

Gln Pro Lys Ala Ala
1               5

<210> SEQ ID NO 55
<211> LENGTH: 5
<212> TYPE: PRT
<213> ORGANISM: Artificial Sequence
<220> FEATURE:
<223> OTHER INFORMATION: Peptide linker

<400> SEQUENCE: 55

Gln Arg Ile Glu Gly
1               5

<210> SEQ ID NO 56
```

```
<211> LENGTH: 7
<212> TYPE: PRT
<213> ORGANISM: Artificial Sequence
<220> FEATURE:
<223> OTHER INFORMATION: Artificial peptide linker

<400> SEQUENCE: 56

Gly Gly Cys Gly Gly Gly Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Artificial peptide linker

<400> SEQUENCE: 57

Gly Gly Gly Cys Gly Gly Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Artificial peptide linker

<400> SEQUENCE: 58

Gly Gly Gly Gly Cys Gly Gly
1               5

<210> SEQ ID NO 59
<211> LENGTH: 7
<212> TYPE: PRT
<213> ORGANISM: Artificial Sequence
<220> FEATURE:
<223> OTHER INFORMATION: Artificial peptide linker

<400> SEQUENCE: 59

Gly Gly Gly Gly Gly Cys Gly
1               5
```

What is claimed is:

1. An isolated nucleic acid molecule comprising a nucleotide sequence encoding an antibody-like binding protein comprising four polypeptide chains that form four antigen binding sites, wherein two polypeptide chains have a structure represented by the formula:

$$V_{L1}\text{-}L_1\text{-}V_{L2}\text{-}L_2\text{-}C_L \quad [\text{I}]$$

and two polypeptide chains have a structure represented by the formula:

$$V_{H2}\text{-}L_3\text{-}V_{H1}\text{-}L_4\text{-}C_{H1}\text{-}Fc \quad [\text{II}]$$

wherein:
  $V_{L1}$ is a first immunoglobulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain;
  Fc is the immunoglobulin hinge region and $C_{H2}$, $C_{H3}$ immunoglobulin heavy chain constant domains; and
  $L_1$, $L_2$, $L_3$, and $L_4$ are amino acid linkers;
wherein:
  $L_1$ is 3 to 12 amino acid residues in length;
  $L_2$ is 3 to 14 amino acid residues in length;
  $L_3$ is 1 to 8 amino acid residues in length; and
  $L_4$ is 1 to 3 amino acid residues in length;
and wherein the polypeptides of formula I and the polypeptides of formula II form a cross-over light chain-heavy chain pair.

2. The isolated nucleic acid molecule of claim 1, wherein:
  $L_1$ is 5 to 10 amino acid residues in length;
  $L_2$ is 5 to 8 amino acid residues in length;
  $L_3$ is 1 to 5 amino acid residues in length; and
  $L_4$ is 1 to 2 amino acid residues in length.

3. An isolated nucleic acid molecule comprising a nucleotide sequence encoding an antibody-like binding protein comprising four polypeptide chains that form four antigen binding sites, wherein two polypeptide chains have a structure represented by the formula:

$$V_{L1}\text{-}L_1\text{-}V_{L2}\text{-}L_2\text{-}C_L \quad [\text{I}]$$

and two polypeptide chains have a structure represented by the formula:

$$V_{H2}\text{-}L_3\text{-}V_{H1}\text{-}L_4\text{-}C_{H1}\text{-}Fc \qquad [II]$$

wherein:
  $V_{L1}$ is a first immuno globulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain;
  Fc is the immunoglobulin hinge region and $C_{H2}$, $C_{H3}$ immunoglobulin heavy chain constant domains; and
  $L_1$, $L_2$, $L_3$ and $L_4$ are amino acid linkers;
wherein:
  $L_1$ is 7 amino acid residues in length;
  $L_2$ is 5 amino acid residues in length;
  $L_3$ is 1 amino acid residue in length; and
  $L_4$ is 2 amino acid residues in length;
and wherein the polypeptides of formula I and the polypeptides of formula II form a cross-over light chain-heavy chain pair.

4. An isolated nucleic acid molecule comprising a nucleotide sequence encoding an antibody-like binding protein comprising four polypeptide chains that form four antigen binding sites, wherein two polypeptide chains have a structure represented by the formula:

$$V_{L1}\text{-}L_1\text{-}V_{L2}\text{-}L_2\text{-}C_L \qquad [I]$$

and two polypeptide chains have a structure represented by the formula:

$$V_{H2}\text{-}L_3\text{-}V_{H1}\text{-}L_4\text{-}C_{H1}\text{-}Fc \qquad [II]$$

wherein:
  $V_{L1}$ is a first immuno globulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain;
  Fc is the immunoglobulin hinge region and $C_{H2}$, $C_{H3}$ immunoglobulin heavy chain constant domains; and
  $L_1$, $L_2$, $L_3$ and $L_4$ are amino acid linkers;
wherein:
  $L_1$ is 1 to 3 amino acid residues in length;
  $L_2$ is 1 to 4 amino acid residues in length;
  $L_3$ is 2 to 15 amino acid residues in length; and
  $L_4$ is 2 to 15 amino acid residues in length;
and wherein the polypeptides of formula I and the polypeptides of formula II form a cross-over light chain-heavy chain pair.

5. The isolated nucleic acid molecule of claim 4, wherein:
  $L_1$ is 1 to 2 amino acid residues in length;
  $L_2$ is 1 to 2 amino acid residues in length;
  $L_3$ is 4 to 12 amino acid residues in length; and
  $L_4$ is 2 to 12 amino acid residues in length.

6. An isolated nucleic acid molecule comprising a nucleotide sequence encoding an antibody-like binding protein comprising four polypeptide chains that form four antigen binding sites, wherein two polypeptide chains have a structure represented by the formula:

$$V_{L1}\text{-}L_1\text{-}V_{L2}\text{-}L_2\text{-}C_L \qquad [I]$$

and two polypeptide chains have a structure represented by the formula:

$$V_{H2}\text{-}L_3\text{-}V_{H1}\text{-}L_4\text{-}C_{H1}\text{-}Fc \qquad [II]$$

wherein:
  $V_{L1}$ is a first immuno globulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain;
  Fc is the immunoglobulin hinge region and $C_{H2}$, $C_{H3}$ immunoglobulin heavy chain constant domains; and
  $L_1$, $L_2$, $L_3$ and $L_4$ are amino acid linkers;
wherein:
  $L_1$ is 1 amino acid residue in length;
  $L_2$ is 2 amino acid residues in length;
  $L_3$ is 7 amino acid residues in length; and
  $L_4$ is 5 amino acid residues in length;
and wherein the polypeptides of formula I and the polypeptides of formula II form a cross-over light chain-heavy chain pair.

7. An isolated nucleic acid molecule comprising a nucleotide sequence encoding an antibody-like binding protein comprising two polypeptide chains that form two antigen binding sites, wherein a first polypeptide chain has a structure represented by the formula:

$$V_{L1}\text{-}L_1\text{-}V_{L2}\text{-}L_2\text{-}C_L \qquad [I]$$

and a second polypeptide chain has a structure represented by the formula:

$$V_{H2}\text{-}L_3\text{-}V_{H1}\text{-}L_4\text{-}C_{H1} \qquad [II]$$

wherein:
  $V_{L1}$ is a first immunoglobulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain; and
  $L_1$, $L_2$, $L_3$, and $L_4$ are amino acid linkers;
wherein:
  $L_1$ is 3 to 12 amino acid residues in length;
  $L_2$ is 3 to 14 amino acid residues in length;
  $L_3$ is 1 to 8 amino acid residues in length; and
  $L_4$ is 1 to 3 amino acid residues in length;
and wherein the first and second polypeptides form a cross-over light chain-heavy chain pair.

8. The isolated nucleic acid molecule of claim 7, wherein:
  $L_1$ is 5 to 10 amino acid residues in length;
  $L_2$ is 5 to 8 amino acid residues in length;
  $L_3$ is 1 to 5 amino acid residues in length; and
  $L_4$ is 1 to 2 amino acid residues in length.

9. An isolated nucleic acid molecule comprising a nucleotide sequence encoding an antibody-like binding protein comprising two polypeptide chains that form two antigen binding sites, wherein a first polypeptide chain has a structure represented by the formula:

$$V_{L1}\text{-}L_1\text{-}V_{L2}\text{-}L_2\text{-}C_L \qquad [I]$$

and a second polypeptide chain has a structure represented by the formula:

$$V_{H2}\text{-}L_3\text{-}V_{H1}\text{-}L_4\text{-}C_{H1} \qquad [II]$$

wherein:
  $V_{L1}$ is a first immuno globulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain; and
  $L_1, L_2, L_3$ and $L_4$ are amino acid linkers;
  $L_1$ is 7 amino acid residues in length;
  $L_2$ is 5 amino acid residues in length;
  $L_3$ is 1 amino acid residue in length; and
  $L_4$ is 2 amino acid residues in length;
and wherein the first and second polypeptides form a cross-over light chain-heavy chain pair.

10. An isolated nucleic acid molecule comprising a nucleotide sequence encoding an antibody-like binding protein comprising two polypeptide chains that form two antigen binding sites, wherein a first polypeptide chain has a structure represented by the formula:

$$V_{L1}\text{-}L_1\text{-}V_{L2}\text{-}L_2\text{-}C_L \qquad [I]$$

and a second polypeptide chain has a structure represented by the formula:

$$V_{H2}\text{-}L_3\text{-}V_{H1}\text{-}L_4\text{-}C_{H1} \qquad [II]$$

wherein:
  $V_{L1}$ is a first immuno globulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain; and
  $L_1, L_2, L_3$ and $L_4$ are amino acid linkers;
  $L_1$ is 1 to 3 amino acid residues in length;
  $L_2$ is 1 to 4 amino acid residues in length;
  $L_3$ is 2 to 15 amino acid residues in length; and
  $L_4$ is 2 to 15 amino acid residues in length;
and wherein the first and second polypeptides form a cross-over light chain-heavy chain pair.

11. The isolated nucleic acid molecule of claim 10, wherein:
  $L_1$ is 1 to 2 amino acid residues in length;
  $L_2$ is 1 to 2 amino acid residues in length;
  $L_3$ is 4 to 12 amino acid residues in length; and
  $L_4$ is 2 to 12 amino acid residues in length.

12. An isolated nucleic acid molecule comprising a nucleotide sequence encoding an antibody-like binding protein comprising two polypeptide chains that form two antigen binding sites, wherein a first polypeptide chain has a structure represented by the formula:

$$V_{L1}\text{-}L_1\text{-}V_{L2}\text{-}L_2\text{-}C_L \qquad [I]$$

and a second polypeptide chain has a structure represented by the formula:

$$V_{H2}\text{-}L_3\text{-}V_{H1}\text{-}L_4\text{-}C_{H1} \qquad [II]$$

wherein:
  $V_{L1}$ is a first immuno globulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain; and
  $L_1, L_2, L_3,$ and $L_4$ are amino acid linkers;
  $L_1$ is 1 amino acid residue in length;
  $L_2$ is 2 amino acid residues in length;
  $L_3$ is 7 amino acid residues in length; and
  $L_4$ is 5 amino acid residues in length;
and wherein the first and second polypeptides form a cross-over light chain-heavy chain pair.

13. An isolated nucleic acid molecule comprising a nucleotide sequence encoding an antibody-like binding protein comprising four polypeptide chains that form four antigen binding sites, wherein two polypeptide chains have a structure represented by the formula:

$$V_{L1}\text{-}L_1\text{-}V_{L2}\text{-}L_2\text{-}C_L \qquad [I]$$

and two polypeptide chains have a structure represented by the formula:

$$V_{H2}\text{-}L_3\text{-}V_{H1}\text{-}L_4\text{-}C_{H1}\text{-}Fc \qquad [II]$$

wherein:
  $V_{L1}$ is a first immunoglobulin light chain variable domain;
  $V_{L2}$ is a second immunoglobulin light chain variable domain;
  $V_{H1}$ is a first immunoglobulin heavy chain variable domain;
  $V_{H2}$ is a second immunoglobulin heavy chain variable domain;
  $C_L$ is an immunoglobulin light chain constant domain;
  $C_{H1}$ is the immunoglobulin $C_{H1}$ heavy chain constant domain;
  Fc is the immunoglobulin hinge region and $C_{H2}$, $C_{H3}$ immunoglobulin heavy chain constant domains; and
  $L_1, L_2, L_3,$ and $L_4$ are amino acid linkers;
wherein $L_2$ and $L_4$ are both at least one amino acid in length, and
  (a) the length of $L_2$ is at least twice the length of $L_4$; or
  (b) the length of $L_4$ is at least twice the length of $L_2$;
and wherein the polypeptides of formula I and the polypeptides of formula II form a cross-over light chain-heavy chain pair.

14. An isolated nucleic acid molecule comprising a nucleotide sequence encoding an antibody-like binding protein comprising two polypeptide chains that form two antigen binding sites, wherein a first polypeptide chain has a structure represented by the formula:

$$V_{L1}\text{-}L_1\text{-}V_{L2}\text{-}L_2\text{-}C_L \qquad [I]$$

and a second polypeptide chain has a structure represented by the formula:

$$V_{H2}\text{-}L_3\text{-}V_{H1}\text{-}L_4\text{-}C_{H1} \qquad [II]$$

wherein:
- $V_{L1}$ is a first immunoglobulin light chain variable domain;
- $V_{L2}$ is a second immunoglobulin light chain variable domain;
- $V_{H1}$ is a first immunoglobulin heavy chain variable domain;
- $V_{H2}$ is a second immunoglobulin heavy chain variable domain;
- $C_L$ is an immunoglobulin light chain constant domain;
- $C_{H1}$ is the immunoglobulin $C_{H1}$ heavy chain constant domain; and
- $L_1$, $L_2$, $L_3$, and $L_4$ are amino acid linkers;

wherein $L_2$ and $L_4$ are both at least one amino acid in length, and (a) the length of $L_2$ is at least twice the length of $L_4$; or
(b) the length of $L_4$ is at least twice the length of $L_2$;

and wherein the first and second polypeptides form a crossover light chain-heavy chain pair.

15. An expression vector comprising the nucleic acid molecule of either claim 1, 4, 7, 10, 13, or 14.

16. An isolated host cell comprising the nucleic acid molecule of either claim 1, 4, 7, 10, 13, or 14.

17. The host cell of claim 16, wherein the host cell is a mammalian cell.

18. An isolated host cell comprising the expression vector of claim 15.

19. The host cell of claim 18, wherein the host cell is a mammalian cell or an insect cell.

20. A method for making an antibody-like binding protein comprising expressing the nucleic acid molecule of claim 1, 4, 7, 10, 13, or 14 in a cell.

21. The isolated nucleic acid molecule of claim 1, 4, 7, 10, 13, or 14, wherein the antibody-like binding protein is capable of specifically binding one or more antigen targets.

22. The isolated nucleic acid molecule of claim 21, wherein the one or more antigen targets is selected from the group consisting of B7.1, B7.2, BAFF, BlyS, C3, C5, CCL11 (eotaxin), CCL15 (MIP-1d), CCL17 (TARC), CCL19 (MIP-3b), CCL2 (MCP-1), CCL20 (MIP-3a), CCL21 (MIP-2), SLC, CCL24 (MPIF 2/eotaxin-2), CCL25 (TECK), CCL26 (eotaxin-3), CCL3 (MIP-1a), CCL4 (MIP-1b), CCL5 (RANTES), CCL7 (MCP-3), CCL8 (mcp-2), CD3, CD19, CD20, CD24, CD40, CD40L, CD80, CD86, CDHI (E-cadherin), Chitinase, CSF1 (M-CSF), CSF2 (GM-CSF), CSF3 (GCSF), CTLA4, CX3CL1 (SCYD1), CXCL12 (SDF1), CXCL13, EGFR, FCER1A, FCER2, HER2, IGF1R, IL-1, IL-12, IL13, IL15, IL17, IL18, IL1A, IL1B, IL1FI1, IL1β, IL2, IL4, IL6, IL7, IL8, IL9, IL12/23, IL22, IL23, IL25, IL27, IL35, ITGB4 (b 4 integrin), LEP (leptin), MHC class II, TLR2, TLR4, TLR5, TNF, TNFα, TNFSF4 (OX40 ligand), TNFSF5 (CD40 ligand), Toll-like receptors, TREM1, TSLP, TWEAK, XCR1 (GPR5/CCXCR1), DNGR-1 (CLEC91), and HMGB1.

23. The isolated nucleic acid molecule of claim 1, 4, 7, 10, 13, or 14, wherein the antibody-like binding protein is bispecific and capable of binding two different antigen targets.

24. The isolated nucleic acid molecule of claim 23, wherein the two different antigen targets are selected from the group consisting of IL4 and IL13, IGF1R and HER2, IGF1R and EGFR, EGFR and HER2, BK and IL13, PDL-1 and CTLA-4, CTLA4 and MHC class II, IL-12 and IL-18, IL-1α and IL-1β, TNFα and IL12/23, TNFα and IL-12p40, TNFα and IL1β, TNFα and IL-23, and IL17 and IL23.

25. The isolated nucleic acid molecule of claim 1, 4, 7, 10, 13, or 14, wherein the antibody-like binding protein is capable of inhibiting the function of one or more of the antigen targets.

26. The isolated nucleic acid molecule of claim 1, 4, 7, 10, 13, or 14, wherein at least one of the linkers selected from the group consisting of L1, L2, L3, and L4 contains at least one cysteine residue.

* * * * *

UNITED STATES PATENT AND TRADEMARK OFFICE
CERTIFICATE OF CORRECTION

| | | |
|---|---|---|
| PATENT NO. | : 9,181,349 B2 | Page 1 of 1 |
| APPLICATION NO. | : 13/826126 | |
| DATED | : November 10, 2015 | |
| INVENTOR(S) | : Nicolas Baurin et al. | |

It is certified that error appears in the above-identified patent and that said Letters Patent is hereby corrected as shown below:

ON THE TITLE PAGE

At item (72)

please delete "Chirstian Biel" and replace it with:

--Christian Beil--

Signed and Sealed this
Twenty-ninth Day of March, 2016

Michelle K. Lee
*Director of the United States Patent and Trademark Office*